(12) United States Patent
Armes

(10) Patent No.: US 9,849,252 B2
(45) Date of Patent: Dec. 26, 2017

(54) ELECTROMECHANICAL MANIPULATING DEVICE FOR MEDICAL NEEDLE AND SYRINGE WITH SENSORY BIOFEEDBACK AND PAIN SUPPRESSION CAPABILITY

(71) Applicant: Sofia Eleni Armes, Temple Terrace, FL (US)

(72) Inventor: Charles K. Armes, Fort Collins, CO (US)

( * ) Notice: Subject to any disclaimer, the term of this patent is extended or adjusted under 35 U.S.C. 154(b) by 1114 days.

(21) Appl. No.: 13/886,785

(22) Filed: May 3, 2013

(65) Prior Publication Data

US 2014/0142507 A1    May 22, 2014

Related U.S. Application Data

(60) Provisional application No. 61/642,858, filed on May 4, 2012.

(51) Int. Cl.
*A61M 5/00* (2006.01)
*A61M 5/42* (2006.01)
(Continued)

(52) U.S. Cl.
CPC ............. *A61M 5/422* (2013.01); *A61M 5/20* (2013.01); *A61M 5/3287* (2013.01); *A61M 2005/206* (2013.01)

(58) Field of Classification Search
CPC ........ A61M 5/422; A61M 5/158; A61M 5/46; A61M 2005/1585; A61M 2005/3267
(Continued)

(56) References Cited

U.S. PATENT DOCUMENTS

2005/0215941 A1*  9/2005  Bernard .............. A61M 5/2033
                                                             604/20

\* cited by examiner

*Primary Examiner* — Phillip Gray
(74) *Attorney, Agent, or Firm* — Gordon Ress Scully Mansukhani LLP; David R. Heckadon

(57) ABSTRACT

In an aspect, a medication delivering injector which includes a housing having opposing proximal and distal ends and an accessible internal cavity for inserting and removing a medicament container such as a syringe. The injector is designed to hold and manipulate a medication delivery device such as a large variety of standard and non-standard medical syringes with fixed or attached needles, assembled such that centrally located is a cylinder containing a liquid medicament and attached either permanently or removably to the distal end of the cylinder, is a hypodermic needle or cannula in fluidic communication with the cylinder. The needle can be from one-half inches to one-and-one-half inches in length in the illustrated embodiment and other sizes are possible by changes in scale of the injector. At the proximal end of the cylinder is an opening with an inserted seal or bung with an attached rod thus constituting a plunger. The central medicament containing cylinder could also be a standard medicament cartridge. Hereinafter, both are referred to as a "syringe". A lid or access cover which, in an open position permits insertion and removal of the syringe into/from the housing in a horizontal fashion thus providing ease of loading. The syringe is inserted with the needle end toward the distal end of the housing and the plunger toward the proximal end of the housing. A movable carriage is disposed in the proximal end of the housing and slides in the axial direction forwards and rearwards such that a syringe, whose proximal end is gripped by the carriage, so moves with the carriage such that the needle exits the housing at the distal end of the housing and pierces the tissue of the patient prior to dispensing of the medicament, and then is retracted after the medicament has been dispensed by retraction of the carriage. Attached to the carriage is an actuator which pushes on the syringe plunger causing the medicament contained within the syringe cylinder to be dispensed through the needle into the patient's tissue. In one embodi-
(Continued)

ment suitable for both removable needle and fixed needle syringes, the proximal end of the syringe including the syringe finger flange is gripped by an elastomeric flange grip which resides within the carriage, while the syringe distal end resides in and is supported by a "syringe guide" which is attached to the carriage and thus moved with it. In another embodiment which is so made to accommodate syringes with removable needles and their safe disposal, the syringe flange at the proximal end of the cylinder is gripped by an elastomeric flange grip which resides in the carriage as described above, while the syringe distal end is supported by a needle which resides in a removable disposable needle shield. The needle guide is biased toward the carriage and thus, the syringe body is compressed and guided as the carriage moves forward and rearward.

Both the movement of the carriage and the actuator are controlled by servo motors which are controlled by electronics and a microcontroller so operating such that speeds and accelerations are controlled smoothly and gently so as to avoid the stop/start motion of motors controlled by limit switches and simple electronics or the vibration and abruptness such as result from injectors powered by compressed springs or gas. Furthermore, the forces are adaptive to the loads imposed and the requirements necessary for the proper dispensation of medicaments with high viscosity or sensitivity to shear forces.

The housing, approximately midway between proximal and distal ends, is affixed by a hinge such that the device can be folded in half to provide for a more compact device to be stored and transported.

On the distal end of the housing are electrical sensor pads in communication with the microcontroller such that contact with the patient's skin and the angle at which the injector is held against the skin and the steadiness with which the injector is being held can be ascertained. Within the housing are a haptic vibrator and an audio speaker, both producing a vibration which is variable in pitch in such a manner that biofeedback is provided to the injector user as to the pressure, angle and steadiness with which they are holding the injector against the skin. This facilitates the action of injection oneself in the gluteus muscle where visual feedback isn't available to the patient.

Multiplexed onto the electrical sensor pads, is a TENS (Transcutaneous Electrical Nerve Stimulation) generator which is operational (at the user's choice) just before and during the injection to interrupt or quench the pain of tissue perforation often accompanied with needle injections.

Contained on the surface of the housing such as on the access cover, is a display such that user menus, device state, directions, and battery charge status, etc. are displayed. Also contained on the surface of the housing, on the proximal half, are buttons which control the menus and selections that are shown on the display. These selections provide for the user to set such parameters as hypodermic insertion speed and medicament dispensing speeds, the preferred mode of user biofeedback which can include: speech mode (which can be accompanied by musical themes and ringtones, plus variable pitch tone and haptic vibration), MP3 mode (which has speech muted but includes musical ringtones and variable pitch tone and haptic vibration), and haptic mode (which is haptic vibration and audio tone queues needed for injector position biofeedback and readiness), plus mute mode (which provides no audio but the haptic vibration remains), and none, which provides no vibrational biofeedback, yet the display information always remains available. Also contained on the surface of the housing on the distal half, is an "injection initiate" button which causes the sequences required for performance of an injection to occur if said button is "enabled".

Contained within the electronics and its operating program is the ability to audibly play pre-recorded human speech in any language such that: directions in the form of consecutive steps which are required to load the medicament container (syringe) into the device, consecutive steps to perform an injection, steps to remove and properly dispose of parts, to alert of device status and menu choices, etc. can be played through the audio speaker. Also contained within the electronics and program is the ability to play musical ringtones as a distraction during the needle insertion and injection or when a scheduled injection alarm is reached, or calming human voice exhibiting bedside manner during the needle insertion and injection.

Also contained within the electronics and software is a real-time clock-calendar which can store a patient's injection schedule and play a musical ringtone as an alarm as each scheduled injection becomes due. Also contained within the electronics and software are the ability to communicate with a personal computer through a USB port, which can also charge the injector's rechargeable battery. The battery in one embodiment, consists of three AAA batteries which can be rechargeable or non-rechargeable. The USB port in combination with an application running on the personal computer, is used to download the injection schedule into the real-time clock-calendar and to download ringtones and musical themes of the user's choice and to download foreign language sets for the pre-recorded human language feature.

The injector can be further equipped with the capability to aspirate the tissue by drawing back on the plunger thus creating a vacuum into which fluids will flow. These fluids enter the syringe cylinder where they can be checked for the presence of blood by optical absorption in the red spectrum. This information is useful in the instances where intramuscular injections are to be given with drugs whose 'Full Prescribing Information' instructs the patient to aspirate and check for blood in the syringe which indicates that the puncture of a vein has occurred, and if so detected, to abort the injection and then re-inject into a different location.

17 Claims, 30 Drawing Sheets

(51) Int. Cl.
A61M 5/32 (2006.01)
A61M 5/20 (2006.01)
(58) Field of Classification Search
USPC .................................................. 604/112, 20
See application file for complete search history.

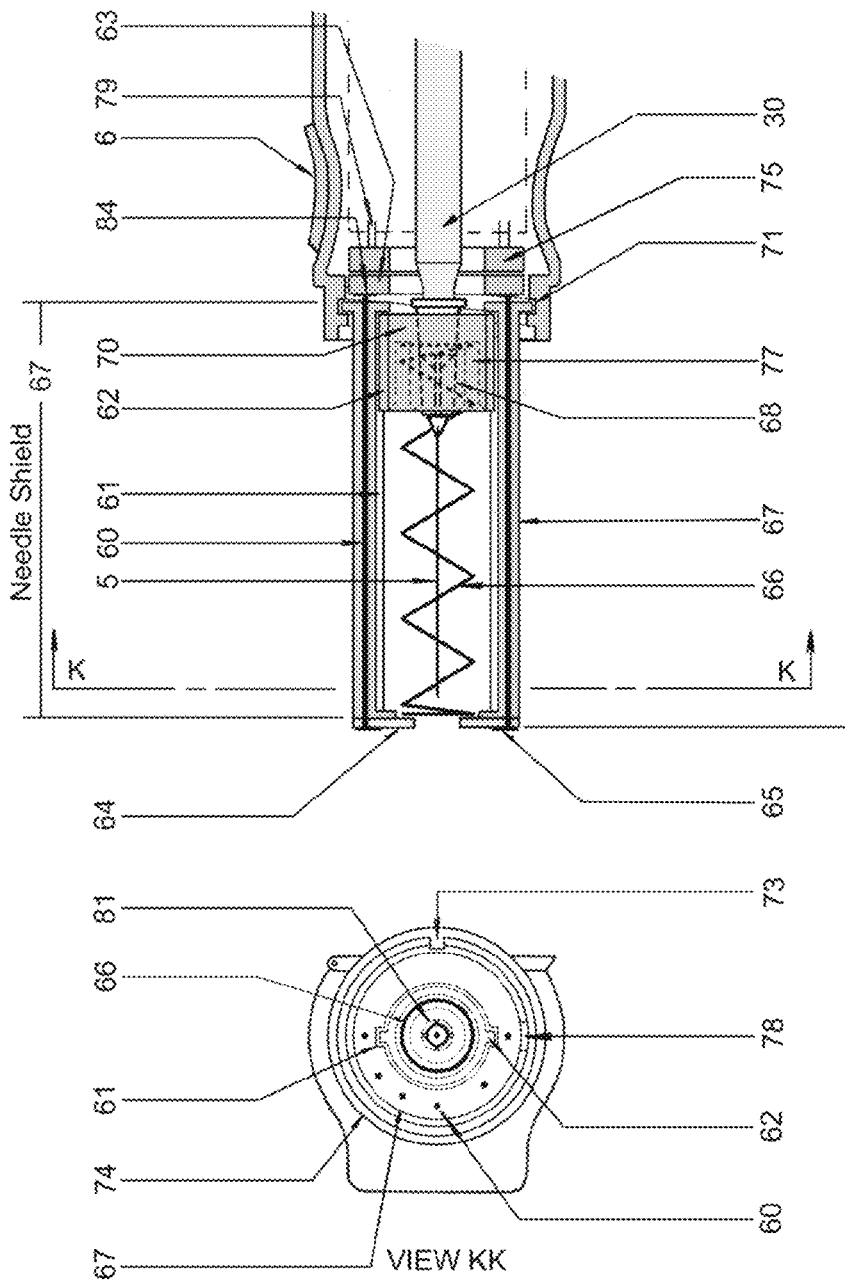

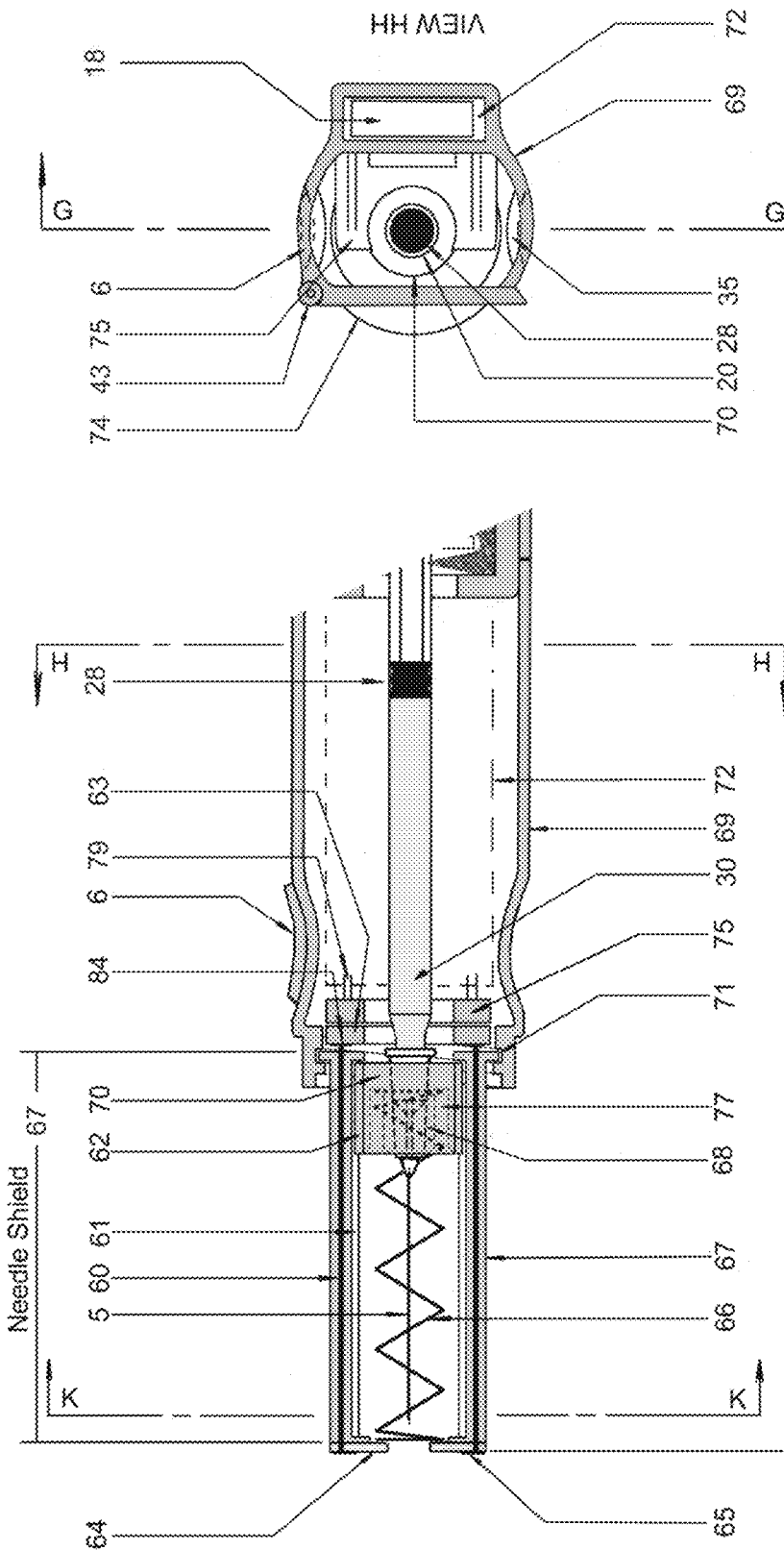

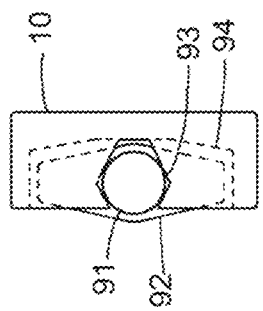
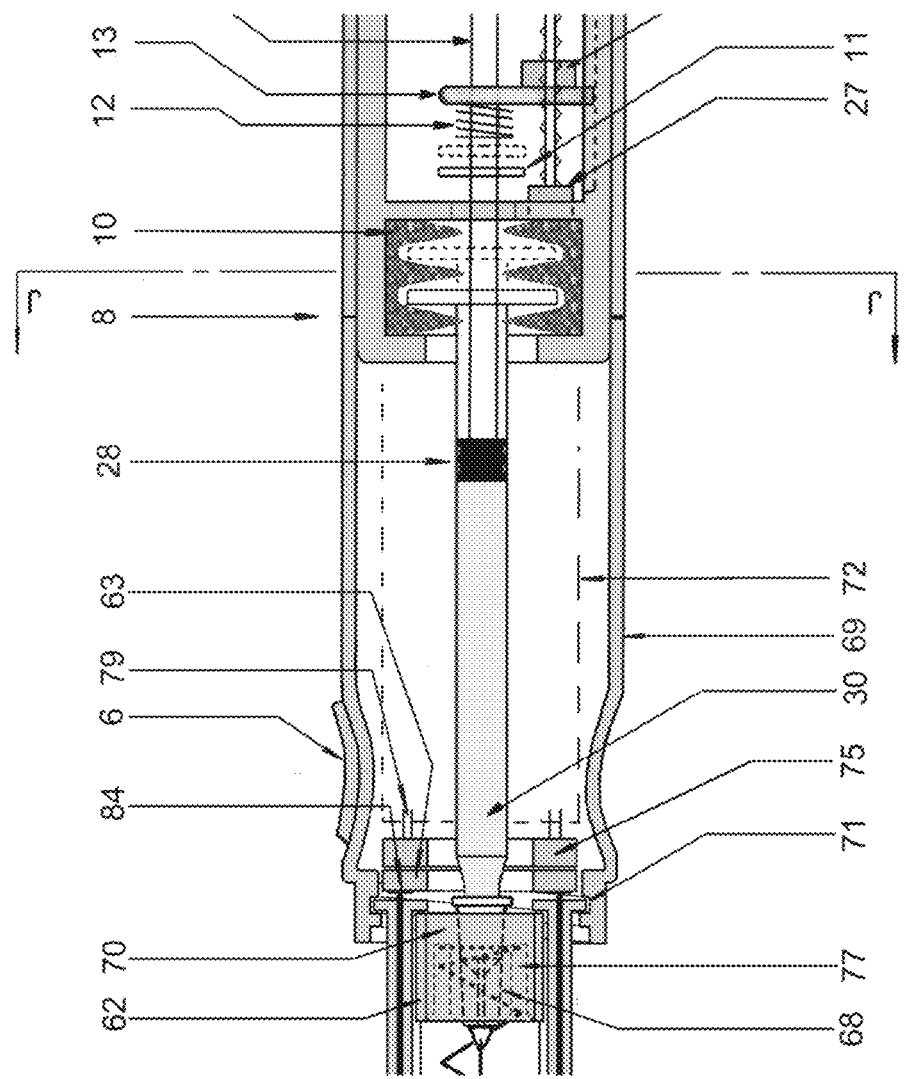
Fig 15b

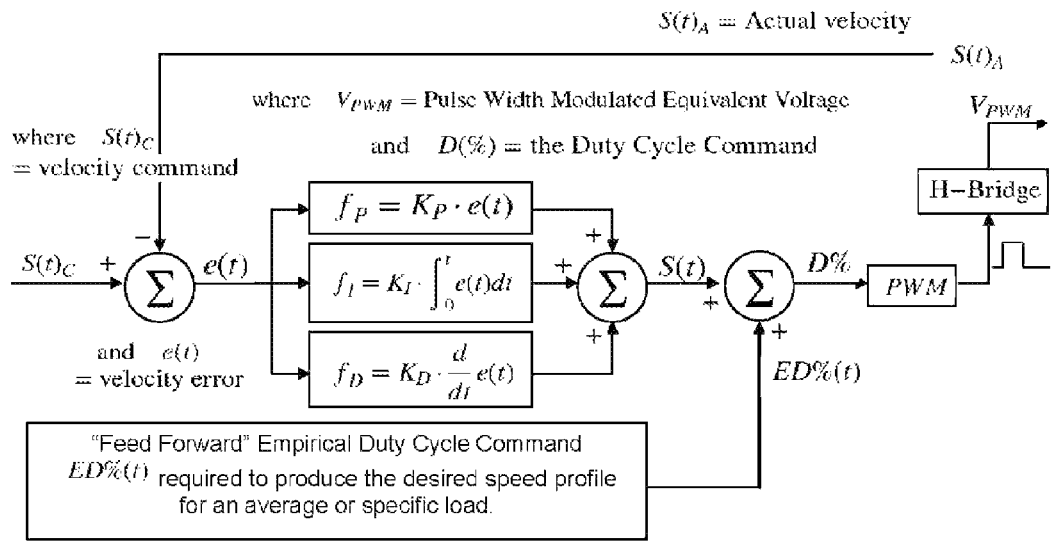

The Ideal parallel PID function: $S(t) = K_P \cdot e(t) + K_I \cdot \int_0^t e(t)dt + K_D \cdot \frac{d}{dt} e(t)$ In digital implementation with discrete time intervals, the PID function becomes:

$$S(t) \approx S(i) = K_P \cdot e(i) + K_I \cdot \sum_{n=1}^{n=k} e(n) \Delta i + K_D \cdot \frac{[e(n) - e(n-1)]}{\Delta i}$$

t is replaced by $i$ = the "interrupt", and $\Delta i$ = the interrupt interval.

where $S(t)$ = speed operator is replaced by the $S(i)$ operator, with units Revolutions per Interrupt)

$e(i)$ = velocity error, and $S(i)_C$ = discrete velocity Command each interval

Since $\Delta i$ is constant and can be factored into $K_I$ and $K_D$, we have:

$$S(i) = K_P \cdot e(i) + K_I \cdot \sum_{n=1}^{n=k} e(n) + K_D \cdot [e(n) - e(n-1)]$$

and $e(i)$ = is calculated as the sum of command $S(i)$ and the inverted feedback signal $S(i)_A$ (the actual speed), which is calculated as $$S_A(i) = \frac{(V_{ref} - (I \cdot R))}{K_e}$$

where $S(i)_A$ = Actual velocity, $I$ = Amps, $R$ = Ohms, and $K_e = \frac{V_{emf}}{\text{rev's}/i}$ $K_e$ being the "Speed Constant" of the motor. $I$ (Amps) is the actual measured variable.

FIG 29

ELECTROMECHANICAL MANIPULATING DEVICE FOR MEDICAL NEEDLE AND SYRINGE WITH SENSORY BIOFEEDBACK AND PAIN SUPPRESSION CAPABILITY

CROSS-REFERENCE TO RELATED APPLICATIONS

Provisional Utility Patent Application No. 61/642,858

STATEMENT REGARDING FEDERALLY SPONSORED RESEARCH OR DEVELOPMENT

Not applicable

FIELD OF THE INVENTION

The present invention is in the technical field of medicament injection devices. More particularly, the present invention is in the technical field of electronic medicament injection devices which can utilize standard fillable or pre-filled syringes as medicament container, although it does not preclude use with cartridge or ampule type medicament containers nor the use of its sensory and pain suppression capabilities with needleless "jet" injectors. Still more particularly, the present invention encompasses the technical field of autoinjectors; however, the autoinjector is a subset of the scope of the invention. That is, the injector does not have to be operated only by the patient as an "auto" or self-injection", but can be used in medical settings by medical professionals or by care-givers and provides automatic or "auto" operational features plus sensory biofeedback and pain suppression features.

BRIEF DESCRIPTION OF RELATED ART

The state of the prior art of medicament injection devices appears to be distributed into the following four groups: 1) standard conventional syringe presentations which are dependant upon the user to possess hand-to-eye coordination and at least some level of steadiness of hand to manipulate the syringe, plus the fortitude to stick a needle into themselves or into another person, 2) injectors which operate on cartridges as medicament container and are either mechanically or electronically powered and inject the medicament from the cartridge through a subcutaneous needle. Often cartridge type injectors provide for multiple dose injections from one cartridge such as with insulin pens, 3) injectors which don't utilize a needle (so called "Jet Injectors") to introduce the medicament into the patient's tissue, but rather utilize a forceful jet of the medicament itself to penetrate the patient's tissue, and 4) so called "auto" injectors (since they are intended for "self injection" and/or because they provide some automation) which are mechanically powered (using compressed springs or gas). Most of these devices are not usable more than once, the whole device being disposable. The autoinjectors operate on syringe like containers or prefilled syringes as the medicament container. Note, these syringe like containers are often specifically designed for use in the autoinjector and do not represent standard syringes or standard prefilled syringes, yet a few devices will operate a standard syringe.

BRIEF SUMMARY OF THE INVENTION

In an aspect, a medication delivering injector which includes a housing having opposing proximal and distal ends and an accessible internal cavity for inserting and removing a medicament container such as a syringe. The injector is designed to hold and manipulate a medication delivery device such as a large variety of standard and non-standard medical syringes with fixed or attached needles, assembled such that centrally located is a cylinder containing a liquid medicament and attached either permanently or removably to the distal end of the cylinder, is a hypodermic needle or cannula in fluidic communication with the cylinder. The needle can be from one-half inches to one-and-one-half inches in length in the illustrated embodiment and other sizes are possible by changes in scale of the injector. At the proximal end of the cylinder is an opening with an inserted seal or bung with an attached rod thus constituting a plunger. The central medicament containing cylinder could also be a standard medicament cartridge. Hereinafter, both are referred to as a "syringe". A lid or access cover which, in an open position permits insertion and removal of the syringe into/from the housing in a horizontal fashion thus providing ease of loading. The syringe is inserted with the needle end toward the distal end of the housing and the plunger toward the proximal end of the housing. A movable carriage is disposed in the proximal end of the housing and slides in the axial direction forwards and rearwards such that a syringe, whose proximal end is gripped by the carriage, so moves with the carriage such that the needle exits the housing at the distal end of the housing and pierces the tissue of the patient prior to dispensing of the medicament, and then is retracted after the medicament has been dispensed by retraction of the carriage. Attached to the carriage is an actuator which pushes on the syringe plunger causing the medicament contained within the syringe cylinder to be dispensed through the needle into the patient's tissue. In one embodiment suitable for both removable needle and fixed needle syringes, the proximal end of the syringe including the syringe finger flange is gripped by an elastomeric flange grip which resides within the carriage, while the syringe distal end resides in and is supported by a "syringe guide" which is attached to the carriage and thus moved with it. In another embodiment which is so made to accommodate syringes with removable needles and their safe disposal, the syringe flange at the proximal end of the cylinder is gripped by an elastomeric flange grip which resides in the carriage as described above, while the syringe distal end is supported by a needle which resides in a removable disposable needle shield. The needle guide is biased toward the carriage and thus, the syringe body is compressed and guided as the carriage moves forward and rearward.

Both the movement of the carriage and the actuator are controlled by servo motors which are controlled by electronics and a microcontroller so operating such that speeds and accelerations are controlled smoothly and gently so as to avoid the stop/start motion of motors controlled by limit switches and simple electronics or the vibration and abruptness such as result from injectors powered by compressed springs or gas. Furthermore, the forces are adaptive to the loads imposed and the requirements necessary for the proper dispensation of medicaments with high viscosity or sensitivity to shear forces.

The housing, approximately midway between proximal and distal ends, is affixed by a hinge such that the device can be folded in half to provide for a more compact device to be stored and transported.

On the distal end of the housing are electrical sensor pads in communication with the microcontroller such that contact with the patient's skin and the angle at which the injector is held against the skin and the steadiness with which the injector is being held can be ascertained. Within the housing are a haptic vibrator and an audio speaker, both producing a vibration which is variable in pitch in such a manner that biofeedback is provided to the injector user as to the pressure, angle and steadiness with which they are holding the injector against the skin. This facilitates the action of injection oneself in the gluteus muscle where visual feedback isn't available to the patient.

Multiplexed onto the electrical sensor pads, is a TENS (Transcutaneous Electrical Nerve Stimulation) generator which is operational (at the user's choice) just before and during the injection to interrupt or quench the pain of tissue perforation often accompanied with needle injections.

Contained on the surface of the housing such as on the access cover, is a display such that user menus, device state, directions, and battery charge status, etc. are displayed. Also contained on the surface of the housing, on the proximal half, are buttons which control the menus and selections that are shown on the display. These selections provide for the user to set such parameters as hypodermic insertion speed and medicament dispensing speeds, the preferred mode of user biofeedback which can include: speech mode (which can be accompanied by musical themes and ringtones, plus variable pitch tone and haptic vibration), MP3 mode (which has speech muted but includes musical ringtones and variable pitch tone and haptic vibration), and haptic mode (which is haptic vibration and audio tone queues needed for injector position biofeedback and readiness), plus mute mode (which provides no audio but the haptic vibration remains), and none, which provides no vibrational biofeedback, yet the display information always remains available.

Also contained on the surface of the housing on the distal half, is an "injection initiate" button which causes the sequences required for performance of an injection to occur if said button is "enabled".

Contained within the electronics and its operating program is the ability to audibly play pre-recorded human speech in any language such that: directions in the form of consecutive steps which are required to load the medicament container (syringe) into the device, consecutive steps to perform an injection, steps to remove and properly dispose of parts, to alert of device status and menu choices, etc. can be played through the audio speaker. Also contained within the electronics and program is the ability, to play musical ringtones as a distraction during the needle insertion and injection or when a scheduled injection alarm is reached, or calming human voice exhibiting bedside manner during the needle insertion and injection.

It is to be noted, that the capability to distract the patient while being given an injection is of considerable value in patient acceptance, compliance, and comfort and is a prominent advancement offered in this invention. This invention provides distraction at many levels, from the audio biofeedback, from the haptic tactile vibrations providing biofeedback, by the process of conscious entrainment with the biofeedback signals, by the musical themes or human spoken language, and by the lack of need for the patient to even watch the injector which completely hides the syringe and needle in the first place.

Also contained within the electronics and software is a real-time clock-calendar which can store a patient's injection schedule and play a musical ringtone as an alarm as each scheduled injection becomes due. Also contained within the electronics and software are the ability to communicate with a personal computer through a USB port, which can also charge the injector's rechargeable battery.

The battery, in one embodiment, consists of three AAA batteries which can be rechargeable or non-rechargeable. The USB port in combination with an application running on the personal computer, is used to download the injection schedule into the real-time clock-calendar and to download ringtones and musical themes of the user's choice and to download foreign language sets for the pre-recorded human language feature.

The injector can be further equipped with the capability to aspirate the tissue by drawing back on the plunger thus creating a vacuum into which fluids will flow. These fluids enter the syringe cylinder where they can be checked for the presence of blood by optical absorption in the red spectrum. This information is useful in the instances where intramuscular injections are to be given with drugs whose 'Full Prescribing Information' instructs the patient to aspirate and check for blood in the syringe which indicates that the puncture of a vein has occurred, and if so detected, to abort the injection and then re-inject into a different location.

BACKGROUND OF THE INVENTION

Conventional syringes have been in medical use for over a hundred years to inject medicaments into the body. These devices have protocols described in the literature for their general use and their specific use with a vast plethora of injectable drugs. Primarily supplied in two formats; empty syringes for filling from a vial of the drug, or as a pre-filled syringe. The conventional syringe is the most widely known and understood of the injection devices. Who hasn't seen a conventional syringe injection performed in the movies at least? The point being that syringe injections are familiar and therefore, lack a "fear-of-the-unknown" aspect even though the patient may be afraid of injections themselves. In contrast, the so-called "autoinjectors and other newer and sometimes "automated" medicament injection devices are unknown to the general population. An increasing segment of the population however, is finding themselves in need of receiving injections or giving injections and need assistance such as cannot be provided by the plain syringe presentation. Receiving injections can be frightening and receiving injections from an unknown device which, by all appearances, will lack bedside manner and gentleness, can further compound injection anxiety beyond that which may be experienced from the familiar. In the hands of a skillful operator, a conventional syringe injection can be gentle and non-frightening, especially if the one receiving the injection doesn't have to watch. If the one giving the injection is the one receiving the injection, not looking while they perform the injection is not an option, at least when using a conventional syringe by itself. Also, syringes require a degree of dexterity and technique to administer.

Considering the non-conventional (non-syringe presentation) types of medicament injection devices, be they automated or not so, their unknown or mysterious and non-obvious nature of their operation can cause the one giving an injection to question how the mechanism works and to hesitate or feel unsure they are proceeding correctly. To actuate such a medicament delivery device, such as an autoinjector, the user may be required to execute a series of operations that they have never even seen performed. For example, to actuate some known autoinjectors, the user must remove a protective cap, remove the locking device, place the injector properly against the body, and then press a button to actuate the device, and finally, hold the device in place on the body for a certain amount of time in order to completely dispense the drug before the needle is withdrawn from the tissue. These steps are not necessarily any more difficult than giving an injection with a conventional syringe, however, the steps may be unknown or unfamiliar or in question. Besides the possible increased anxiety or hesitancy presented by the unknown, there is also a greater possibility of improper use. For example, since with these injector devices, you cannot see the emptying of the medicament from its container, there is the possibility of removal of the needle too soon from the tissue before the full required dosage of the drug has been administered.

The likelihood of improper use of known medicament delivery devices can be compounded by the nature of the user and/or the circumstances under which such devices are used. For example, many users are not trained medical professionals and may have never been trained in the operation of such devices. Moreover, in certain situations, the user may not be the patient, and may therefore have no experience with the medicament delivery device.

Some known medicament delivery devices include printed instructions to inform the user of the steps required to properly deliver the medicament. Such printed instructions, however, can be inadequate in a society which "reads the instructions as a last resort." Moreover, because some known medicament delivery devices, such as for example, autoinjectors and pen injectors or the like can be compact, such printed instructions may be too small to read and comprehend. If the instructions are printed on paper, the instructions can become separated from the device.

Some known medicament delivery devices can produce sounds, such as a beep or tones that can be provided as prompts to users of medicament delivery devices. The sounds of such known devices and the manner in which the sounds are produced, however, provide limited information to the user or the user may not know what the "tone" emitted means. For example, some known medicament delivery devices produce a single tone sound or LED light going off to indicate that a proper dosage has been delivered, but cannot provide a user with instructions associated with the use of the device or directions in a step-by-step presentation. One known device has attempted to remedy this lack of instructional feedback by providing synthesized voice instructions, yet such a voice system as they illustrate is only sixty seconds of synthesized voice. Furthermore, there are patients speaking many native languages. Synthesized voice may not be easily understandable, especially if the quality is lacking. The sound level and/or the quality of the sound produced by such known medicament delivery devices is limited by the size, performance, and/or cost associated with sophisticated human language synthesizing systems, especially in one-time usage devices. Furthermore, synthesized voice systems can not equal the quality of a recorded actual human language spoken by a native of that language.

Thus, a need exists for medicament delivery systems and/or devices that provide instructions, messages, information and/or directions by an actual professional orator speaking in a calm and clear voice of a multitude of languages. Furthermore, biofeedback in the form of a varying tonal frequency and/or haptic vibration frequency could provide information as to how the injector was being held against the skin, such as the perpendicularity to the surface and the steadiness of its position. This could then allow for user initiation of the injection without actually watching the device.

The injector group which operates on cartridges as the medicament container often provides the benefit of multi-dose usage from the cartridge by replacing the needle between injections (such as insulin pens). To this inventor's knowledge, these devices only work with needles which are only of size and length for subcutaneous use. However, many drugs are not available in cartridges but rather, are provided in vials for use with standard syringes, or are contained within pre-filled syringes primarily made of glass. Also, many drugs require intramuscular injection which necessitates longer and larger gauge needles which are not accommodated by the known devices. These devices do provide for automated dispensing of "dialed in" quantities of medicament, yet they often do little to alleviate needle phobia as experienced by a large portion of the population. That is, most of these devices do provide dosage injection automation, yet do not automate the insertion or removal of the needle into or from the patient. Some of the known devices could be used on multiple patients (since the needle is changed between injections) but such devices are generally not intended for such use since they provide multiple dosing from a single cartridge (such as insulin) and thus, they become personal medicament dosing devices.

Thus, there is a need for injection devices which can use longer and larger gauge needles than are used with subcutaneous injections. Further, there is need for a reusable device which can work with drugs contained in vials for use with standard syringes or with pre-filled syringes; a standard presentation for which the largest number of drugs are available. Further, there is need for automated insertion and removal of the needle without being observable by the user or requiring user intervention. Further, there is need for an automated injection device which can be utilized in professional settings on multiple patients.

The jet injectors can provide for use among multiple patients because their jet can be delivered through a disposable jet tip or nozzle. This nozzle is what touches the patient and it can be provided sterile and then disposed after each injection. Further, the disposable nozzle has no needle, and therefore, there is no chance of "needle stick" which has become a large concern in the professional settings where many injections are given by a practitioner thus raising their chance of the occurrence. Therefore, the disposable nozzle provides for jet injector use in professional settings such as clinics and hospitals where multiple patients can be injected from the same reusable injector. However, for drugs to be administered in these settings with a "jet-injector", they must be approved for injection by jet (as opposed to needles) and the majority of drugs are not approved for this mode of application. Furthermore, jet injecting can introduce trauma to the tissue and are therefore, not less painful than needle injections. Jet injectors are powered by strong springs or compressed gas.

Thus, there exists a need for an injection device which can be used on multiple patients using standard needles which provide both sterility between patients and also protect against accidental needle stick when the injection is complete and the needle is being disposed. Further, there is need for the above facilities which can be administered through standard needles for which the vast majority of drugs are approved.

The "Auto-injector", so named since it is primarily intended for patient self-injection, or since they do provide some automation such as insertion of the needle into the patient's tissue, is spring or gas pressure powered and usually intended for disposal after one injection. A very few of these devices will operate a standard syringe, yet to this inventor's knowledge, not one of them has electronics as the power source which performs the injection via a standard syringe presentation. They have generally become increasingly more mechanically complicated in design, utilizing multiple springs to inject, and then retract the needle, etc.

There comes a limit to what can be accomplished by springs in a practical design. For instance, one could not maintain a real-time clock calendar with injection reminder alarms of mp3 audio ringtones by using springs. Likewise, it becomes increasingly difficult to control injection forces, velocities, and accelerations with springs. Sensing of injector position or angle against the skin are another example of the limit incurred by spring powered or operated devices. Still another consequence of spring or gas power is the sudden release of potential energy as these devices are triggered. Most all of the patent texts for these devices include the words: "cocking", "arming", "firing", or "firing mechanism" in phrases describing the storage or release of energy from the compressed springs or gas. These devices lack the ability to perform an injection with finesse such as can be administered by a well practiced medical professional. When the spring's energy is released to insert the needle and inject the medication, abruptness and vibration can occur as the spring's stored energy is released. Furthermore, the ability to adapt the action of the spring's force to accommodate varying forces presented by differences in liquid medication viscosities, needle gauges, and plunger forces are non-existent or would require a mechanical adjustment by the user.

Thus, there is a need for a reusable type autoinjector which can operate on a standard syringe presentation. Furthermore, there is need for an autoinjector which is mechanically simple yet contains electronics which can provide benefits not obtainable from springs or compressed gas. Further, there is need for finesse in inserting the needle, dispensing the medicament into the tissue, and removal of the needle such as can be provided with motion control algorithms and systems which can adjust to varying loads such as can be found in robotic systems. Further, there is need for sensing if and how the injector is placed against the skin, to make sure it is perpendicular to the surface, and held steady even if it is being held by the patient into an area outside of their visual range, such as in the gluteus muscle.

DESCRIPTION OF PRIOR RELATED ART

To illustrate the prior art and its limitations, the following examples will point out features and shortcomings of these aforementioned injector types by discussing specific examples from the patent record. Each of these devices has, limitations, deficiencies, or disadvantages, as will be apparent in view of the following detailed description of two embodiments of the present invention.

An example of the injectors which work by dispensing medicament from a cartridge is described by U.S. Pat. No. 6,942,646 B2, Sep. 13, 2005, Langley et al. As described in this patent, the injector is electronic and uses an electrically powered motor to push or move a plunger which operates on the cartridge's movable bung to dispense the medicament.

One can readily see that with this device, the patient has to manually insert the needle into their tissue and remove the needle after the injection. There is a significant percentage of the population which has needle phobia and experience feelings of disgust at seeing the needle inserted into or being removed from their bodies. These negative experiences can cause the patient to experience anxiety at the thought of having to receive their injection and thus, a portion of these patients will put off the injection to avoid the experience. This then results in non-compliance with treatment regimens and medical requirements.

This device illustrates operation on a cartridge which contains the medicament. This design restricts its use to medicaments that are available in cartridges. Since the majority of injectables are available in vials or prefilled syringes, the usability of the device is therefore limited to medicaments available in cartridges. Insulin is the obvious large exception to this observation, yet insulin is also available in vials for use with standard syringes.

The description states that the display can indicate for the patient to wait while the medicament is being delivered and then when the waiting period is up. For the patient to use this feature, the patient has to be in visual contact with the unit's display. This implies that the injection must occur on a bodily position in which the injector can be held so that the display screen is visually readable and so this restricts the possible injection sites that this device can be used on.

The patent claims the electronic control unit calculating amounts of medicament remaining in the cartridge and calculating partial dosages and amounts dispensed but does not offer the means for calculating such values. What is mentioned in the description is of controlling the motor by use of an end-stop switch for plunger retraction, the bung encountered position with a plunger mounted dome switch, and a one-bit encoder to detect slipping of the motor in cases of higher than normal loads, but no descriptive explanation is presented for how it is to keep track of amounts dispensed. Additionally, the description refers to detecting the needle being clogged and the motor running slower if the medicament is cold (and thus more viscous) and of being able to control the dosage speed for patient comfort, but no means is offered for a method to discern the force from needle clog from the force for cold medicament, both of which results in slower motor speed. Then this presents a dilemma for the proffered control of motor speed for patient comfort, since no method is offered for controlling motor speed.

A similar patent is U.S. Pat. No. 6,913,591 B2, Jul. 5, 2005, Itoh et al. which describes an electronic injector which uses an electrically powered motor to move a plunger which operates on a cartridge's movable bung to dispense the medicament. As with the previous example, the patient has to manually insert the needle into their tissue and remove the needle after the injection. As explained, this is a significant drawback to patient acceptance and hence, to treatment compliance. In the description, it specifies the plunger driven by the motor and moving between a forward limit switch and a return limit switch. Although the claims describe residual medicament calculations by the microprocessor, no method for obtaining the amount dispensed data is proffered. According to its description, the injector can only dispense one volume; that obtained by moving the bung from its starting position to a fixed end-of-travel limit switch. Furthermore, it describes connection to a personal computer through a "port" with nothing explaining how this port works. Furthermore, it describes detecting the occurrence of a clogged needle with alarm to the patient by using a strain gauge or load cell or velocity change, but no circuitry or means are illustrated to detect force or velocity. Furthermore, even if data of a change in the motor's force or velocity were obtained somehow, there is no explanation of how this data would be differentiated from a change in force or velocity due to different drug viscosities or needle gauges through which the medicament has to be extruded.

This device also illustrates operation on a cartridge containing the medicament. This restricts its use to medicaments that are available in cartridges. Since the majority of injectables are available in vials or prefilled syringes, the usability of the device is therefore limited to medicaments available in cartridges.

Another patent illustrating an electronic injector which uses an electrically powered motor to move a plunger which operates on a cartridge's movable bung to dispense the medicament is U.S. Pat. No. 7,967,784 B2, Jun. 28, 2011, Pongpariochana et al. As typical with cartridge based injectors, this device is only applicable to subcutaneous injections due to the limitations of the needles which can be attached to cartridges. In contrast to the above mentioned patents, this patent also describes the ability to insert the needle and remove the needle from the patient by use of a second electric motor which moves the cartridge/needle combination axially toward the opening in the housing. It further describes a "skin sensor" to detect contact of the device with the patient's skin, but no supporting circuitry or technique is provided. Likewise, it describes the user being able to control the dose for injection, the speed at which the needle penetrates the patient's skin, medication delivery speed, and injection depth, yet no means are offered or illustrated as to how these tasks are accomplished. It further describes the transfer of data to a personal computer in order that the doctor can monitor patient compliance, but no means other than stating the use of a "port; known per se" to accomplish this task, however, these functions are not part of the claims. Another concern is that an adapter or a needle-box is required to remove the needle from the cartridge.

An interesting variant of the cartridge type injector is patent application Ser. No. 12/180,708 (Pub. No. US 2010/0022963 A1) which uses compressed gas to effect movement for the purpose of needle insertion and dispensation of medicament yet it provides an electronic circuit to drive an audio speaker and perform simple input/output control. This injector is a one-time use (disposable) injector and lacks features such feedback to the dexterity challenged via skin sense technology coupled to audio feedback. Further, the act of insertion and withdrawal of the needle is without any form of distraction. They illustrate an audio processor which is capable of 60 seconds of speech synthesis at 7-bit output resolution. Although they illustrate and claim greater than 61 db at 20 feet by providing an acoustic cavity as part of the device housing, 7-bit voice synthesis, especially without an amplifier as they promote, is rather low quality and not readily adaptable to a multitude of languages no matter what the sound level. Although the application repeatedly cites the output being recorded speech, the illustrated audio processor is speech synthesis, not recorded audio. Also, the device is useful only for the drug/cartridge combinations assembled with the unit. This limits use only with drugs which have been previously assembled into the device at the time of manufacture and hence require greater regulatory aspects that are incurred with such an arrangement.

Another patent utilizing voice synthesis is U.S. Pat. No. 7,201,741 B2, Apr. 10, 2007, Marie wherein synthesized voice is used to announce the dosage numbers that are being dialed into the device by a rotating knob. Further, it states that the voice can be used to announce alarms and error states of the injector using the synthesized voice. However, no means are offered as to how the voice is to be synthesized. Further, it claims a PC interface for inputting and/or outputting data to or from said dosing device. Again, no means are offered as to how this is to be accomplished. Further, it claims an output device which produces optical or tactile signals, but no means are provided.

U.S. Pat. No. 7,713,229 B2, May 11, 2010, Veit et al., describes a glucose meter used in conjunction with insulin pens wherein the user inputs their insulin data and it is transmitted to another device such as a personal computer, but no actual means for transmitting it are demonstrated. The intention of the transmitter is to establish a data record on another device.

Patent application Ser. No. 10/347,702 (Pub. N. US 2004/0087903 A1, May 6, 2004, Veasey et al., illustrate a lead screw system with flats pushing the bung of a medicament cartridge and claim a dial dose mechanism by which a user may determine a required dose of medicament to be dispensed and an electronic control unit for controlling the operation of the drive mechanism in response to the dial dosage, but no supporting means are provided for this operation or means. Furthermore, this device requires the user to manually insert the needle and remove it from the patient. Therefore, this leaves this device lacking for the great many patients who could mix using a standard syringe, yet cannot bring themselves to inject themselves or even if they could, would not possess the skill to do it with finesse.

Likewise, U.S. Pat. No. 7,322,955 B2 requires manual insertion and removal of the needle into and from the patient. It claims to signal (sound) the user a variable amount after the end of the injection depending on the volume of the injection. Why this is even useful is questionable. It states "The sounder may conveniently comprise a simple tone emitter or a speech synthesizer." yet no means are provided for demonstrating actualization of either functions.

It seems to be a trend of the patents examined, that a usable feature may be expounded and some mechanical detail of how the feature it is to be accomplished is provided, but wherein motion control, electronics, digital communication and sensor technology, personal computer interface and most any function which isn't strictly mechanical are described and claimed, they are done so by mention only without providing any utilizable means with which to construct or embody such functions or features.

U.S. Pat. No. 6,042,571, Mar. 28, 2000, Hjertman et al. describes a device which is made to work on multi-chamber cartridges such as would contain lyophilized drug in one compartment and water-for-injection in the other. Mechanics are described as to what the device is to do, but suitable means that can enable the fabrication of the device are lacking. Regardless, the automatic mixing of contents as supplied in multi-compartment compartments is a worthy invention. However, there are lacking sufficient means as to how forces, velocities as described are to be controlled, or how positional data for the pusher rod is to be collected or communicated as is would be needed for volume calculations. Also the means which by the cartridge is to be "gripped" is left without demonstrated means. Additionally, there is no automation provided for inserting the needle or removing it from the patient's tissue in an automated fashion. Therefore, this leaves this device lacking for the great many patients who could mix lyophilized power in a vial with water-for-injection using a standard syringe, yet cannot bring themselves to inject themselves or even if they could, would not possess the skill or dexterity to do it with finesse. All the other features which may be realized by such devices will not be useful if the patient or user cannot accomplish the insertion of the needle into the flesh and operate the device.

U.S. Pat. No. 6,893,415 B2 describes an electronic insulin pen wherein the dosage is delivered by an electronic motor driving a rotating nut on a rotationally fixed lead screw. This device describes using a dc current circuit to sense when the pen is in the hand of the user. It teaches that if the user is disturbed after the size of the dose has been set, and leaves the medication delivery device unattended (not in the hand which provides a conductive path) the electronic control unit detects the absence of the dc current signal from the sensor and so immobilizes the start button and resets the set dose to prevent accidental injection by anyone other than the user. The means provided to accomplish detection of being in the user's hand by absence or presence of a dc current is provided by citing two separate patents for this purported purpose.

Injection devices based on a separate housing and replaceable cartridges have found use in many areas, such as medical delivery systems owing to the flexibility and economy contained in the possibility of providing the reusable housing with more or less advanced machinery for dosing and monitoring the injection procedure. In more permanent set-ups, e.g. for hospital treatment situations, there are few design restrictions and more expensive and highly sophisticated motorized manipulation means, processor controlled operation and data collection as well as possible interfacing with other available data collection and storage means would easily be justified by the continued reuse of the housing with accompanying mechanics and electronics. Yet these devices are limited to use by the of the drug's availability in a cartridge. Alternatively, infusion pumps which can operate on standard syringes utilize a catheter to convey the medicament into the patient who has been prepared with an intravenous hypodermic needle and are more suitable for long term gradual dosing. Some infusion pumps have been designed for ambulatory usage such as seen in U.S. Pat. No. 5,106,375, Apr. 21, 1992, Conero, U.S. Pat. No. 4,529,401, Jul. 16, 1985, Leslie et al., U.S. Pat. No. 5,139,484, Aug. 18, 1992, Hazon et al., and U.S. Pat. No. 4,833,384, May 23, 1989, Munro et al. Generally, these devices are either only suited in permanent installations or, when suggested for mobile use, are ungainly with low syringe to overall size ratio. They all lack the ability to insert and remove the hypodermic needle from the patient in a self contained unit and are essentially, still infusion pumps requiring catheters to convey the medicament.

For ambulatory purposes, the design limitations are more severe, especially for self-contained devices without connectable support to power or other functions which need to be internalized in a self-contained unit. Size and weight restrictions have previously placed limitations on the number and sophistication degree of functions possible to include. Automation has an alternative measure for increasing safety and avoiding misuse is similarly restricted by the added motorized means and operation repertoire by limited capacity of energy storage means.

Yet the devices have to meet all regular safety and precision aspects not only in the dosing step itself, but should exhibit the ability to insert and remove the hypodermic needle from the tissue with ease even for patients who are needle phobic or dexterity challenged. The problems become more pronounced with pharmaceuticals which are shear-sensitive and require dosing under controlled mechanical conditions.

Although handy and portable injectors may be devised with the minimum of support features necessary to safely control all the above said requirements and problems in the hands of a skilled operator, a general trend in long-term medication is to place the administration responsibility on the patient himself. A high degree of automation and control is then desirable to avoid mistakes and even to enable them to actually inject themselves without undue fear or phobia.

Patients dependent on frequent administrations also have a legitimate need for convenience and devices discrete enough to be brought around in daily life. The contradictory requirements on highly sophisticated and yet small and convenient devices are not met by known prior art suggestions. Accordingly, there is a continuing need for portable injection devices relieving patients under self-administration from the burden of learning and controlling in a fail-safe manner every step in the injection scheme, preferably by building a high degree of automation into the devices, while still satisfying the patients legitimate desire for easy to use and discrete design. Additionally, there is a continuing need for portable injection devices that are able to dispense a wide choice of medicaments by operating on a wide variety of standard fillable or pre-filled syringes. Although the present invention has a more general utility, it will mainly be described against this background.

So called "jet-injectors" and "auto-injectors" will be described here below in a brief manner since they are not usually electronic devices such as the present invention. Yet they will be described against the background of some functions in common or similar with the present invention or their lack of suitable means or abilities which are exhibited in such devices.

Many examples in the patent record for jet injectors are mechanically powered and do not provide for sterile replaceable and disposable jet tips/ampules are not represented here below because they have little bearing on the present invention. Instead, the jet injectors in the patent record which do have replaceable and disposable jet tips/ampules will be outlined briefly as a reference and comparison to the replaceable and disposable needle shield of the present invention. Other than replaceable and disposable injection means, jet injectors and the present invention have little in common.

U.S. Pat. No. 5,505,697, Apr. 9, 1996, McKinnon, Jr. et al. is an example of a jet injector which has the ampule and plunger are provided in a sterile "peel-pack" which is screwed onto the injector housing and then can be discarded after the injection. This device is unique among jet injectors in that it is powered by a servo motor driving a rotating ball-nut to drive a lead screw that drives the plunger. The device also discloses a capability for controlled pressure during the delivery phase. However, the brushless servo motor and optical encoder disclosed by their design would result in a premium price for this type of technology. The present invention accomplishes motion control capability without this type of expense. As sophisticated as this device is in providing controlled jet injections, it lacks in user interface, positional biofeedback, and audio capability such as musical distraction, ringtone reminder timers, and human spoken language.

U.S. Pat. No. 6,648,850 B2, Nov. 18, 2003, Landau, also describes a jet injector with a disposable cylinder and piston, the cylinder comprising a jet nozzle at the end. In one embodiment, the amount of medicament drawn into the cylinder is measured electronically by a type of linear optical encoder and displayed for the user. Unfortunately, this is about the extent of the electronics. The device is gas powered and the only other feature mentioned was a timed automatic turn-off of the device.

Patent application Ser. No. 10/143,475 (Pub. No. US 2002/0188251 A1) discloses a jet injector with disposable injection cartridges, however, these cartridges have to be prefilled and sealed at the factory. This involves extra regulatory requirements and limits the flexibility and utility of the device.

U.S. Pat. No. 7,699,802 B2, Apr. 20, 2010, Steinway et al., describes a spring powered jet injector which utilizes disposable vial with integral jet nozzle which the user can fill with the medicament of their choice. The device requires a separate spring cocking station which renders the device nearly non-ambulatory. In other words, it lends itself to home or professional facilities. As pointed out earlier, for pharmaceuticals to be used in a jet injector in professional settings, they must be approved for jet injection. The vast majority of medicaments are not approved for jet injection, and this further restricts the use of the device. Additionally, the words used to describe the spring's state and mode of action are "trigger", "spring-powered ram", "cocked position", and "firing position". This terminology provides an indication of the devices action which can be disconcerting to the patient.

U.S. Pat. No. 5,704,911 describes a patent similar to the Steinway '802 patent in that it works with a user fillable ampule assembly having a chamber for holding liquid medication and that the system also includes a cocking station which automatically cocks the injector device. Again, pharmaceuticals must be approved for jet injection which limits the use of jet injectors to such drugs. Additionally, the separate cocking/carrying case makes the device somewhat large to take with you.

The last category is the so called auto-injectors. These are primarily mechanical in nature. Some are entirely disposable, some work with ampules or glass syringes, and a very few works with standard syringes with removable needles.

Patent application PCT/GB09/51016 (Pub. No. US 2011/0144584) assigned to Owen Mumford Ltd. describes a spring powered autoinjector which works on a syringe. No qualifications are provided for what syringe or syringes the device can operate on. It does illustrate loading the syringe in a horizontal method which they characterize as loading into a drawer. As in a previous patent assigned to Owen Mumford (U.S. Pat. No. 5,599,309), the syringe with accompanying needle is pushed into the tissue by pushing on the syringe plunger. Thus, it is dispensing the drug as the needle is entering the skin and the drug could be distributed in various strata instead of all at the necessary depth. The patent does not disclose any information concerning what needles may be utilized either. It does provide multiple noses to adjust the penetration depth. Therefore, if it accommodates various needle lengths, the patient could be confused at which depth they will get with a particular nose since the depth now requires an adjustment calculation for the variable length of needle attached.

Like most spring loaded autoinjector, descriptive words in the disclosure utilize such phrases as "push down to fire" which provides a clue as to the mode of operation. It does describe automatic insertion of the needle and then its withdrawal back into a protective shroud. However, all-in-all, it is still a crude, mechanically complex spring powered injector with no capability of injection finesse or any of the benefits that electronics can provide.

U.S. Pat. No. 8,038,649 B2, Oct. 18, 2011, Kronestedt, describes a mechanical spring powered autoinjector whose spiral wound powers a threaded plunger rod which gives it mechanical advantage to pump higher viscous materials from a medicament container through the hypodermic needle. The device features automatic penetration of the needle, automatic injection and automatic safety means for preventing accidental needle sticks. However, the device is restricted to working with a syringe housing which fits their holder and which has a stopper which works with their threaded plunger rod. Thus, the device is restricted to factory filling and one time use.

Patent application Ser. No. 12/096,675 (Pub. No. US 2010/0010454 A1) is similar in that it provides for needle insertion, automatic injection and automatic safety means for preventing accidental needle sticks. The device further states that it can accommodate containers (syringes) of different sizes or shape, yet these different syringes require a threaded plunger rod and thus, are custom syringes. In other words, the device is restricted to factory filling into a selection of custom syringes and one time use. The device is mechanically complicated and wasteful when you consider that it is used once and then disposed of.

Devices which utilize a custom designed or non-standard medicament chamber rather than being built around a standard pre-filled syringe presentation means that the device as a whole must be subjected to more rigorous regulatory control as compared with a device containing a standard pre-filled syringe presentation which will have already obtained regulatory approval. Indeed, there is a significant commercial advantage in being able to use a standard pre-filled syringe, which will have been subjected to numerous clinical trials, drug stability studies, and regulatory approval. Any modification to the standard syringe may require further trials and approval, adding delay and expense.

Patent application Ser. No. 12/161,776 (Pub. No. US 2010/0152655 A1) Jun. 17, 2010, Stamp, describes an autoinjector which can be loaded with a standard prefilled syringe. Although it will accept standard pre-filled syringes, it can only do so by matching the internal diameter of the syringe holder with the outside diameter of the pre-filled syringe. Therefore, the injector must be matched to the particular pre-filled syringe to fit and operate correctly. This autoinjector retracts the needle after injection. Unlike other autoinjectors which retract the needle, this device supports the syringe at its distal end by an innovative mechanism that allows the needle shield to pass the supportive surface. This method of support is supposed to provide better protection from breakage of glass pre-filled syringes. Their text states that there is a risk of the needle being damaged during assembly and that they solve the problem by providing a viewing window. It isn't evident how viewing can prevent damage during assembly or how to spot the damage to the needle inside a shield. Further, this is a one-time device and it is disposed after the injection. Further, the device is without feedback (other than the window) to the user as to orientation or features as can be provided by electronics such as audio queues.

Patent application Ser. No. 12/988,298 (Pub. No. US 2011/0178501 A1) is essentially the same as the above '776 by Stamp, but provides for user control over the length of time the needle remains in the tissue after the injection of medicament is complete by essentially holding it in place for an amount of time as desired. The needle is retracted when the user stops holding the injector against the skin by a force depending on the embodiment.

U.S. Pat. No. 6,203,530 B1 describes a mechanical spring powered autoinjector which mounts a standard medical syringe and provides adjustment of injection depth. It also describes a mechanical method to remove the needle's protective cap when the device is cocked and the syringe is withdrawn into the barrel. This patent describes a window to see if the device is cocked or not. This patent illustrates the syringe with accompanying needle being pushed into the tissue by pushing on the syringe plunger. Thus, it is dispensing the drug as the needle is entering the skin and the drug could be distributed in various strata instead of all at the necessary depth.

U.S. Pat. No. 6,203,530 B1, Mar. 20, 2001, Stewart, Sr., teaches a spring powered autoinjector that accepts a standard syringe. There are a wide variety of "standard" syringes and the patent isn't specific of which kinds. The device contains a trigger for releasing the spring and performing the injection which the user must push along the surface of the barrel and then through the trigger access to overcome the resilient arm and move the notch to release the catch. Further, it provides a slot for receiving a button to permit exposure of the needle to remove the protective cap when the device is cocked. These actions require manual dexterity and so this device will be hard to operate for the dexterity challenged. Further, the device has to be cocked and then screwed together. Again, dexterity challenging operations. As in some patents mentioned above, the device's drive mechanism pushes on the syringe plunger in order to insert the needle onto the patient's tissue. Therefore, as the drive pushes, the medicament is being dispensed as the needle is inserted into the tissue. This presents the possibility that not all the medicament will be delivered to the full depth of the needle penetration. Further, after the injection, the user has to manually remove the needle from the tissue. This can be disconcerting to the patient to see the needle being pulled from their body. The patent fails to elaborate on what length of needle is accommodated by the device. Finally, it is a manual device with a sudden release of energy which can be disconcerting to patients resulting in anxiety over the injection. If it is to be used by the patient on themselves, they may not perform the injection due to avoidance behavior.

Each of these devices has, limitations, deficiencies, or disadvantages, as will be apparent in view of the following detailed description of two embodiments of the present invention.

SUMMARY OF THE INVENTION

The present invention relates generally to a durable, portable, multiple-use injector, and to methods of its making, operation, and use. A main object of the present invention is to avoid or ameliorate the above said disadvantages of known devices and to provide new novel features which will aid the user and comfort the patient by means that have not been addressed by known devices. A further object is to offer a device facilitating operation and reducing risks for and hazards in possible misuse. Still another object is to offer a device suitable for automation and motorized operation. Yet another object is to provide such a device with improved possibilities for self-control. A further object is to provide a device facilitating orientation and initiation. Another object is to provide such a device suitable for producing the least amount of anxiety toward its use such as experienced by the needle phobic. Yet another object is to provide such a device suitable for the dexterity challenged. Yet another object is to provide such a device suitable for providing a likeness of bedside manner as would be experienced by receiving an injection given by a physician. Yet another object is to provide nurses, physicians and caregivers who may use the device, with a means of removing the syringe and needle from the sight of the patient and provide a less threatening presentation and action to the patient in order to relax the patient and provide a less anxiety provoking experience. Yet another object is to provide a more safe and patient friendly method of administering needle injections by the medical community. Yet another object is to provide such a device which assists the user in maintaining a set schedule of injections. Yet another object is to reduce the pain caused by needle penetration into live tissue. Yet another object is to determine if the needle has penetrated into a vein. Yet another object of this invention is to provide such an electronic injector in which the device is particularly efficient and elegant with respect to the design, functionality, and material utilization of components of the device. In other words, the parts count of the device is small compared to the functionality, and the materials are utilized with ease and reduce the cost of manufacturing of the device.

These objects are reached with the characteristics and improvements set forth in the appended claims.

According to one aspect of the invention, a device of the initially stated type has a housing which can be held in the hand. The injector being illustrated accommodates standard syringes which are equipped with removable needles or which have molded-in needles such are found with glass syringes which are often used for pre-filling with a medicament. A syringe is inserted into the housing by opening a lid on the top of the injector and placing the syringe into the housing in a horizontal fashion with the needle inserted into a guide and the finger flange pressed into an elastomeric gripper. Then the lid is closed. The injector can be switched on or it could already be on and in sleep-mode.

In the proximal end of the housing are electronics consisting of two gear motors directly connected to lead screws, an integrated circuit board, and connectors to peripheral electronics such as the display and keypad, and an audio speaker. One of the motors drives a lead screw which moves a carriage within the housing in a linear fashion forward and rearward. The carriage contains the elastomeric grip which holds the finger flange of the syringe. When the carriage is moved forward (distally) the syringe needle exits the housing at the far forward (distal) surface into the patient's tissue. The other motor is mounted to the carriage and pushes on the syringe plunger thumb pad to discharge the medicament once the needle is inserted into the patient. Then the carriage is withdrawn rearward and thus the needle is removed from the patient and retracted back into the device.

In the distal end of the housing are contained the battery, haptic motor, initiate button, sensors, and depending upon the embodiment, either a syringe guide or a removable/disposable needle shield which contains a needle guide.

On the distal end of the housing is a surface for being held against the patient's skin at the site of injection. This outside of this surface contains sensors which provide information as to the pressure and angle and steadiness with which the injector is being held against the patient's skin. This information is provided back to the patient as biofeedback by a variable frequency haptic motor and an audio speaker which can reproduce tonal information, ringtones, or spoken human language.

Joining the distal and proximal portions of the injector is a folding hinge which permits the injector to be folded in half for a more compact and therefore a more discrete and transportable device.

The injector is equipped with sensor technology to sense contact with the skin, the angle of contact, and the steadiness of such contact. The injector is further equipped with sensors used for safety concerns such as the lid being closed and the hinge being locked into operating position. The injector can optionally be equipped with sensor technology to detect if the needle has penetrated a blood vein by accident.

The injector is further equipped with biofeedback which lets the operator know how they are holding the device against the patient, the different stages of injection with audio queues, and human spoken language for patient/operator instructions, device status, alerts or errors, and bedside mannerisms as would be conveyed by a skilled physician.

DETAILED DESCRIPTION OF THE INVENTION

Throughout the description and claims of this specification, the words "comprise" and "contain" and variations of the words, for example "comprising" and "comprises", means "including but not limited to", and is not intended to (and does not) exclude other components, integers or steps.

The principles of the present invention may be used for injection devices or systems in broad terms for any type of chemicals, compositions or preparations delivered for any purpose. The invention has been developed mainly in view of applications for medical preparations and for convenience the invention will be described in terms of this use. In these applications an infusion channel or conducting means may be a tube or catheter, a needle or cannula or a needle-less system based on liquid jet. Hereinafter, the conducting means shall be referred to as the "needle". The needle is affixed and fluidically in communication with material in a cartridge or cylinder or barrel of a syringe, hereinafter called the medicament cylinder or cylinder. Said cylinder shall contain a material to be ejectable through the needle by a displacement of the movable wall or bung or seal (hereinafter referred to as the seal) and any material fulfilling this requirement can be used. Normally the material is a fluid and preferably a liquid, including materials behaving as liquids such as emulsions or suspensions.

Throughout the description and claims of this specification, the singular encompasses the plural unless the context otherwise requires. In particular, where the indefinite article is used, the specification is to be understood as contemplating plurality as well as singularity, unless the context requires otherwise.

Throughout the following description, reference to a "forward" or "distal" direction means the direction which is towards the patient's injection site or their skin when the injection device is in use. The "forward" or "distal" end of the injector or any part in the injector is the end toward the patient's skin when the device is in use. Similarly, reference to a "rearward" or "proximal" direction means the direction which is away from the patient's skin and the "rearward" or "proximal" end of the injector or any part within the injector is the end furthest from the patient's skin when the injection device is in use.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The nature of medicament container content shall also be understood to include pharmaceuticals in broad terms and to embrace for example natural components and body fluids pre-filled or drawn into the cylinder, although most commonly the pharmaceutical is loaded by the user or factory prefilled into the cylinder. The invention gives particular advantages in connection with sensitive compounds susceptible to degradation or denaturation under mechanical stress such as high shear forces. Compounds of high molecular weight may be of this type, high molecular weight hormones, for example growth hormones. Additionally, the invention gives particular advantages in connection with high viscosity medicaments which may require higher forces or a limiting of such forces or a combination thereof for the best practice of injecting them in a safe and expedient manner.

The administration manner can also be varied within broad limits and may include entirely continuous infusion, continuous infusion with varying flow, or intermittent infusions or injections. Especially when combined with automation means to be further described below, the administration manner can easily be varied by adaptations by responsive software or by user control. The invention gives special benefits in intermittent administration in that the mechanical means of dispensation of medicament is accomplished by a motion control software/hardware system. Similarly the invention gives advantages, e.g. in positioning and initiation, in most administration manners also when only a single dosing operation is contemplated. Also, the invention gives special advantages when multiple patients need to be injected routinely by different medicaments with different syringes in settings such as a hospital, clinic, or physician office.

Parts and their Relationship:

The syringe, generally speaking, is a central cylinder which holds the medicament. At the proximal end or at some location along the cylinder, is a flange or means of fixing the cylinder against axial and perhaps rotational movement. The cylinder has attached at the distal end, a needle or cannula, etc. Inside the cylinder is a seal which if moved toward the distal end causes the contents of the cylinder to be expelled through the needle. Attached or pressing against this seal is a plunger rod. The syringe as such, is not part of the invention but rather, the object upon which the injector operates. Many so called standard syringes are made for general and specific use. General types of standard syringes may include a removable needle such as Luer type needles which have a slip or lock type fit onto the cylinder of the syringe. Other types of general standard syringes have needles which are permanent fixtures of the syringe. They are most often molded in but there can be other methods of permanently affixing the needle. Many pharmaceuticals are packaged as pre-filled syringes. This provides for a ready-to-use presentation. Often times, prefilled syringes are made of glass since the material is inert and provides a hermetic package for the medicament provided the seal is not breached. Seals may have special coatings provided on their surface to help lubricate their sliding action within the bore of the cylinder and also may have coatings to provide improved sealing qualities for long term storage. Often, seals will exhibit increased sticky friction when they are first pushed from their initial manufactured position within the cylinder. The plunger is often attached to the seal but in some instances, it is supplied separate and must be attached to the seal, often by screwing it into the seal.

The injector can be internally sized to accommodate a large variety of standard syringes by sizing the syringe support structure in accordance. For instance, a particular embodiment of the injector may be sized to accommodate standard one to three (1-3) ml (cc) syringe cylinders. Specifically, the internal support structure that holds the syringe and moves with it can be sized for the diameter and length of the cylinder and the type of needle attached whether it is a removable needle or a permanently fixed needle onto the cylinder. In particular, two embodiments of this invention are illustrated. One embodiment, hereinafter called the "syringe guide embodiment" is primarily made for prefilled syringes with permanently affixed needles. This embodiment has a syringe guide which is molded to accommodate a certain size of syringe and it holds the distal end of the syringe and sets the distance between the needle and the finger flange of the cylinder. The actual finger flange is supported by the elastomeric flange.grip which is not part of the syringe guide. This syringe guide can be changed out so that different syringes can be used with the same injector. Illustrated in this particular embodiment is a syringe guide for two major brands of 1 ml plastic syringes with removable needles of the Luer slip design. These syringes are known as Tuberculin syringes. A syringe guide could just as easily be made to accommodate a glass 1 ml Tuberculin syringe with molded in needle. Likewise, the syringe guide could just as easily be made to accommodate 3 ml plastic syringes with Luer lock needles. There are also a number of non-standard prefilled syringes as supplied by various pharmaceutical manufacturers. Many of these syringes can be accommodated as well by shaping the syringe guide appropriately. Some non-standard syringes have various features which preclude their use with the syringe guide as illustrated. For example, a common non-standard prefilled syringe has a removable needle which has a needle guard attached which swings in place to guard the needle after injection. This needle guard is not compatible with the illustrated embodiment. The design of the injector could be modified to accommodate the special needle with guard by for instance, widening the distal end of the injector, however, a more practical alternative would be to have the user change the needle with guard to a standard removable Luer needle and use a syringe guard which is made to accommodate such needles. The plunger rod which is illustrated in the embodiments pictured show a rod attached to the seal at the distal end of the rod and a circular thumb pad at the proximal end of the pad. This is the most common arrangement for a standard syringe either unfilled or prefilled. The thumb pad is not a requirement, however the most practical design would be to design the pushing mechanism to push against a thumb pad arrangement, or in special cases where aspiration is required, to pull on the thumb pad. Another embodiment of the invention, hereinafter referred to as the "removable/disposable needle shield embodiment" does not use a needle guide but rather is made specifically for removable needle syringes such as the popular Luer type needle/syringe combinations. Internal to the needle shield is a needle guide which holds the distal end of the syringe just as the syringe guide holds the needle end of the syringe. Specifically the needle guide holds the Luer fitting while the finger flange at the proximal end of the syringe cylinder is supported by elastomeric flange grip just as in the syringe guide embodiment. In effect, the two embodiments are arranged internally so that the vast majority of standard and non-standard syringes and prefilled syringes can be accommodated with little or no change to the internal structure.

The housing is an elongated structure designed for being hand held when giving an injection, or it could sit on a table or tray if performing a lengthy function such as providing an infusion. The structure is preferably fabricated principally of plastic polymers, and may be injection molded for economy of manufacture, although the invention is not so limited. The injector, when held in front of the user with the distal end to their left and the proximal end to their right presents the device to the user with the left side facing toward the user, the right side facing away from the user, and the top facing upward.

The housing is divided into two parts and so joined by a hinge on the bottom of the housing so that the injector folds roughly in half by unlatching connectors on the exterior sides of the housing and so folding the housing downward. Likewise, the housing is unfolded and straightened into one axial enclosure by swing the two hinged halves back together where they join together and become one continuous outside surface of the housing. The peripheral shell of the housing can be fitted with tongue and grooves so that when the two halves are unfolded and latched into a straight arrangement of the halves, the grove and tongues so mate and form a so functioning seamless shell or housing. The hinge is necessarily able to pass electrical conductors through it to enable electrical signals from various sensors, the battery and the haptic motor located in the distal portion of the housing to pass into the proximal portion of the housing where the integrated circuit board is located.

The top of the injector for a major portion of its length will have a lid that opens to allow insertion of the syringe. The lids shall be connected to the housing by hinges. These hinges shall bias the lids to spring open fully when opened past the half-way point or to spring closed when closed past the half-way point. Such hinges can be found in U.S. Pat. No. 4,993,772-Spring-loaded, dual-action hinge assembly for vehicle accessories. Since the device in the two embodiments illustrated is able to fold in half, there are necessarily two lids with this arrangement. The two lids when the device is not folded but in the straight position, are caused to interlock with one another so that they form one lid and move together. This interlocking of the lids could be accomplished by molding wedges at the interlocking edges of each lid so that mating wedges with opposite from the abutting lid mesh together thus preventing movement in one plane. The lids would be prevented from moving in the other two planes because of the hinges which hold the lids to the structure of the housing. Wedges are one method of interlocking the edges of the lids, yet other means could be employed, such as pegs with mating holes, both sets of holes and pegs being present on the edge of the lids at the interlocking interface.

The lid is to contain an electronic display to provide visual feedback of injector state, instructions, menu choices, and the like. The display could be placed on either lid but is most preferentially placed on the proximal lid since the injector when being held in the hand would be from the distal end and the hand could transfer dirt or lotion onto the display window thus occluding the visibility. The display would most preferentially be an OLED display (Organic Light Emitting Diode) type although it could be of another type such as LCD (Liquid Crystal Display). The display most preferentially would be the OLED type as it is most bright and doesn't require backlighting and can be viewed from a wider angle than other displays. The display could preferentially have the capability of displaying graphics or text. Most preferentially, the display would be a 128×32 pixel OLED display, but other matrix arrangements are possible such as 128×64 pixels.

On the lid is also optionally contained a surface for writing upon such as a white board area or other surface for writing upon such as the textured surface for writing with pencil. The white board is easier to erase but subject to smearing whereas the pencil board is less easily smudged but requires an eraser such as would be found on a pencil in order to erase the writing. The white board or pencil board could be inset into the lid or laminated upon the lid or the lid could be formed of the material. Preferentially, the writing board is far to the proximal end of the lid to avoid smudging when the hand grips the distal end of the housing. Or the writing board could be located above the display or it could be located to the right and above the display. The writing board could be used to keep track of what is loaded into the syringe or other details as might be useful. For instance, a nurse at their station may have a tray of injectors for making their rounds. They could load a syringe into an injector and then mark the name and number of the patient for which the injection is to be given.

A sensor on the housing specifically located at the edge of the housing opening where the lid meets the housing when closed is provided to sense the closure of the lid. This is to prevent operation of the device if the lid is not in the closed position. The sensors could be located in another area of the housing such as at the hinge area, however, the aforementioned area is most preferentially the best location because it is most sensitive to the angle of the lid. When sensing at the far edge of the lid, the lid must be completely closed to reach the sensor. The sensor for the lid can consist of a continuity circuit which a spring conductor affixed to the lid. When the lid is in the closed position, its affixed conductive spring completes the continuity circuit and thus provides a signal that the lid is closed. The continuity circuit is monitored by the "Micro Controller Unit" (MCU).

Similar to the lid closed continuity circuit, a hinge-straightened continuity circuit exists on the faces of the two halves of the housing which are brought together when the hinge is straightened. Specifically, a conductive spring can be affixed to a location at the upper edge of the lower compartment in the proximal portion of the housing and a continuity circuit can be supplied to a location at the upper edge of the lower compartment in the distal portion of the housing. Then, when the hinge is straightened and the two portions of the housing are brought together, the conductive spring completes the continuity circuit to provide a signal that the hinge is completely straightened. The continuity circuit is monitored by the MCU.

The distal end of the housing is composed of a cylinder or guide tube into which the needle and the distal portion of the syringe move forward and rearward. When the syringe is moved forward, the needle protrudes beyond the front face of the housing and therefore into the patient's tissue. When the syringe is moved rearward, it is retracted back inside the housing. The needle and distal portion of the syringe is so moved sliding coaxially with a mechanism which supports the front end of the syringe and so moves with the syringe as it is guiding the needle and moves with the needle and syringe. In the syringe guide embodiment, the syringe guide holds the front end of the syringe slides within this cylinder or guide tube and so guides the needle down the cylinder as the needle exits the front end of the housing. In the disposable needle shield embodiment the cylinder is the disposable needle shield and the front end of the syringe is held by a needle guide which resides and slides within the needle shield. Thus, as the syringe is moved forward, the needle guide slides within the needle shield and guides the syringe as the needle exits the front end of the housing and into the patient's tissue.

An injection initiate button is located on the forward portion of the housing in a location which is ergonomic to the hand so that the fore finger of either hand may press the button or the thumb of either hand may press the button or the little finger of either hand may press the button by reversing the side of the injector where the hand is placed. This may be accomplished with one button located on the right side of the distal portion of the housing or a button could be located on the right and lest sides of the distal portion of the housing, with either button being able to initiate an injection. The latter may assist users with left handedness operate the injector with more ease. Optionally, the button or buttons will be somewhat recessed to prevent inadvertent activation The injection initiate button can be any means with which to signal the MCU that an injection sequence is desired. Most appropriate would be a continuity circuit monitored by the MCU. The continuity can be completed by a conductive element; most preferred being a snap dome switch which, in addition to electrically completing the continuity of the circuit, also provides tactile feedback to the user that the button has been pressed.

On the bottom of the housing can be a battery access door in the event that the battery or batteries used to power the injector need to be replaceable. Most preferred is a single cell battery that is charged within the device and therefore, does not require removal and therefore does not require a battery access door. However, the batteries could be intended for recharging outside of the housing by a separate battery charger or batteries may be used that are not rechargeable but rather disposable. In these cases the battery access door is required. As the battery or batteries are contained within the bottom of the distal portion of the housing, the battery access door, if so needed, would be located on the bottom of the distal portion of the housing.

A speaker is located on the top of the housing to the right of the proximal lid on a cover that is flush with the lids. The speaker can be mounted underneath the cover so provided with a speaker grill molded into the cover to allow the sound to exit the housing.

A keypad is mounted on the left side of the proximal end of the housing. The keypad can be so located so that pressing its buttons would occur much the same way that texting is conducted on a cell phone. That is, the injector is held with both hands and in front of the user in a horizontal fashion with the distal end to their left. Then the buttons could be pressed with the thumb of either hand or the thumbs of both hands. Preferentially, there are only four buttons on the keypad: a up-menu button and an enter button on the top row, and left and right arrow buttons on the bottom row. The keypad is preferentially made with laminated membrane keypad technology so as to keep it as thin as possible. The signals of such technology are electrical continuity signals which are conveyed to the MCU by a flexible electric circuit which is part of the laminate layers of the membrane keypad. The flexible electric circuit is routed through the wall or shell of the housing to the integrated circuit board located in the proximal portion of the housing.

A micro USB connector is provided on the proximal end of the injector when the embodiment is so equipped with communication capabilities. When so provided, the injector is supplied with a micro USB cable and optionally, an AC wall adapter (so called wall cube) which can also accept the USB cable for AC charging capabilities.

An on/off switch is provided on the proximal end of the injector (not illustrated) which would be left in the "on" position if reminder alarms for an injection schedule are needed. When in the "on" position and after a period of inactivity, the injector goes into sleep mode which only uses a small amount of quiescent current to maintain the real-time clock-calendar which is necessary for the reminder alarm function. Otherwise, the injector can be switched "off".

The interior proximal portion of the housing contains a carriage slidably disposed within such that it can be moved either forward or rearward. The carriage is of a rectangular trough shape and is made of a material which easily slides against the inner wall of the housing. The carriage is equipped with an elastomeric syringe flange gripper contained within the distal end of the trough. The elastomeric syringe flange gripper contains rubbery fins into which the syringe is pressed. The fins have cutouts which allow the cylinder of the syringe to pass. Thus, the syringe's proximal end (or where the finger flange is located) is held from axial movement by the fins and from movement in the other (x and y) dimensions by the gripping action on the syringe cylinder. Different elastomeric grippers can be inserted into the carriage to accommodate different lengths of syringe cylinders and different diameters of syringe cylinders. Typically, four elastomeric inserts could accommodate the majority of syringes standard and prefilled up to 3 ml capacity. Two variations would have the fins shifted from one another. Said another way, one elastomer would have fins molded where the spaces between the fins are located in the other. Of these two fin placement variations, two variations of each to accommodate either 1 ml syringes or 3 ml syringes would bring the permutations to four and accommodate the majority of syringes available on the market for the greatest number of devices sold. Thus, when the carriage is in motion either forward or rearward, an axial force is applied to the syringe via its finger flanges as they rest between two sets of fins closely spaced together. The design contemplates that only the finger flange portion of the syringe cylinder needs to reside in the carriage. Requiring more of the syringe than necessary to be located within the carriage would of necessity, restrict the range of syringe cylinder lengths that could be accommodated. In fact, the median of cylinder lengths to be represented by any one embodiment of the invention should reside in the middle of the fins so provided in order to accommodate the widest variation in lengths of syringe cylinders. Typically, there would be either three or four fins in any elastomeric gripper design, with three fins providing two slots to capture the finger flange of various syringes and four fins providing three slots to capture the finger flange of various syringes in between those lengths accommodated by the three fin designs of flange grippers.

The plunger rod exiting from the proximal end of the syringe cylinder resides within the carriage. Mounted to the proximal outside of the carriage is an actuator motor. This motor is connected to a lead screw and nut on the inside of the carriage. The nut is connected to an actuator which pushes or pulls on the thumb pad at the end of the plunger rod. The lead nut and the actuator to which it is attached, is prevented from rotating by a slot running lengthwise (forward and rearward) on the inside of the carriage into which the actuator rides as the nut travels forward and rearward on the lead screw. In this manner, the actuator motor causes a force on the plunger rod. When dispensing medicament from the syringe cylinder, this force asserted by the actuator is distal. After the injection, the actuator motor can be reversed which would return the actuator to its initial proximal location. In the event that aspiration is provided by the embodiment, the plunger rod's thumb pad would be captive by the actuator. In such case, when the actuator motor is reversed, the syringe needle will aspirate the tissue so that the aspirate is drawn into the syringe cylinder and then can be measured by a sensor to determine the presence of blood.

In the course of dispensing the medicament from the syringe and in returning the actuator to its initial proximal position, the actuator motion is produced by the actuator motor which is under the control of the MCU and the speed is controlled by suitable electronic Pulse Width Modulation (PWM) drivers. The MCU causes the actuator to accelerate to a fixed travel speed and then as the length of the shortest plunger stroke the injector is designed for is approached, the MCU causes the actuator motor to decelerate to a slower speed and then when the end-of-travel is detected by a current sensor, the actuator motor is decelerated to a stop. This motion depresses the plunger or returns the actuator to its home position. This motion is referred to as a velocity profile and is under control of the MCU. Additional details will be explained further below.

A spring is so fixed on the actuator so that a forward force on the plunger rod by the actuator partially compresses the spring. This spring could be a piece of flat spring steel bent into a long U-shape so that one side of the U is attached to the actuator and the other side of the U presses against the thumb pad of the plunger rod. Or the spring steel could be shaped as flat S or other configurations. A coiled spring is not necessarily called for. When the syringe seal, which is connected to the plunger rod, reaches the distal end of the cylinder's bore, it can travel no further. However, the actuator motor is still rotating driving the actuator forward pushing on the plunger rod which then further compresses the spring. As the spring is compressed further and the force that is required causes an increase in the torque delivered by the motor. This torque is proportional to current which is monitored by the MCU executing an algorithm which detects the increase in torque decelerates the actuator motor to a stop. The actuator position is actually tracked by the software however, the torque sensing method of detecting end of travel is necessary since various standard and non-standard syringes have different plunger rod lengths. Therefore, even though the software is keeping track of actuator position, it cannot know how long the plunger rod nor where the seal will bottom-out and therefore, the algorithm must sense the end of travel of the plunger rod instead of calculating it. Likewise, when the actuator is being returned to its initial position at the far proximal end of the carriage, a spring on the inside proximal wall of the carriage located such that the actuator will compress the spring at the far end of travel could signal the MCU in similar fashion when the actuator has reached its far proximal position. When en embodiment is so equipped to detect accidental penetration of a blood vein by the needle, aspiration is required to draw fluid into the syringe cylinder for the sensor to analyze the aspirate. To aspirate the tissue, the plunger rod would need to have force applied in the reverse or rearward direction. Hence, the plunger thumb pad would need to be captured by the actuator by such suitable means such as a slot for the thumb pad to reside in. Then, the actuator motor would operate in reverse for a short distance to aspirate from the needle into the syringe cylinder. Since the software is able to track position, this function would be provided by position control instead of torque monitoring. Once the tissue has been aspirated and the aspirate analyzed, the software can decide if it is ok to proceed with dispensation of the medicament into the tissue as normal, or if the injection needs to be aborted because a vein has been breached.

The following are the approximate specs of the actuator motor:

Assuming Lead Screw pitch=L=3.18 mm/rev.
Converting: (3.18 mm/rev)/2 pi rad/rev)=0.506 mm/rev or 5.06×10^-4 M/rad
And assuming Screw Eff=0.75
And F=sticky friction of Actuator plus load=3.5 N
And $S_L$=Actuator travel velocity=10 mm/sec
$T_{travel}$=Torque of Gearmotor output at travel velocity=3.5 N*5.06×10^-4 m/rad)/Eff=0.00177/0.75=0.00236 Nm/rad=2.36 mNm/rad=0.236 Ncm/rad
$RPM_L$ of Gearmotor at travel velocity=(10 mm/sec)*(rev/3.18 mm)*(60 sec/min)=189 RPM of gearbox output shaft $T_{stall}$ (Equating the travel torque to 70% of stall torque gives) 2.36 mNm/0.7=3.37 mNm No Load Speed=630 RPM (since y=mx+b and m=−(189/(3.37−2.36))=−187 and therefore b=187 (3.37)=630 RPM Affixed to the rearward end of the housing is the carriage motor. This motor is attached to a lead screw onto which is threaded a lead nut, the lead screw pointing forward and through the proximal wall of the carriage. The nut is fixed within the proximal wall of the carriage so that rotation of the motor and lead screw causes the nut to travel forward and rearward on the screw thus bring the carriage forward and rearward with it. Since the finger flange of the syringe is captured by the elastomeric flange grip and the elastomeric flange grip resides in the carriage, the syringe is then carried forward and rearward by the carriage movement which is produced by the carriage motor. The syringe guide in the distal guide tube or the needle guide within the disposable needle shield, depending upon the embodiment, is designed to travel a set distance of approximately one and one half inches. The syringe guide or the needle shield is sized such that, the proximal end of the needle is one and one half inches from the distal outside face of the housing. The carriage in its normal travel mode is caused to travel the full amount of one and one half inches. Thus, needles up to one and one half inches can be accommodated as well as smaller needles down to a practical limit of about one half inch. In other words, the injector accommodates syringes with attached needles of between one half inch to one and one half inches since the initial position of the proximal end of the needle is one and one half inches from the distal face of the housing and the carriage always moves one and one half inches (plus a small amount extra) in its travel. Therefore, the needle, regardless of its length within the stated range, is always completely inserted into the patient's tissue. One and one half inch needles will begin to exit the housing almost immediately (the tip of the needle is recessed within the housing by a small distance), while shorter needle lengths will begin to exit the housing just a little bit later as the shorter needle takes a longer time to reach the opening in the distal face.

The carriage motion is produced by the carriage motor which is under the control of the MCU and the speed is controlled by suitable electronic Pulse Width Modulation (PWM) drivers. The MCU causes the carriage to accelerate to a fixed travel speed and then decelerate to a slower speed as the carriage nears the one and one half inches of travel. Then when a sensor detects the end-of-travel limit, the MCU causes the carriage motor to decelerate to a stop. This motion sets the needle into the patient's tissue. This motion is referred to as a velocity profile and is under control of the MCU. The same velocity procedure is followed in removing the needle from the patient's tissue, although a different speed may be employed. Typically, the speed at which the needle is inserted is changeable via the menu system. Additional details will be explained further below.

Within a bottom compartment in the proximal portion of the housing, is located the integrated circuit board. On this board is located the MCU and all the electronic integrated circuits, which shall be explained in detail further below. Of particular interest to the movement of the carriage, is the carriage travel position sensor which is located on the integrated circuit board. This is a photo diode/photo transistor combination which detects if a position fin that projects underneath the carriage and is part of the carriage is occluding light from the photo diode from reaching the photo transistor as the carriage and the protruding fin travels with it forwards and rearwards. The fin is sized such that, when the carriage is between travel limits the fin occludes or interrupts the light from reaching the photo transistor while when the carriage reaches either the forward travel limit or the rearward travel limit, often referred to as the "home position", the fin does not occlude the light from reaching the phototransistor. The fin thus indicates the ends of travel of the carriage to the MCU. The software knows which end of travel the carriage was being driven toward and thus knows which end of travel has been reached without having to include two separate photo interrupter sensors. Said another way, the fully retracted carriage position is referred to as the carriage home position, and the fully extended carriage position is referred to as the carriage travel limit position. The position fin extending down from the underneath of the carriage bottom and occluding or not occluding light from crossing from the photo diode to the photo transistor is what tells the MCU when the carriage has reached either the home or travel limit positions. This carriage travel position sensor is an optical sensor commonly referred to as a transmission type photo interrupter, and more specifically, this is the typical device used to detect position in optical encoders which usually detect rotary positional information. In analogy, the photo interrupter performs the same function for the carriage travel limits as the torque (motor current) sensor does for the syringe plunger actuator travel limits. It tells the MCU when the carriage has traveled to its limit of one and one half inches and then when it has returned the one and one half inches to its home position. When one of the two limits is detected by the position sensor, the MCU decelerates the motor to a stop. The difference is with the actuator, the travel limit is not a fixed distance, but rather, a higher torque required to further compress a spring.

The following are the approximate specs of the carriage motor:

Assuming Lead Screw pitch=L=3.18 mm/rev

Converting: (3.18 mm/rev)/2 pi rad/rev)=0.506 mm/rad or 5.06×10^-4 m/rad

And assuming Screw Eff=0.75

And F=sticky friction of Moving Carriage plus load=1.4 N

And $S_L$=Moving Carriage travel velocity=30 mm/sec $T_{travel}$=Torque of Gearmotor output at travel velocity= (1.4 N*5.06×10^-4 m/rad/Eff=0.00708/0.75=0.00095 Nm/rad=0.94 mNm/rad=0.094 Ncm/rad $RPM_L$ of Gearmotor at travel velocity=(30 mm/sec)*(rev/3.18 mm)*(60 sec/min)=566 RPM of gearbox output shaft.

$T_{stall}$ (Equating the travel torque to 50% of stall torque gives) 0.94 mNm/0.5=1.88 mNm No Load Speed=1132 RPM since y=mx+b and m=−(566/(1.88−0.94))=−602 and therefore b=602 (1.88)=1132 RPM Within a bottom compartment in the distal portion of the housing is located the battery. The battery could be a rectangular rechargeable battery or three rechargeable AAA cells, or three non-rechargeable AAA batteries. In one embodiment, the battery is a single cell lithium ion battery that is charged in situ. In the preferred embodiment, the battery consists of three AAA rechargeable cells which are charged while in the injector through the USB port power or can be removed and fast charged in a separate battery charger. This provides more flexibility to the user. In perhaps an embodiment which is intended as a lower priced unit, the preferred battery would be replaceable disposable AAA cells which get replaced when discharged. In the case of replaceable batteries, a battery door is provided to replace the batteries, as discussed above.

Also located in the bottom compartment of the distal portion of the housing is located the haptic motor. This is a vibration producing motor such as found in cell phones. The pitch or vibration frequency is under control of the MCU and the speed is controlled by suitable electronic Pulse Width Modulation (PWM) drivers. The haptic motor is necessarily firmly mounted to the housing with the rotation axis aligned with the major axis of the injector in order to cause the housing to vibrate at various pitches which the user can feel while holding the injector in their hand. The variable vibration pitch is used to provide biofeedback to the user as to the injector's position pressure on the skin and as to the injector's angle to the skin.

On the distal face of the housing are electrically conductive pads which are in electrical communication with the electronics on the integrated circuit board. These conductive pads could be deposited onto a flexible electrical circuit or they could be electrical traces on a rigid printed circuit board. These electrical conductive pads are arranged around an opening in the face of the distal end of the housing. More specifically, the conductive pads are arranged around the opening which the needle emerges as the carriage moves to its forward position. Two sets of conductive pads are arranged so that each set is diametrically across the opening. First one set and then the other set, in rapid succession form a circuit which is completed by touching the pads against the skin. Across these sets of conductive pads, a voltage is imposed such that, when the skin bridges a set of conductive pads, a constant current of one tenth of a microamp. Each contact against the skin produces a certain conductance and the skin itself represents a certain conductance. In this embodiment, the conductance is not of interest other than being able to ignore it. What is of concern is the sum of conductances of the set of conductive pads against the skin. The pressure of the conductive pads against the skin reduce the value of the conductances and therefore, the total conductance as measured across a set of conductive pads, the skin's conductance being taken as a constant. To state for clarity, a psycho-galvanometer is not being established with these circuits. The Tarchinoff response nor conductance due to increased perspiration is of interest, but rather, the increase or decrease in conductance afforded by the completeness of contact produced between the conductive pads and the skin is the measured value of interest. It has been discovered that if a set of conductive pads being held against the skin produce a total conductance that increases if the injector distal surface is angled against the skin in the direction of the plane passing through the conductive pads and the needle axis. Thus, when the injector is held at an angle, a lower conductance is produced across a set of pads which are in the plane of those conductors. The lower the conductance means the larger the voltage drop across the that set of conductors. This voltage drop across any of the two sets of conductive pads is the measured variable. A multiplexer switches between the two sets of pads in rapid succession and the voltage drop across each set is measured. A difference in voltage drop between each of the two sets means that the injector is being held at an angle; otherwise, there would be no difference between the two sets of conductances. If an audio tone or a frequency of haptic vibration or both is produced in direct proportion to the difference on total conductances as measured by the two sets of conductive pad, the user will effectively be provided with a biofeedback signal that they are holding the distal surface of the injector non-parallel to the skin's surface or in other words, the injector is not being held perpendicular to the skin. This biofeedback can assist a visually impaired operator to hold the injector so as to inject the needle perpendicularly into the tissue or to assist any user even with good vision to inject themselves in a perpendicular manner when giving themselves an injection in the gluteus muscle because anyone would have trouble judging if they were holding something behind themselves in a particular angle. This biofeedback can also be of great assistance for the dexterity challenged. Since the MCU will be recording the conductances and the difference in conductances, it can tell if the injector is being held steady or if it is being held lightly against the skin or firmly against the skin. This information is routed to an algorithm which produces variable haptic vibration frequencies and audio tonal frequencies and in this way, the user can hear and/or feel how the injector is being held against the skin.

In an optional embodiment of the invention, a TENS function can be realized by using the conductive pads with some additional electronics. Specifically, TENS is Transcutaneous Electrical Neuronal Stimulation and this technique has been shown in laboratory studies to reduce pain through nociceptive inhibition at the pre-synaptic level in the dorsal horn, thus limiting its central transmission. In simpler words, electrical stimulation of neurons can reduce the sensation of pain. Since pain can be experienced due to the needle damaging a nerve fiber as it passes into the tissue, Transcutaneous Electrical Nerve Stimulation on either side of that injury can reduce the sensation of the pain experienced by the patient. The neuronal stimulation in this embodiment would briefly precede the insertion of the needle into the tissue and possibly continue during needle insertion but at a lower intensity. Typically, one second of stimulation by 20 milliamp pulses at a frequency of 200 Hz with a pulse width of 200 microseconds would be applied across the area of skin where the needle would be inserted. Since the same two sets of electrically conductive pads as are used for the skin sensor would be used for the TENS, the effect would be applied directly across the site where pain could be produced by the needle insertion. Not every needle insertion produces pain, but some do and the TENS effect could produce a significant reduction of this pain experienced by the patient. Reduction in pain experienced by the patient translates to improved confidence in and acceptability of use of the injector, which translates into a more consistent compliance history for the patient.

Within the forward portion of the housing is a flexible electric circuit which serpentines through the folding hinge to be terminated on the integrated circuit board in the bottom compartment of the proximal portion of the housing. In the forward portion of the housing, the flexible electric circuit emerges from the bottom compartment through a slot between the lower and upper compartments so that it can reach various sensors in the upper portion of the forward portion of the housing. Specifically, the flexible electric circuit is so shaped that its traces can reach the lid closed sensor, the hinge straightened sensor, the injection initiate button, and the skin sensor conductive pads. In the syringe guide embodiment of the invention, the conductive pads that make up the skin sensor are contained on the flexible electrical circuit. The flexible electric circuit is so shaped that the traces to the conductive pads thread through a wire-way shaped trough and the flexible electric circuit folds flat onto the distal surface of the distal end of the housing. In the disposable needle shield embodiment, the flexible electric terminates in a connector on a pressure contact circuit board which makes electrical connection between the flexible electric circuit and the conductive skin sensor pads through conductor molded into the disposable needle shield. These conductors are pressed against conductive surfaces on the pressure contact circuit board when the disposable needle shield is attached to the injector housing with a twist action. In addition to the four molded-in conductors which are electrically connected to the skin sense conductive pads, there are two extra molded-in conductors which are connected together at the distal face of the disposable needle shield. These two extra conductors form a continuity path back through the flexible electric circuit so that, when the disposable needle is attached to the housing, continuity is provided in order to signal to the MCU that the disposable needle shield has been attached. Optionally, the flexible electric circuit may convey signals from a "blood in aspirate" sensor which is described further below.

Additionally, the haptic motor and the battery are attached by tiny electrical cables which either thread through the folding hinge to terminate onto the integrated circuit board or they terminate onto the flexible electric circuit, which threads through the folding hinge to conduct signals to the integrated circuit board.

An optional embodiment is to provide a "blood in aspirate" sensor. Some drugs have specific instructions for their administration, that if a vein has been pierced by accident, the needle should be withdrawn and the injection started over in another location. This occurrence is checked by aspirating. Basically, once the needle is inserted into the tissue, the plunger rod with attached seal is drawn rearward thus creating a vacuum on the other side of the seal which then causes fluid from the tissue to flow into the needle and subsequently, into the syringe cylinder. If the needle has pierced a vein, there will be blood in the fluid. This invention can check for such occurrence by observing the absorption of light as it shines through the syringe cylinder. To perform the aspiration, the actuator would be provided with a means to make the thumb pad on the end of the plunger rod captive. This could be accomplished by providing a slot on the end of the actuator spring. When the syringe is placed into position with the needle in its guide, the finger flange into the elastomeric flange grip and the thumb pad into its capture slot, when the actuator is ran in the rearward position for a short distance, fluid will be aspirated into the syringe cylinder. The presence of blood is checked in the following way. A light emitting diode (LED) would provide light that would be filtered to pass only the red frequency that is absorbed by the heme in hemoglobin. The filtered light is pointed so that it shines through the syringe cylinder onto a photo transistor that is sensitive to the wavelength of that red frequency. When blood as opposed to interstitial fluid which is primarily clear is aspirated into the syringe cylinder, the phototransistor will sense a drop in light intensity, thus signaling that blood is present and thus that a vein has been pierced. The electrical information to and from the LED and the phototransistor would be conveyed by the flexible electric circuit as described above.

In the syringe guide embodiment, the syringe guide is molded such that the distal end of the syringe fits snugly within the guide. The guide likewise, is formed in outside diameter so that it slides within the guide tube with ease. The syringe guide has a flange on its proximal end which fits into a slot at the very front of the carriage. The middle of the syringe guide is a portion of a cylinder. Specifically, it is a longitudinal slice of a cylinder of approximately 140 degrees semicircle as viewed down the axis of the needle. Projecting up from the midsection of the semicircular middle of the guide are two flared grips for inserting and retracting the guide from the interior of the housing. The syringe guide is 140 degrees of a cylinder so that the syringe can be inserted within it as its axis of symmetry is the same as the needle axis. When the syringe guide's distal end is inserted into the guide tube and the proximal flange of the syringe guide is inserted into the slot at the distal front of the carriage, a bridge is formed such that when the carriage moves forward to insert the needle, the guide slides within the guide tube guiding the needle down the tube.

In the disposable needle shield embodiment, there is no syringe guide, but rather a needle guide within the needle shield. The disposable needle shield embodiment is designed to work with Luer type removable needle/syringe combinations or other such combinations which work on a similar principle. The needle guide within the needle shield is biased toward proximal end of the needle shield by a spring so that the needle guide is at the end of the needle shield nearest to the syringe being inserted so that it is ready to accept the insertion of the forward end of the syringe. Note that even though it is referred to as a needle guide, it guides the front of the syringe itself as the needle guide moves within the needle shield. The needle guide is internally molded to accept Luer type needles. These needles have a connector at their proximal end that has four fins. As the Luer needle is inserted into the needle guide, the fins engage with depressions on the interior of the needle guide. Thus, if the needle guide were rotated axially, the Luer connector would be forced to rotate axially. The needle guide likewise, has two fins that mate with groves with the interior of the needle shield. Thus, if the needle shield were rotated axially, the needle guide would be forced to rotate axially. Thus, if the needle shield were rotated axially, the Luer needle itself would be rotated axially. Luer type needles come in two types; slip and lock. Both types are removed from a Luer syringe by rotating the needle axially. Normally, this is accomplished by rotating the needle protective cover which has groves to accept the fins of the Luer needle's connector. When Luer needle/syringes are used with the disposable needle shield embodiment, the needle protective guard is removed from the needle the needle is inserted into the needle guide with the fins of the Luer needle connector engaging with the grooves within the needle guide. Therefore, the needle shield/needle guide combination acts as the needle cover in that when you twist the disposable needle shield to remove it from the housing, it likewise removes the needle from the Luer syringe and thus, the needle can be disposed along with the needle shield. Thus, the possibility of accidental needle stick is prevented because the needle is never exposed after the injection. After an injection, the carriage is moved rearward to remove the needle from the patient's tissue. The spring which biased the needle guide to the proximal end of the needle shield likewise biases the needle guide to follow and guide the needle as the syringe is retracted. Slip type Luer needles are not locked onto the syringes as are Luer lock needles but rather, the luer slip needles are held onto the syringe with a friction slip fit. Therefore, the rearward biasing spring force onto the needle guide pushes the needle back from the tissue as the syringe is being withdrawn rearward. Thus, the risk of the slip type Luer needle from becoming disengaged from the syringe is prevented.

Luer lock needles have an ellipsoid flange at their proximal end whose widest circumference is engaged by interior threads at the front of a Luer lock syringe. Thus, when you attach or remove a Luer lock needle to or from a luer lock syringe, you do so with a twist so that the ellipsoid is engaged by the threads. A similar interior thread is provided at the forward part of the injector housing where the disposable needle shield attaches only it is larger than the Luer design. Like the Luer lock needle, the needle shield of the injector has an ellipsoid flange at its proximal end. This flanges widest circumference is engaged by the interior threads on the front of the injector housing so that a twist attaches or removes the needle shield from the housing.

Operational Functions:

Control of the injector is provided by a Micro Control Unit (MCU; also known as a microprocessor), electronics, algorithms and modes of operation. The MCU is equipped with digital I/O, flash static memory plus dynamic memory, analog-to-digital converter inputs, serial communication ports, Pulse Width Modulation (PWM) outputs, and real-time clock-calendar, and stereo audio digital-to-analog outputs, one of which will be utilized to produce monaural audio output. The processor is a digital signal processor which provides special capabilities for the play of compressed audio and in particular, of high quality spoken human language.

The programs which control the injector reside in the on-board memory of the processor and are encrypted to prevent un-authorized copying of the device functionality. Human spoken language in compressed form plus ringtones and other audio queues are stored in an external flash memory.

Many programs are executed by the MCU, and notable of them are safety interlocks, PWM algorithms for controlling motor speed and TENS pulses, motor torque sensing and positional feedback and calculation, skin sensor analysis, output of multiple forms of biofeedback, display/keyboard functionality for mode settings and display of injector state, aspirate analysis, reminder timer alarming, exception handling, online communication with personal computers and battery charging.

Safety interlocks are provided for the safe operation of the injector. The lid as detected by the lid closed sensor, must be in the closed position before the MCU will allow any motion within the device to occur. If motion is underway, it is stopped. The only action that can override this is if the MCU has extended the needle into the patient and the skin sensor detects that the injector has substantially been withdrawn from the skin. In this case, the injector will withdraw the needle even if the lid were to open. This is because needlestick is deemed more dangerous than the possibility of injury from the lid being open during motion in the injector. If the hinge straightened sensor detects that the hinge is not straightened, no motion is allowed. The needle cannot be extended if the hinge is not in the straightened positioned and the hinge cannot be folded if the needle is extended. Therefore, motion cannot be initiated if the hinge straightened sensor does not detect this position. No other configuration is possible as the carriage cannot be moved without the injector in the unfolded or straight configuration. Furthermore, movement of the actuator is not allowed if the hinge is not in the straightened position. The skin sensor must detect contact with the skin for any motion to occur except if the needle is extended and contact with the skin is detected, the needle is withdrawn, as discussed above. Also, if loss of contact with the skin is detected and an injection is in progress, the dispensation of medicament is stopped and the needle is withdrawn. Furthermore, insertion of the needle cannot be initiated unless the skin sensor detects presence of the skin, and that the injector is being held perpendicular to the skin and that the injector is being held steady. Otherwise, initiation of an injection is not permitted. Additionally, loss of perpendicularity or loss of steadiness in position will cause the needle to be withdrawn and if dispensation of medicament is underway, it is stopped where it is.

The injector conducts several self-tests. At start-up when the "on/off" switch is switched "on" the MCU conducts tests such as check of battery level, illuminating all the pixels of the display to check if any are non-functioning, and other functions of the internal systems. Additionally, while in operation, the MCU is checking all measured variables such as motor torque, to see if any of them are out of operating range. If so, an error is set, displayed, and annunciated if spoken language is enabled, and the error is passed to the exception handler to decide upon the proper sequence of actions, if any. For example, if a motor torque is detected which could indicate that the syringe needle is blocked or clogged, the event is passed to the exception handler which withdraws the needle and halts dispensation of medicament, if it has begun. Likewise, if a high carriage motor torque is detected, it could indicate that an attempt has been made to fold the device, and this would result in higher than normal friction between the carriage and the inside of the housing. In this case, the carriage motion would be stopped and the error annunciated. Many other possibilities exist, and each is mapped as to cause, effect, and most appropriate action. These are then built into the exception handler.

Pulse Width Modulation (PWM) is a very efficient method of driving many loads such as motor loads. In this embodiment, the MCU provides four PWM outputs. Two of these are used together in conjunction with an H-bridge (two sets of four MOSFETS) to drive either the carriage motor or the actuator motor forwards and backwards plus braking and coasting. Two PWM lines are used for either motor because two lines enable the MCU to drive the motor forwards or backwards by holding one low and pulsing the other high causes the H-bridge to turn on the correct power MOSFETS to drive the motor in one direction or the other. Reversing the roles drives the motor in the other direction. Holding both lines high causes the motor to coast by putting all the MOSFETS into high impedance, and holding both lines low causes the motor to break by turning on the two bottom MOSFETS to cause the motor current due to the generator effect to circulate through the armature. The MCU has a special PWM sub-system to accomplish the timing required with these waveforms. A third PWM output is used to drive the haptic motor by driving a single power MOSFET on and off. The fourth PWM output is used to generate pulses for the TENS unit. The principal behind PWM output is that the full supply rail is either turned on or turned off. This reduces losses that result from other drive methods where the supply voltage is reduced. Essentially, a square wave is generated with a definite period. The square wave is on for part of that time and this on time divided by the period time time is called the duty cycle. Varying the duty cycle varies the energy delivered to the load effectively driving the load at a variable rate. For example, a 50% duty cycle would run a motor at half the speed as it would if it were connected directly to a rail voltage reduced by half. In this way, motor speed is varied by varying the duty cycle. For the haptic motor, the varying speed results in a varying vibration pitch since this motor has an offset shaftless cam for its driven load. Also, in this way, the energy supplied to the tissue by the TENS function is varied. The PWM signal reaching the carriage and actuator motors comes from the H-bridge which is essentially power transistors arranged to provide forwards, rearwards motion, coasting, and breaking. This H-bridge is controlled by PWM square waves generated by the MCU. The haptic motor only runs in one direction, so instead of an H-bridge configuration, only one power transistor is required. A similar situation exists for the TENS function. See the PWM circuits further below.

Motion Control System: Two brush type permanent magnet DC motors supply the impetus for motion of the "carriage" and the "actuator" respectfully. The linear motion of the carriage and actuator is translated from the rotary motion of the motors by two lead screws.

In typical motion/position control algorithms, there are several feedback loops which are typically nested within one another. That is, if position is the prime goal, the position loop is the outer or ruling feedback loop with a velocity loop nested within it to get from one "position" to another. Nested within the velocity loop is a current/torque loop generating an output to produce the torque required to get to the different velocities required by the velocity loop.

With the carriage and actuators, the motor speeds are operated in closed velocity loop fashion but the position loop is only partial. Since the current of the actuator motor is already being monitored to discover its travel limits, this circuitry can be used for both motors to provide closed loop velocity control throughout their motion profile. Because only one motor is in operation at any one time, the same current measuring circuit can be used for each motor. This current can be used to calculate the actual speed of the motor if the motor's supply voltage is known (which it is because it comes from a constant 3.0 volt regulator). Note; motor speed is proportional to voltage, all other variables remaining constant. However, with PWM speed control, the voltage is not varied but rather, the "on" duty cycle is varied. This is more efficient than varying the voltage to control speed because reducing voltage is and energy lossy proposition. Normally, a constant voltage (even if chopped into square waves) supplied to a DC motor results in a constant speed. However, when the load changes, the speed will change unless the voltage (PWM duty cycle) is re-adjusted to compensate for the load change. If you measure the actual speed and, finding it is not the desired speed (not at "Setpoint"), you can make a voltage (PWM duty cycle) correction to adjust the actual speed back to the desired setpoint speed, and you are "closing the loop" and this is known as closed loop velocity control. To calculate or measure the actual velocity of the motor, several methods are commonly employed such as incremental encoders and tachometers. In the preferred embodiment of this invention, to save the cost of these devices, the speed will be calculated based upon some variables, and some constants; namely, the current I going through the motor (which is constantly being measured), the supply voltage Vsup (a constant because it is supplied by a regulator) which is the voltage the PWM chops into square waves, plus a couple of constants particular to the actual motor; $k_e$ the relationship expressing the speed per millivols of back emf voltage, where $V_{emf}=S(t)_A*k_e$. $V_{emf}$ being backward voltage produced by the generator effect as the motor spins, and R the resistance across the windings and brushes which is a semi-constant. According to Kirchoff's voltage law, the voltage drops around a circuit loop driving the motor must equal zero. Therefore:

$$V_{sup}=(I*R)+V_{emf}=(I*R)+(S(t)_A*k_e) \quad \text{or} \quad S(t)_A=(V_{sup}-(I*R))/k_e$$

where:
$V_{sup}$=the supply voltage from DC regulator connected to an H-Bridge Driver
I=Current going through the motor armature
R=Resistance across the motor armature plus brush resistance
$V_{emf}$=Back EMF across the motor
$S(t)_A$=Actual rotational Speed of the motor
$k_e$=Voltage Constant of the motor (mV/RPM)
$D_\%$=Duty Cycle–On time/Period Time
$V_{ref}$=Voltage equivalent of Duty Cycle times the Supply Voltage ($D_\%*V_{sup}$)
$V_{PWM}$=Pulse Width Modulated voltage, the time average of which, is numerically equivalent to VRef In this case, current I is being measured to calculate the actual speed $S(t)_A$, however, $V_{sup}$ is not supplied directly to the motor. Rather, $V_{sup}$ is chopped into a 25 khz (or thereabouts) PWM (Pulse Width Modulated) square wave voltage "$V_{PWM}$" whose duty cycle (on time/period) is scaled between 0% and 100% which effectively acts as if $V_{sup}$ were being varied between 0% and 100%.

Therefore, the calculated speed equation becomes: $S(t)_A=(V_{Ref}-(I*R))/k_e$

Where $V_{Ref}=D_\%*Vsup$, and $D_\%$ is known because it is being calculated (see below).

To effect feedback control, $S(t)_A$, the actual rotational speed is calculated from the above equation and compared to the desired speed (Setpoint) from the target trapezoidal speed profile and the difference is calculated. The trapezoid refers to the shape of a graph, with speed on the vertical axis and time (in this case) on the horizontal axis. Then, as the speed is accelerated, an upward sloping graph pursues till acceleration stops and the graph becomes horizontal. Then, as the speed is decelerated, a downward sloping graph ensues. Thus, a trapezoidal graphical shape of the speed command vs time function.

This difference or "error" in measured and trapezoidal speed command or "setpoint" is used as an error signal to correct the measured speed to match the desired trapezoidal speed curve. The Duty Cycle $D_\%$ is adjusted so that the desired speed is obtained regardless of load. This adjustment calculation is made to Duty Cycle $D_\%$ by applying a PID algorithm to the error signal, which will be elaborated below.

The motor speed (velocity) for the carriage and actuator is operated in what is known as a trapezoidal velocity profile. More specifically, they are operated with a modified or two-step trapezoidal velocity profile. That is, rotation is started from zero and the speed is increased at a linear rate (constant acceleration) to a travel velocity for a length of time or distance, then speed is decreased at a linear rate (constant deceleration) to a small (approach) speed until an end-of-travel indication is received. When the signal is received, the motor is further decelerated to a stop. For the carriage, this end-of-travel is a signal from the photo interrupter, and for the actuator, it is due to detection of increasing torque from additional compression of the Actuator Spring. The speed desired at each moment in time and described by a speed profile is referred to hereinafter as the speed "Setpoint" which can be changing or constant depending on the point in time on the trapezoidal graph.

DC motor brushes produce a non-linear voltage drop at the commutator somewhat similar to the forward voltage drop of a silicone diode. This means that the "R" in $S(t)_A=(V_{PWM}-(I*R))/k_e$ isn't quite a constant. However, since this R is speed dependant, its value can be estimated based upon where the motor is on the trapezoidal velocity profile. These values can be stored into a lookup table vs. time into a perfectly executed trapezoid, or, an average value could be used instead of a look-up table, but the result is less accurate than actually measuring motor speed by a mechanical device such as an incremental encoder or tachometer. Therefore, the two-step trapezoidal profile in combination with the end-of-travel sensor or detection of end of travel compensates for the inaccuracy and is used for the embodiments illustrated for the invention. To be clear, if the velocity were known exactly, a perfect execution of a regular (non-two-step) velocity profile would land the carriage at the correct location without a separate end-of-travel detection. Exact speed and position feedback are normally employed in robotics. The two-step approach is quite adequate for the injector and is certainly unique to injectors and saves the costs of detecting speed and position by mechanical devices.

As mentioned above, the velocity loop usually is nested with a position loop. That is, certain velocities are constantly adjusted so that each successive position point is reached in the required amount of time. These points form a position profile much the same as the velocity profile is made up of velocity setpoints. During the execution of a position profile, the motor is speed is controlled to be "on position" in time, and as the distance between the current position and the final stop position approaches zero, the speed command approaches zero so that the motion lands exactly in the position desired. This mode of closed loop control is usually accomplished with a parabolic shaped velocity profile. For this embodiment, the modified two-step approach can be employed where the first trapezoid of velocity commands are ran in open position loop until the second step (an adjoining smaller trapezoid) where the approach speed is commanded with position closed-loop feedback control. At that transition point between first and second trapezoids, an on/off feedback position loop begins for the final approach velocity till the end-of-travel limit is detected and then the motor speed is further decelerated to zero either linearly or by the application of brake mode by the H-bridge driver. Specifically, a trapezoidal velocity profile is calculated such that, if executed precisely, the position of the carriage or actuator will end up at the specific position where it should begin the approach speed to the final position. The small approach speed distance provides tolerance for the lack of precision due to the lack of exact velocity or positional feedback. The actual speed throughout the movement is calculated from the $S(t)_A$ equation above and compared with the two step trapezoidal profile setpoint $S(t)_C$ (Command Speed) that is calculated prior to movement, and the resulting error $e_{(t)}$ is used to provide a continuous correction in velocity. This error is feed to the PWM algorithm which turns the error into a Duty Cycle $D_{\%}$ which is sent to the H-Bridge driving the motor. If, at any time during the movement, the error between the actual velocity and the command velocity becomes larger than a certain limit, the exception handler is notified and appropriate action is taken.

As stated above, a speed $S(t)_C$ is commanded according to a trapezoidal velocity profile that has been calculated to provide the proper movement to a position. The actual speed is supposed to match the profile, but in reality, since the load isn't known or even constant, only a close approximation of the profile can be achieved. According to a trapezoidal speed profile for this embodiment, the motor rotational speed is increased, maintained, reduced and then stopped at the end-of-travel. When the actual speed is calculated from the $S(t)_A$ equation and controlled to closely to match the calculated setpoint $S(t)_C$ command from the trapezoidal profile regardless of the syringe/drug/needle load, it is called closed loop velocity control. This is accomplished by calculating any difference in actual speed and the command speed (the profile), moment by moment, and the corresponding error $e_{(t)}$ is used to adjust the Duty Cycle $D_{\%}$ output. To make this moment-by-moment adjustment in the speed command, a technique known as PID (Proportional Integral Derivative) control with feed-forward will be employed.

In the PID feedback control technique, the output from the PID algorithm $S_{(t)}$, is derived by summing three terms; a Proportional term, an Integral term and a Derivative term which are derived by multiplying a "Gain" factor by a corresponding speed error $e_{(t)}$. The gains are as follows:

Integral Gain: ensures that under steady state conditions (such as at the travel speed under constant load) that the motor speed (almost) exactly matches the setpoint speed. When set correctly, this gain will make the controller push the speed to the setpoint speed. However, sufficient integral gain to quickly achieve the setpoint speed can cause overshoot if it weren't for the other gain terms, which dampen this out.

Proportional Gain: gives fast response to sudden load changes (such as when the "Actuator" first encounters the "Plunger Thumb Pad") or changes in the speed command, or "setpoint" (such as during the acceleration and deceleration sections of the trapezoid where the velocity command is constantly being changed). This gain is typically many times higher than the integral gain so that relatively small deviations in speed are corrected while the integral gain slowly moves the speed to the setpoint. Like integral gain, when set too high, proportional gain can cause a "hard" oscillation of a few Hertz in motor speed.

Derivative Gain: is used to give a very fast response to sudden changes in motor speed. It can be deployed to reduce the rapid speed oscillation caused by high proportional gain. These two gains are used in conjunction, and generally, all three gains when used in unison, produce the best response.

The PID control analog equations have to be converted from a theoretical continuous process into a real-time "discrete" system so that it can be implemented in the MCU. What this means in practice is that the measurement of the motor speed and the calculation of the output is only performed a regular intervals that can be implemented from a timer interrupt. Thus, the actual speed is measured and is compared to the setpoint speed command and the difference is taken and is used to calculate a new speed command by using the PID function at regular intervals, perhaps every 10 milliseconds. Specifically, once the actual speed is calculated (using the above equation), it is stored in a variable "actual speed" and compared with the command speed (Setpoint) as specified by the current point on the trapezoidal profile, and this difference or "error" in speed is stored in a variable called "Current Speed Error" or $e_{(t)}$. This error value is also stored into a couple more places. The second place is a sliding window or FIFO so that the last five to ten to twenty speed errors can be summed (the number is adjustable). This sum is called "Speed Error Sum". The third place to store the "Current Speed Error" is a two position FIFO used to calculate the difference in the last two speed errors. This difference is called the "Speed Error Delta". Then the output of the PID function is the sum of these error factors each multiplied by the gains as described above. Thus:

PID Output=(Proportional Gain*Current Speed Error)+ (Integral Gain*Speed Error Sum)+(Derivative Gain*Speed Error Delta). These PID Gain values are determined by experimentation and the process of finding optimal values for them is known as "tuning the loop". Once the values are determined, they will be constants programmed into the injector's program memory and used by the velocity loop control function portion of the algorithm for every device.

Since the PID algorithm operates on an error signal, in practical velocity control where loads or setpoints are changing, the output is always behind in following the trapezoid velocity profile, especially when the profile accelerates or decelerates or encounters a load variation. Therefore, in the preferred embodiment of this invention, an advanced technique known as "feed forward" will be employed to help the output match the desired profile. With feed forward control, an "Empirical Duty Cycle" $ED_{\%}$ profile is developed for an "average" syringe/drug/needle load or even for specific drug/needle gauge combinations which if executed for that average or specific load, would produce the desired trapezoidal velocity profile without PID operation on an error signal. The real world tends not to match an average or even one load to the next same device. Therefore, the error based velocity command S(i) (which is the PID sum) is summed with the feed forward empirical duty cycle command $ED_{\%}$ to create the output duty cycle command $D_{\%}$, to the PWM algorithm, which turns the duty cycle into a pulse train to send to the H-bridge motor driver. The deviation from setpoint then, will be reduced in size since part of the duty cycle command ($ED_{(i)}$) being sent to the motor is already sufficient to produce the desired trapezoidal velocity profile for an average ore even specific load at least very closely. The main advent of feed forward is it keeps the actual from lagging behind the setpoint profile. Note, an expected torque (current) value curve is stored with the feed forward velocity profile. Its use is described further below.

The velocity error $e_{(t)}$ which is a deviation of actual speed from setpoint, is compared to a tolerance value. This tolerance will be determined empirically by testing a range of syringe/drug/needle loads. When an out-of-tolerance condition occurs (the error is larger than the tolerance), a fault is triggered and the exception handling algorithm will announce in a manner set within the menu system, such as audio sounds and a displayed message and/or human voice, that a fault with the movement of the internals has occurred and provide instructions on what to do.

The above described two-step velocity profile and end-point positional feedback method is a hybrid algorithm which reduces costs. In this embodiment, the hybrid control strategy is illustrated for both the "Actuator" and the "Moving Carriage". The haptic motor has no position to reach, and for it, only closed loop velocity control is required. Likewise, for the TENS function; only PWM control is required.

In the case of the "Moving Carriage", the length of travel is always the same (unless aspiration is taking place) so approximately 1½ inches plus 3/16th inch (1 11/16 inch total) of travel will be required in order to accommodate the maximum 1½ inch needle plus the recess distance from the tip of the needle to the outside distal surface of the housing. Therefore, travel length is fixed between two limits of absolute position 1 11/16 inches apart at full stroke.

In the case of the actuator, again the positions of concern are at the ends of travel. This time, they are at a length of travel sufficient to press the syringe plunger all the way into the syringe cylinder and then retract the "Actuator" back to its starting (or "home") position. The "home" position is a fixed location; however, since the actuator needs to accommodate a range of syringes of various plunger lengths, the stroke length for the "Actuator" will vary and will have to be sensed as the actuator advances. To find this limiting position, the following method is employed. An "Actuator Spring" is attached to the "Actuator". This spring could be a coiled spring or flat spring steel shaped as a U or an S or any other suitable arrangement to supply spring compression between the plunger thumb pad and the actuator. As the "Actuator" is pressing the plunger into the syringe and the drug is being dispensed, the "Actuator Spring" is in between the actuator and the plunger thumb pad and will only be partially compressed (the spring is sized for approximately 50% compression for the highest force load of syringe/needle/drug combination). When the Syringe Plunger Seal reaches the bottom of the cylinder bore, all of the drug will have been dispensed and the plunger cannot travel any further, the motor is still rotating because the stroke length varies per syringe and the algorithm doesn't know what that stroke length is. As the motor continues rotating, the "Actuator Spring" becomes further compressed, forcing a greater torque load on the motor. The motor control algorithm is monitoring the motor current already in order to calculate the motor speed. Therefore, the algorithm also utilizes this current, which is directly proportional to torque, to sense this increase in load as an indication that the seal has reached the bottom of the cylinder bore. Said another way, this greater load at the end of travel is sensed as an increased current through the motor because motor torque is proportional to current and this increase is used as a signal that the end of travel has been reached and the motor should be stopped. In that the medicament has now been dispensed, the needle will be withdrawn from the patient and back into the housing, and then, the actuator is returned back to the beginning "home" position with the same torque sensing algorithm. That is, a separate actuator return spring supplies the greater load on the motor when the actuator compresses it at the far proximal home position, signaling that the end of return travel has been reached.

The position of both the carriage and the actuator will be calculated at all times by taking the integral of its velocity over time. This isn't needed for their control of movement since the hybrid positional and velocity algorithm as described above is employed for this purpose. However, positional information can be useful for error control. For instance, in the event that the photo interrupter fails the MCU would be tracking position and will thus know if the carriage has overshot the travel limit. Positional tracking is also used in calculating a new two-step trapezoidal profile in the event that the carriage has to be moved an amount other than the full one and one half inches that it normally traverses, as explained below. In the event that the carriage position suddenly stops advancing or advances slower than it should before the photo interrupter transistor is signaled, the velocity error being out of tolerance would also signal a fault and pass it to the exception handler. An example of the latter would be if the user had placed the skin sensor against a metal conductive surface and pressed the injection initiate button. The restriction of the non-puncturable surface would cause the velocity error to exceed the tolerance and this would alert the exception handler which would stop the carriage from moving forward and return it to its proximal home position, perhaps dragging a bent needle behind it. Since both velocity error and positional error handling will be employed, double redundancy is provided to catch misuse or failure conditions.

Considering movement for the carriage, the sequence of steps are as follows: 1$^{st}$ The speed is increased from zero to 30 mm/sec (adjustable) in a linear fashion and once this speed is obtained (in approximately 3/16th inch) the speed is maintained at that rate to a point just before experimentation has shown that the carriage after deceleration to an approach speed, will have traveled no more than 1½ inches with any load the injector is designed to accommodate. At that point, the speed is decreased linearly to the approach speed which is perhaps 10% of the travel speed (or 3 mm/sec.) This speed is maintained until the photo interrupter signals that the carriage has reached the end of its travel (the needle is all the way into the patient), and the motor is then decelerated to a stop or a brake condition is initiated by the H-Bridge, or both. Then the Actuator is advanced to dispense the drug. Provided the actuator successfully completes dispensing of the drug, the carriage is then returned to its home position in similar manner to that from which it was advanced. That is, a reverse speed is increased in linear fashion to a return travel speed and maintained at that speed for an amount of time just sufficient such that, after deceleration to an approach speed, the carriage will be no closer than 3/16 inch from the home position. At that point, the speed is reduced linearly to the approach speed that is perhaps 10% of the return travel speed and maintained at that speed until the carriage photo interrupter signals that the carriage has reached its home position and the motor is then stopped.

In the event that the carriage motion has to be arrested, such as loss of proper skin contact or angle of the injector to the skin, and the carriage retracted before the full stroke of inserting the needle is reached, a new modified trapezoidal velocity profile is calculated based on the current position of the carriage and the distance back to the home position. Then that profile is executed to retract the needle back into the injector to avoid the possibility of accidental needle-stick.

For the actuator, the velocities commanded and the sequence of steps are as follows: $1^{st}$ The speed is increased from zero to 10 mm/sec (adjustable) in a linear fashion and once obtained (in approximately $3/16^{th}$ inch) the speed is maintained at 10 mm/sec to a point just before experimentation has shown that the actuator will have traveled no further than the location that is just short of the shortest travel distance for all the standard and non-standard syringes that the injector is compatible with. At that point, the speed is decreased linearly to an approach speed of approximately 3 mm/sec. This speed is maintained until the algorithm detects that the Actuator Spring is being further compressed thus increasing the current through the actuator motor. The increased current indicating that the actuator needs to be decelerated to a stop.

Within the sequence just stated, there is fine structure consisting of multiple torque loads and the ability to distinguish one force from another. This fine structure will be further expounded below in the section called the "Actuator Torque Sensing Algorithm".

Immediately below, is a flow chart of the speed summing, PID processing and feed forward summing to result in an input to the PWM algorithm that is implemented in the MCU.

Actuator Torque Sensing: The actuator motor drives the actuator riding on the lead screw which pushes against the plunger thumb pad which causes the syringe plunger seal to force the liquid out of the syringe through the needle.

A primary purpose of actuator torque sensing algorithm, which is implemented by software and current sensing electronics, is to execute a velocity profile causing movement. During movement, it is necessary to detect when the liquid is being dispensed. Then, when the medicament has been dispensed, it is necessary to stop forward movement by sensing the increase in motor torque as the plunger reaches its end-of-travel. Specifically, it is necessary to stop the motor before it reaches the point of stalling. This is accomplished by the actuator spring which is partly compressed while the liquid is being dispensed. When the syringe plunger seal reaches the bottom of the syringe cylinder bore, all of the liquid has been dispensed and the plunger rod stops traveling, but the software doesn't know the plunger has stopped. As the motor continues to rotate, the actuator continues forward and the actuator spring becomes further compressed resulting in higher torque on the motor. The increased torque is sensed as increased motor current and used to signal the algorithm to stop the motor. A similar scenario is used to return the actuator to the proximal "home" position.

Given: Force on the actuator requires torque from the motor, which in turn, requires current. Therefore, current is proportional to force. Force, torque, and current are used interchangeably here below.

Given: Actuator no-load (not pushing against the plunger) forward and reverse currents (torques) are constant values at constant speeds. There are multiple forward speeds which can be selected from the menu system; "general", "fast", and "slow dose", and two modified torque modes; "High Viscosity", and "Shear Sensitive", plus one return (reverse) speed, which results in multiple currents under dispensing load, one higher current at the end of travel, and one standard return no-load current, and optionally, an aspiration load as a vacuum is drawn within the syringe. Additionally, there is a no-load current in the forward direction during the time before the actuator encounters the plunger, and also a very light load during practice modes where a syringe is present (without needle) but no medicament is loaded into the syringe. The term no-load does not here imply that there is zero load, but rather no load larger that that of traveling without pushing anything.

Given: Momentary sticky friction torques can happen at the beginning of actuator travel under no-load and at the beginning of actuator contact with the plunger, and at the beginning of aspiration if that operation is so included.

Given: The load (torque) reflected back to the motor due to the actuator pushing the seal in the cylinder barrel, will depend upon the brand of syringe, its size, the viscosity of the liquid in the syringe, and the length and gauge of the needle the liquid is being forced through. However, this load will be constant during any constant speed of the actuator once the medicament begins to exit the needle into the patient.

Given: The instantaneous current value of the motor is measured with an ADC (Analog to Digital Converter) and input into a sliding window register (a FIFO) whose value can be an average of measurements. This averaging can be used to dampen various sources of noise from among the measurement. Typically, the FIFO would have enough values (typically three measurements averaged or five measurements with the high and low discarded and the remaining three averaged) just sufficient to ensure elimination of the noise. These measurements happen in rapid succession at the beginning of calculations. This averaged value becomes the "current value" which is used as a torque value and also used to calculate rotational speed of the motor. Note: the "current value" is the value used to calculate the actual speed in the $S(t)_A$ equation.

Given: The current value is input into a second FIFO which is just sufficiently large to calculate the first derivative (typically two current value measurements), and the derivative "dI/dt" (change in current "I" per small delta "t") is merely computed as the difference between the current value and the last current value and the time factor isn't computed since a timer driven interrupt sequences all the calculations on a constant timer driven interrupt interval. This dI/dt value is called hereinafter, the "torque delta" or the "derivative".

The sequence of the actuator algorithm is as follows for the non-aspirating embodiment (the aspirate analysis sequence will be described further below):

A) The motion procedure begins as follows. A trapezoidal profile is fetched from memory based upon the speed modes mentioned above. The speed mode may be general, fast, slow dose, high viscosity, and shear sensitive. The first three are trapezoids of three different heights. The acceleration and deceleration sides of the trapezoid are of such angle to get to speed quickly without causing vibration or the feeling of the device lurching. The last two speed modes have the capability to modify the trapezoidal speed profile by changing the height of the trapezoid. The high viscosity, mode limits speed if the torque becomes too great and the shear sensitive mode limits speed to maintain a lower than normal torque. This is done by clipping the travel speed to a lower value. Specifically, if the torque in the high viscosity mode begins to approach the torque as would be experienced at the end-of-travel, the acceleration will be halted and a new lower travel speed will be used. For the shear sensitive mode, the acceleration will be stopped when the torque reaches perhaps 50% of the average load or of a specific load if it is known.

B) A feed forward duty cycle profile is based upon a general "average" syringe feed forward profile as determined during development and testing of the device.

C) The velocity profile execution is begun and the actuator motor begins rotating, moving the actuator towards the syringe thumb pad, and until it is encountered, the motor will be operating under a forward no-load condition. The closed loop velocity algorithm causes the motor to accurately follow the velocity profile and it reaches the travel speed before the actuator encounters the syringe thumb pad. The current velocity error is checked against the tolerance value during all motion. The actuator begins moving at constant travel speed. The algorithm begins checking torque for an increase due to encounter of the syringe's plunger. It does this by monitoring the derivative of the current value and the torque value.

D) As the "Actuator" encounters the plunger, the torque (current) will increase to a value required to overcome any sticky friction of the syringe seal and then the force necessary to dispense the liquid from the syringe. This means that as the actuator encounters the plunger, force and derivative will increase followed by a decrease in derivative as the medicament begins flowing at a constant speed. The torque may initially overshoot the required dispensing torque due to initial sticky friction of getting the syringe plunger seal to move, resulting in at first, a large positive derivative followed by a decrease in derivative due to overshoot as the torque decreases below the sticky friction torque. The software will be looking for an increase in derivative as the medicament starts expelling, and as constant speed is employed for dispensing (the flat part of the trapezoidal profile) the derivative should drop back to around zero while the torque itself remains higher than the no-load torque. During the dispensing phase, the measured torque (current value) should be at least 120% of no-load torque or a value which would indicate at minimum, that an empty syringe's plunger is being actuated. When detected, a "plunger encountered" flag is set and the trapezoidal profile proceeds. If this flag isn't set within a maximum distance (established by the longest distance to the thumb pad for the selection of standard and non-standard syringes the device is designed for), another flag "no syringe present" is set and the exception handler is informed.

E) If high viscosity has been selected from the menu system, the algorithm checks the monitored torque against a maximum value and if that value is being approached, the speed profile is limited to a speed where the torque is a small amount below the maximum torque. If shear sensitive has been selected from the menu system, the algorithm checks the monitored torque against the feed forward amount expected, and the acceleration is limited at a torque which is perhaps 50% of the feed forward torque expected.

F) Between the beginning of the medicament being dispensed and the end of travel for the actuator, the deceleration to approach speed will occur. When so encountered, the actuator motor is decelerated to the approach speed and the second trapezoid profile is begun and on-off position loop control is begun. During the deceleration, the derivative will become negative and then return to zero as the deceleration stops at the approach speed, however, the negative derivative is not significant to the algorithm during this phase. The end-of-travel will produce a large negative derivative and accompanying increasing torque, and this is significant to the next step in the algorithm.

G) "Check for end-of-travel". In this step, the software looks for a second increase in torque at the end of travel. Specifically, the negative derivative accompanied by an increasing torque value signifies further compression of the actuator spring and a torque value from compression of the return spring which signifies that the plunger has stopped moving and it is time to stop the motor. When encountered, the motor is decelerated to zero speed and a break command is sent to the H-bridge by the PWM algorithm which causes the motor to be stopped.

H) The actuator torque algorithm is temporally suspended while the carriage motor is reversed to withdraw the needle.

I) After the needle has been retracted into the injector, the actuator motor is reversed and operated at the no-load return speed back to the proximal "home" position. It is under no-load because it is not pulling the plunger back out of the syringe (it only can push the plunger). As the motor rotates in reverse to return the actuator to its initial home position, the software is looking for a rise in torque and more specifically, the negative derivative accompanied by continually increasing torque which signifies that the actuator is compressing the actuator return spring and it is time to shut off the motor. When detected, the motor speed command is decelerated and the H-Bridge drive is either set to brake or coast by the PWM algorithm. END.

The sequence of the actuator algorithm for the aspirate analysis model is as follows:

A) A trapezoidal profile is selected from memory based upon moving the actuator forward to a position wherein the syringe thumb pad will engage into the captive mechanism of the actuator when a specific syringe is inserted into the housing. Which profile is selected will be determined by the earlier selection of the syringe/needle/drug combination from the menu system. If the wrong syringe is selected from the menu system, then when attempt is made to insert the syringe, the actuator will be at the wrong position to accept the thumb pad. This is because the motion control system will have to move the actuator to the exact position where the thumb pad will be located when the syringe is inserted into the device. This is because the thumb pad will be captive by the actuator (not just pushed upon) in order to aspirate (pull back on the thumb pad) and to do that, the thumb pad will have to be inserted into a U or other shape when the syringe is inserted and therefore, the actuator will have to know which syringe will be loaded in order to move the actuator into the correct position so that the thumb pad will slip into the captive mechanism when the syringe is placed into the housing. The drug will also be selected in the menu as well since this information, in combination with the syringe and needle information, will provide an exact feed forward information for each movement and therefore, very precise positioning due to very little velocity error.

B) The velocity profile execution is begun and the actuator is moved into position to accept the syringe thumb pad and the operator will be instructed to insert the syringe. After which, the user closes the lid and begins the injection procedure.

C) The actuator algorithm is temporarily suspended while the needle is being inserted into the patient.

D) In preparation for aspiration, the trapezoidal profile is loaded such that the movement it produces will pull the plunger thumb pad backward by approximately one-half to one centimeter. The trapezoidal profile is suitable for aspiration and is similar to a forward profile except it is not a two-step profile and has no position feedback. It will simply accelerate in reverse to a fixed speed, move an amount, and then decelerates to a stop. A feed forward duty cycle profile is selected from one specified for the syringe under an aspiration (vacuum producing) load.

E) The motion backward is began and the reversed seal movement within the barrel of the syringe cylinder produces a vacuum. After the movement is complete, the motion will remain paused for a moment while fluid flows through the needle into the syringe cylinder.

F) Analysis is conducted on the aspirate to check for the presence of blood. If so detected, the injection of the medicament is aborted and the needle is withdrawn out of the patient and back into the housing. The actuator is left where it is and the patient is informed to remove the syringe and replace the needle. Then the patient initiates a new aspirated injection which causes the actuator to be returned to the home position before being moved into the correct position to capture the thumb pad, as before. During the movement, the torque is checked to insure that the syringe has been removed. If higher than no-load torque is detected, the motor is stopped and the user is informed that the syringe needs to be removed.

G) If no blood is detected in the aspirate, then the dispensation of the medicament proceeds, however, the trapezoidal profile begins from the actuator position where the aspiration procedure left off. As in step 1 above, a specific profile is selected determined by the earlier selection of the syringe/needle/drug combination from the menu system. Likewise, a specific feed forward profile is also selected to match. Otherwise, the injection proceeds in the same manner as in the non-aspirate description above.

H) Once the medicament has been delivered, the actuator algorithm pauses while the needle is withdrawn from the patient and back into the housing.

I) The actuator is left where it is and the patient is informed to remove the syringe. Then the patient confirms that the syringe has been removed which causes the actuator to be returned to the home position as described above. During the movement, the torque is checked to insure that the syringe has been removed. If higher than no-load torque is detected, the motor is stopped and the user is informed that the syringe needs to be removed. END.

The Skin Sensing Algorithm utilizes measurements of conductivity between conductive pads and the skin. When the conductive pads are touching the skin, a 0.1 microamp current is passed from one electrode, through the skin and to an opposite electrode on the other side of the opening in which the needle emerges. The current is produced by a constant current source on the integrated circuit board and the voltage drop from across the electrodes is measured by a digital-to-analog converter channel in the MCU. There are two sets of conductive pads arranged in an x-y pattern that are pressed against the skin. Each set constitutes a separate electrical circuit. Skin has a definite conductance although it is relatively small (measured in µSiemens). The skin completes the circuits, one circuit in the x-dimension, and the other circuit in the y-dimension. A multiplexer switches between the two circuits in rapid succession. This arrangement provides for determination of orientation of the device in both directions in that the conductance in each circuit (dimension) is proportional to how nearly perpendicular the long axis of the injector housing (or how planar the conductive skin sensor pads) are to the surface of the skin. This is because it is in the perpendicular orientation that results in both conductive pads of any one circuit in making a low resistive circuit through the skin. In other words, if the device were not held perpendicular to the skin in the x or y dimensions, one of the conductive pads in that dimension will be pressing against the skin more and one pad will be pressing less. The net result is that the overall conductance between the two pads will be reduced. Conversely, when held perpendicular, both pads will be making good contact with the skin, and the measured conductance will be greater (the resistance of the circuit will be less). The higher the conductance the smaller the voltage drop and it is this voltage across the pads that is being measured. Also, as the device is held more firmly against the skin, the better will be the conductance between pads and skin. Therefore, each circuit measures conductance resulting from two factors, namely; the underlying conductivity of the skin per millimeter, and the conductance between pads and skin, which is increased by increasing pressure against the skin and decreased by tilt of the circuit against the skin. The conductance of the skin is considered a constant as it has a relatively small effect compared to the variance in conductance due to tilting the injector or pressing lightly or firmly against the skin. It is to be understood that, the object is to hold the distal surface of the injector housing as flat as possible against the skin. This is accomplished by holding the long axis of the injector perpendicular to the skin. When this is so done, a higher conductance will be measured across a set of conductive pads than if the injector were tilted from perpendicular in the plane established by the set of conductive pads and the axis of the injector. To this inventor's knowledge, this phenomena has never been utilized in any invention.

On skin covering the quadriceps muscle which was freshly cleaned with an alcohol pad and allowed to evaporate until almost completely dry, and using electrically conductive pads of approximately 9 square mm each, and having a 7 mm gap between them, the following averaged conductances were obtained with an hp 34702A multimeter. When the "Printed Skin Sensor Circuit" was held flat against the skin (long axis of the injector held perpendicular to the skin), 0.14 µSiemens of conductance (7 Mega ohms) was obtained, and at an extreme angle (just before loss of conductance) 0.05 µSiemens of conductance (19 Mega ohms) was obtained (64% less conductance). Therefore, there is good resolution to be able to differentiate between pressing the device at an angle and pressing it perpendicular. Additionally, when the device is held past the extreme position (which was approximately a 45 degree angle), conductance abruptly drops to zero due to one conductive pad having lost contact with the skin. Therefore, the algorithm has the opportunity to limit operation to acceptable conductances established when the device is perpendicular to a surface and furthermore, to such conductances as would be encountered by use on human skin.

Biofeedback is provided to the user based upon the measured conductance of the pads. Specifically, a variable tone can be provided by the audio speaker and/or a variable frequency vibration can be provided by the haptic motor. Here below, we shall sometimes use the terms pitch or tone in reference to the biofeedback, but it is to be understood that it could be by earthier means, audio speaker or haptic vibration or both. Two separate pitches could be used, one to represent each of the conductances in the x and y dimensions however, since the two electrical circuits are measuring across the same patch of skin, a difference in conductivity between the two circuits will indicate that the injector is being tilted and the lack of a difference in conductivity will indicate that it is being held perpendicular. If the tone is based upon this difference between the two circuits and it is reduced in pitch as the difference in conductivity is reduced, then the user will know either through their audio sense or the touch sense that the injector is being held more perpendicular. The idea here is to hold the injector in order to create the lowest pitch. A lack of difference in conductance as well as a relatively high conductance value for both circuits would produce the lowest pitch, thus rewarding the user for holding it firmly and perpendicular to the skin (holding it firmly against the skin increases conductance). Using the difference in conductivity to produce one tone will not tell the user which direction in which the injector is being tilted, but since this constitutes biofeedback, some experimentation in orientation will quickly inform the user the correct (most perpendicular) way to hold the device. Note; the user who is giving themselves a shot in the buttocks would not relate to separate tones for each axis to the direction of their wrist. They would still find out how to correct the orientation by experimentation and listening to or feeling the tones change in pitch, and selecting the position which produced the lowest pitch. Therefore, one tone instead of two separate tones is the simpler solution for the user.

The skin sensing sequence proceeds as follows: Once the device is switched on or woken up from sleep mode and the device is locked into the unfolded position with the lid closed, measurement of conductivity across the gaps between the sensing pads begins. Without contact with the skin, this conductance will be zero and an intermittent note or pulse or tick is sounded at a few cycles per second to let the user know that the skin sensor is working and waiting for contact with the skin. Once the injector is placed against the skin and conductance is detected, the feedback audio signal begins and is changed to a pitch which reflects the conductance difference measured between the two circuits and the relative amount of conductance, thus providing audio feedback as to the degree of flatness in which the skin sensor circuits are being held against the skin and how firmly they are being held against the skin. The biofeedback is a frequency based signal and it could be tone that varies in pitch but has an average value around between 1 kHz and 3 kHz, or other such audio signal which will provide feedback to the patient as to how perpendicular the device is held against the skin. The tone would drop in pitch as the skin sensor circuit detects higher conductance. The pitch is to drop if either the difference in conductances is reduced or the overall conductance increases. Said another way, the tone drops in pitch as the resistance between the pads decreases and the difference in resistance between the two circuits decreases. This is one way of providing the biofeedback, however, other methods could also be devised to vary the audio and haptic vibrations.

Since the resistance of skin can vary widely and this resistance is in series (added in) with the resistances presented by each pad to skin (the variable which provides the positional information), the algorithm can average the conductances measured during the first second of contact and equate that average to the center frequency from which pitch will be varied. It is preferable to provide a selection through the menu system as to what the center frequency of the tone would be. The elderly tend to lose hearing in the lower frequencies, so they may want to select a 3 kHz center frequency tone whereas others may prefer a lower pitch for the center frequency. Next, the algorithm gathers conductance values for a few seconds to develop high and low values. Then, with a data range collected, the lowest quarter of pitch values being produced could be considered as values equated to an adequately positioned injector and pitches equal or lower could be values where the injection initiate button would be enabled. If the conductances start to vary too much after enabling the injection initiate button, the initiate button could be disabled until the injector is held steady. Perhaps three seconds of steady pitch within the lowest one quarter of the data range would be required to enable the injection initiate button.

Once the injection initiate button is enabled, the haptic frequency can continue to provide tactile feedback but the audio tone can be replaced by a "ready" type audio queue such as are provided on smart phones when a message is received. Additionally, the display could present the words "ready to inject" or some other visual confirmation that the injection initiate button has been enabled for the user to press. The audio confirmation could also be a human voice stating calmly "ready for injection" or the voice annunciation could be preceded by a musical queue. Meanwhile, the skin sensing algorithm continues to monitor conductance. If the pitch should raise above the lower 25% limit, and the initiate button has not been pressed, the audio tone could be returned and the algorithm again waits for an audio frequency within 25% of the lowest frequency to be maintained for three seconds, wherein the "ready for injection" audio queue is once again played and the "Initiate Button" is once again enabled.

If the patient should then press the "initiate injection button", the injection is then initiated. During the injection, a ringtone could be played. This ringtone could be customized to fit the age group of the patient. Even during the injection, the skin sense algorithm continues to monitor conductance but without the audio tone however, the haptic vibrational feedback is maintained. This is to insure that the injection is proceeding with the injector held steady and in a perpendicular position by continually providing biofeedback to the user. If during the injection, the algorithm detects a loss or significant reduction in conductance, the injection is aborted and the needle is retracted and the exception handler is notified. How the device handles the fault is provided for under the exception handling algorithm of the supervisory program. Briefly, the needle is retracted, an aborted audio queue is provided, and the "Initiate Button" is disabled. After resetting the device, the injection can be restarted. Resetting of the device can be as simple as opening and closing the lids and pressing a key on the keypad to indicate confirmation of the reset, however, the needle should be replaced and instructions can be provided to the user through the display and by human spoken language that this needs to be done prior to restarting or resuming the injection. Since any drug that didn't get injected due to the injection being aborted is still in the syringe, the injection can be re-initiated. Typically the injection would be re-initiated in a new spot, and with the "ready" signal once again obtained; the "Initiate Button" can be enabled. The patient will of course be prompted to change needles before re-attempting if they so prefer. Some needles become dull with just one usage. Generally speaking, exceptions such as the above described fault will be accommodated with audio in the form of human voice so that instructions on proper recovery and completion of the dosage are made very clear to the patient.

The TENS (Transcutaneous Electrical Nerve Stimulation) function supplies pulses of electrical energy through the skin near the site where the needle enters the skin and in this way, disrupts the perception of pain by the brain. In particular, pulses of 20 milliamps at 200 Hz with a 200 micro second pulse width have been shown, when administered near the site of pain, to block the sensation of pain in the brain by stimulating a type of nerve fiber (called A-beta) that carries signals relating to touch. Different fibers (called A-delta and C fibers) carry the transmission of pain. The signals from the A-beta touch sensation fibers travel to the spinal cord where they temporarily block the transmission of pain from travelling up the spinal cord to the brain where pain is perceived. This is known as gate control theory.

The TENS function is administered through the same electrically conductive pads as the skin sense technology uses to measure the position of the injector on the skin. The TENS function is administered for approximately one second before the needle is extended from the injector and during the dispensation of medicament and during any dwell time (see below). The TENS happens at the same time as the skin sense algorithm operates by multiplexing the electrically conductive pads onto the appropriate circuitry. The switching happens several times per second. A measurement of the skin's conductivity in the x and y dimensions are made followed by a hundred milliseconds of TENS and then back to measuring skin conductivity, and back to TENS, and so on. In this way, pain of injection can be blocked while the biofeedback is provided to the operator as to the placement of the injector on the skin.

Distraction and can lessen injection anxiety. The doctor often has the patient look away when giving an injection. This is a form of distraction. With this invention, due to the biofeedback, the patient giving themselves an injection doesn't have to even watch the injector. Even if they did look at it, the syringe and the needle are completely hidden from view during the entire process. This invention provides several additional layers of distraction. Ringtones can be sounded when the injection initiate button is enabled and when the injection is finished and a musical theme can be played during the injection. Research has shown that music heard by a patient with Otitis media undergoing the procedure of tympanostomy tube insertion have a reduced reflex jerk when music is played into the ear. This injector can also reproduce a calm physician voice instructing them to relax and listen to my voice as I count. The voice produces a distraction while the counting lets them know how long to hold still. The haptic vibration which provides biofeedback to the patient informing them as to how well they are holding the injector against their skin. This vibration continues during the injection process. This vibration also provides another layer of distraction. The TENS function produces a mild touch or sensory sensation which provides a distraction while the needle is being inserted and while it is in the skin. To this inventors knowledge, no TENS function has ever been combined with an injection device to either block pain or provide a distraction during needle insertion or while the medicament is being dispensed. Therefore, these novel features embodied in this invention provide an injection experience of less anxiety for the patient, and less anxiety results in fewer incidents with injection and better patient compliance.

The human spoken language facility of the injector is accomplished by recording actual spoken language and compressing it for later playback. The human language is stored in a separate flash memory along with the ringtones and other audio queues. Two royalty free methods of encoding human speech are the Speex and G.726A standards. Both codecs (encoder decoder) are made for high quality speech and both have libraries made for the C30 compiler that is supplied with the dsPIC DSC (Digital Signal Controller) MCU chosen for this application. This particular MCU, besides containing PWM, ADC and other modules, also contains a stereo DAC (Digital to Analog Converter) and special math functions for digital signal processing such as speech and music decoding and playback. These resources were part of the reason this particular MCU was chosen. The digital signal processing capability was a primary consideration in that high quality speech reproduction in any language is required to effectively communicate to the user of the injector. Likewise, the built-in stereo DAC produces high quality sound. Only one channel of the DAC will be used as this device is hand held and stereo wouldn't provide an advantage over monaural audio. The DAC output is input to a class D monaural audio amplifier which is very efficient and has a high signal-to-noise ratio. Last in the audio chain is a high quality speaker.

The speech will be spoken by professionals in their native language and recorded in a sound booth. These recordings are then encoded in either the Speex or G.726A formats and stored in the separate flash memory. The decoder is compiled with the rest of the program code.

The injector will normally hold one or two language sets, such as English and Spanish, space permitting. If a language needs to be changed, a new language set can be downloaded by a personal computer through the USB port. Likewise, new ringtones (musical themes) can be downloaded from a personal computer if the user would like to customize their injector. All the audio is stored in the flash memory. Audio tones are not stored by generated by program code and sent to the DAC.

The display/keypad function together to provide a menu/input system. The display when functioning as a menu system will typically display the current menu in a top row of text and the current choice under that menu item in the second row of text. Choices under that menu scroll sideways when the left and right arrow buttons are pressed. The up arrow takes the user up one level of menu and the enter button selects the currently displayed choice in the bottom row. When not displaying the menu system, the display would be displaying directions such as would be appropriate when an injection is being performed or when an error has occurred.

The following is a possible menu system which would encompass many of the features embodied by this invention.

| | | Reminder Alarms | | |
|---|---|---|---|---|
| Set | Delete | Delete All | | |
| | | Needle Insertion | | |
| Slow | Medium | Fast | | |
| | | Dispensing | | |
| General | Shear Sensitive | High Viscosity | Fast | Slow |
| | | Post Dispense Dwell | | |
| General | Custom | While in Contact | | |
| | | Bio-Feedback* | | |
| Spoken | MP3 | Tones | Haptic | None |
| | | Human Language | | |
| English | Spanish | Etc. | | |
| | | Audio Theme | | |
| General | Child | Adolescent | Teen | Custom |
| | | Audio Volume | | |
| Voice | Tones | | | |
| | | Audio Tone Center Frequency | | |
| 1 kHz | 2 kHz | 3 kHz | | |
| | | Injection Practice | | |
| ON | OFF | | | |
| | | TENS Settings | | |
| OFF | ON | Adjust General | Intensity Pulse Rate | Pulse Duration |
| | | Aspirate Analysis | | |
| OFF | ON | Adjust Sensitivity | | |
| | | Syringe Selection | | |
| BD Luer 1 ml. plastic | Terumo Luer 1 ml. plastic | Etc. | | |

*Note:
Biofeedback Modes:
Spoken includes MP3, Tones, and Haptic
MP3 includes Tones and Haptic
Tones includes Haptic
Haptic is just Haptic
None is no biofeedback.

Aspirate Analysis is a check for blood in the syringe as an indication that a vein has been accidentally been pierced. Some drug "Full Prescribing Information" instructs the patient to aspirate the syringe by drawing back on the plunger and checking for blood in the syringe. This is often because the manufacturer doesn't want the drug to directly enter the blood stream. If the result is positive, the manufacturer instructs the patient to stop the injection and select another spot for the injection.

The aspirate analysis function provides for automatic check for blood in the syringe. Many patients are made uneasy or even faint at the sight of blood. The aspirate analysis function provides the check without the patient having to perform the aspiration or having to view the syringe. As described above, the syringe plunger is drawn rearward approximately 5 to 10 mm which creates a vacuum. The process pauses for a couple of seconds to allow fluid and/or blood to enter the syringe barrel. Then the aspirate is checked optically for the presence of blood. If blood is detected, the injection is aborted and the needle is withdrawn and the user is informed that the aspirate contains blood via the display and spoken language if the human language mode is enabled. The display and optionally human voice would instruct the patient to change the needle, confirm the needle replacement, and to then pick a new spot and re-initiate the injection. If blood is not detected, the injector would inform the patient that "no blood detected in aspirate" and the dispensing of the medicament would proceed.

Reminder Timers are alarm functions for scheduled injections. Multiple alarms can be set for any time. A special ringtone sounds when each alarm becomes due. The alarm rings for a length of time such as up to two minutes and silences or sooner if acknowledged by the user. If not acknowledged by the user, the alarm could resound a time such as fifteen minutes later. If still not acknowledged, the alarm could continue resounding on a reoccurring basis. The alarms can be set on the injector using the menu system or they can be downloaded from a personal computer application that features an on-screen calendar for easy patient interface. In the on-screen calendar, the user has the opportunity to note what drug and amount they are to take. When the alarm becomes due, the note they wrote themselves will appear on the injector display. If using the personal computer interface to access the alarm function, the user has the opportunity to download a different reminder audio alarm (ringtone) should they prefer their own over the default one provided with the injector.

The exception handler is a type of state machine that controls the machine and instructs the user when problems occur. These could be operator error problems or problems with the devices functioning. With the facilities of the display and especially the human spoken language instructions, it is possible to succinctly handle a variety of problems that could arise with an injection or the operation of the injector that could not be handled well with other injectors.

BRIEF DESCRIPTION OF THE DRAWINGS

Preferred embodiments of the present invention will now be more particularly described, by way of example only, with reference to the accompanying drawings in which two primary embodiments are depicted, herein referred to as the 'syringe guide embodiment' and the 'disposable needle shield embodiment'. The 'syringe guide embodiment' refers to an embodiment which has a removable syringe guide and the 'disposable needle shield embodiment' refers to an embodiment which has a disposable needle shield which contains a needle guide (no syringe guide is required) and the needle shield is replaceable and disposable.

FIG. 14 is a sectional view of the distal end of the 'disposable needle shield embodiment' looking toward the needle from the front (looking proximal) with a portion of the GG section shown for reference. Since it is a sectional view, the Skin Sensor Contact Support 64 and the Skin Sensor Contacts 65 are not pictured. Rather, the molded-In Conductors 60 are pictured. These lead to the Skin Sensor Contacts 65.

FIG. 15*a* is a sectional view through the Syringe Section Housing 69 with an inserted syringe in place and looking distally down the needle axis of the 'disposable needle shield embodiment' from section HH with a portion of the GG section shown for reference.

FIG. 15*b* is a sectional view through the Syringe Section Housing 69 with an inserted syringe in place and looking distally down the needle axis of the 'disposable needle shield embodiment' from section JJ which cuts through the Elastomeric Flange Grip; a portion of the GG section is shown for reference.

Subsequent FIGS. 24, 25, 26, 27, and 28 respectively, further illustrate the details of these sections. Note: most bypass capacitors and some other discrete passive components are not illustrated.

Figure 23:
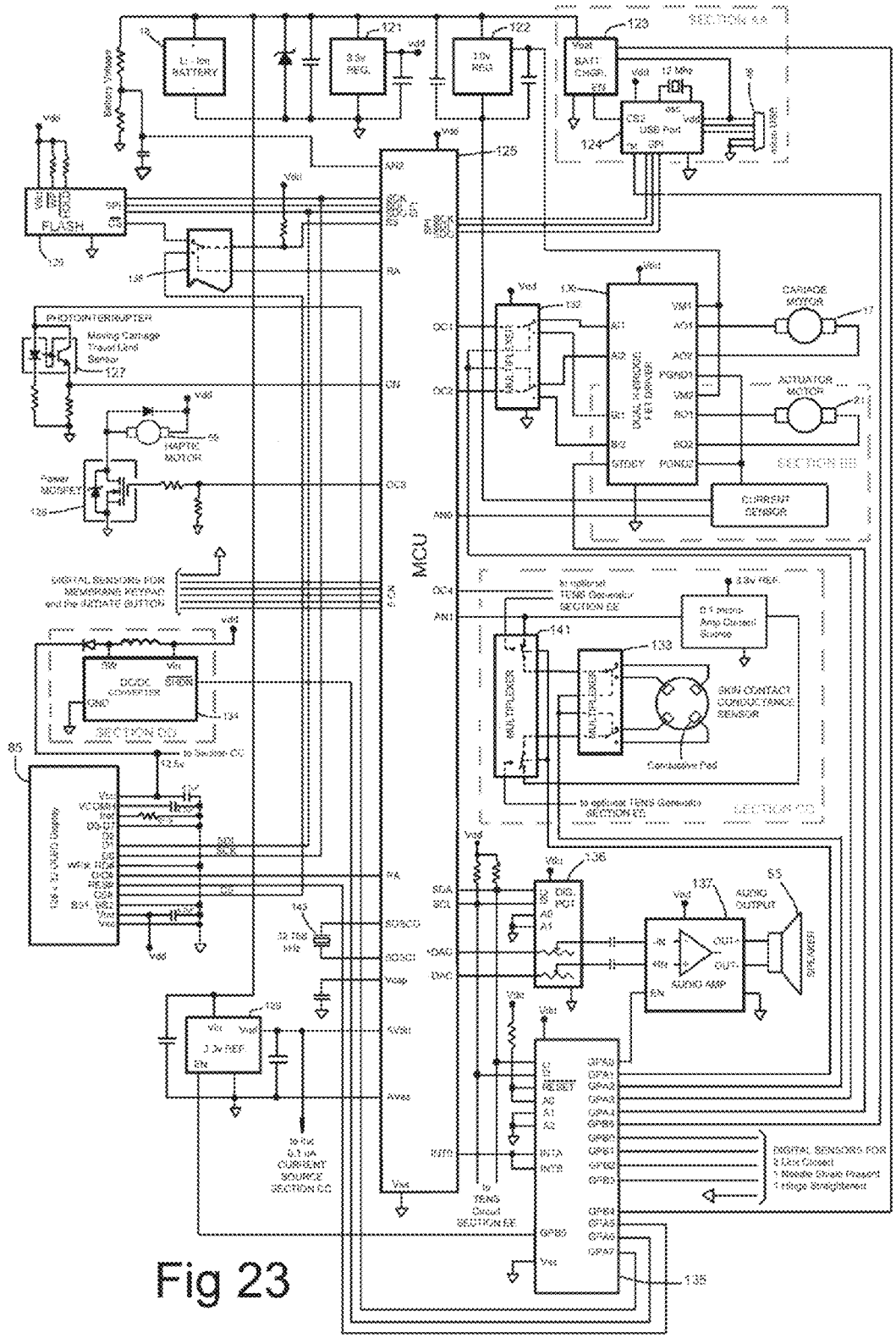
FIG. 23 is an electrical schematic of the major electronic components and their interconnection of the autoinjector with the primary focus from the perspective of the Integrated Circuit Board 19. The electrical schematic is virtually the same between the two primary embodiments of the invention. Some electronic detail is shown in simplified form in sections marked CC, BB, AA, DD, and the TENS circuit.
Figure 24:
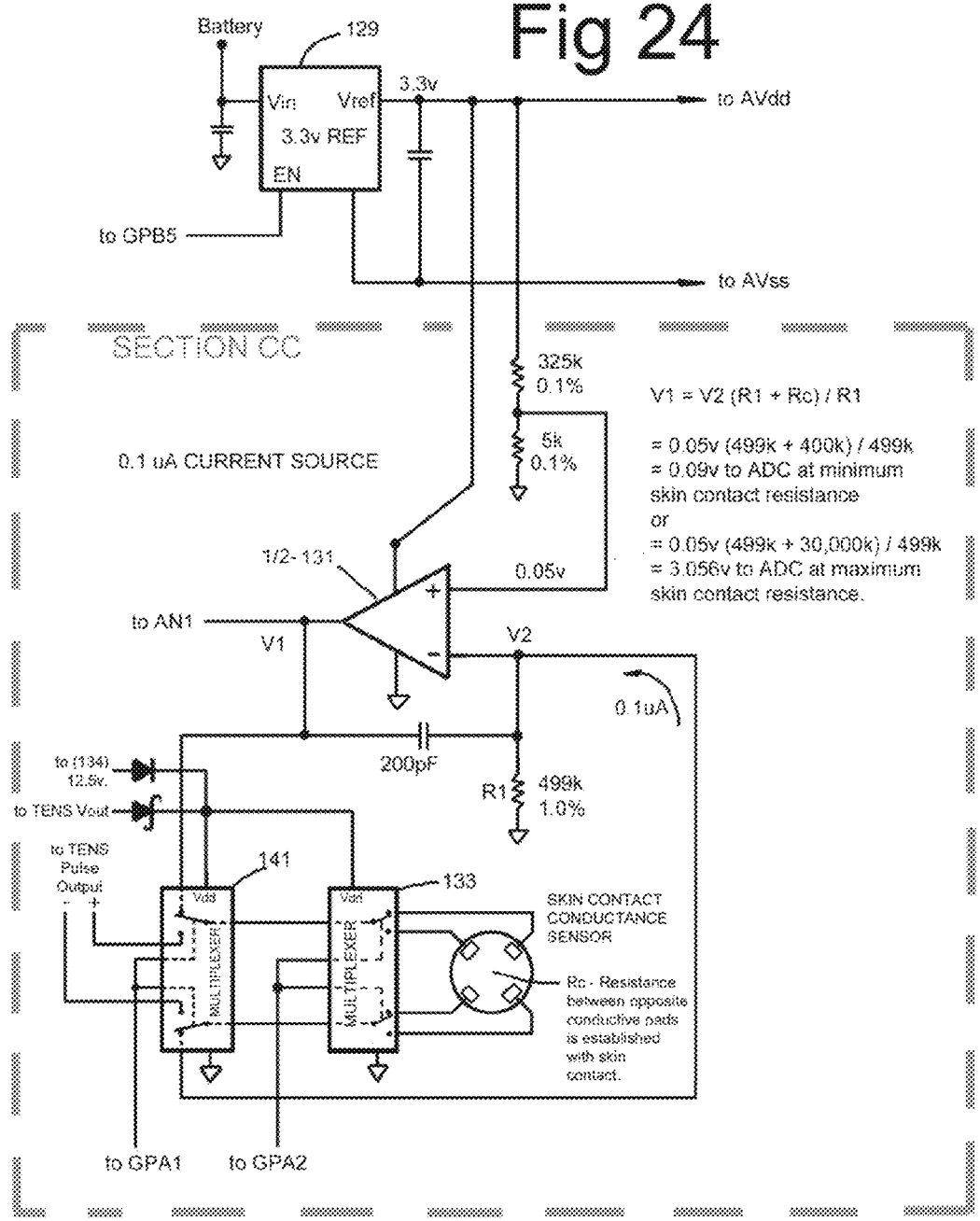

FIG. 24 is a detail of Section CC as illustrated in FIG. 23 and in particular, it details the 0.1 microamp current source circuitry which is used to measure skin contact conductance.

Figure 25:
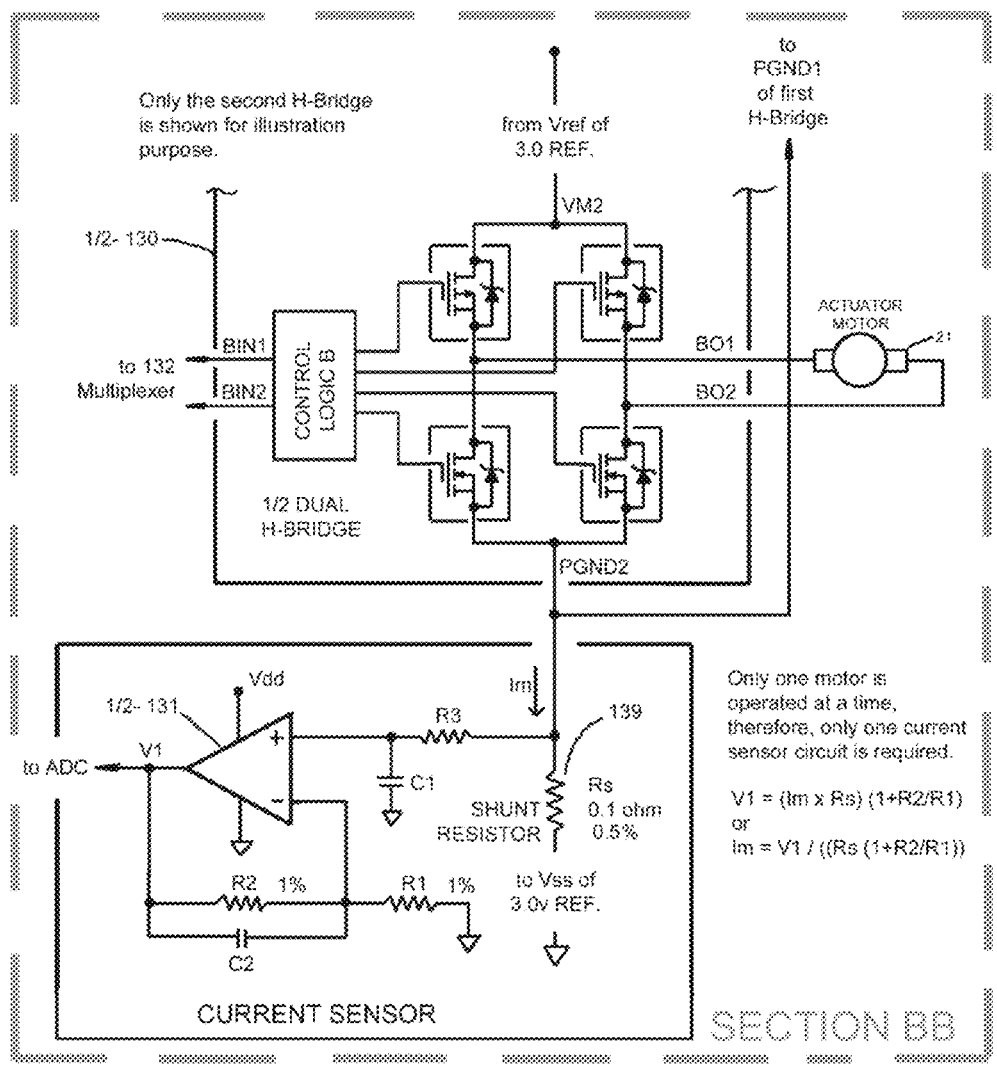

FIG. 25 is a detail of Section BB as illustrated in FIG. 23 and in particular, it details the current sensor circuitry which is used to measure the torque and speed of the motors.

Figure 26:
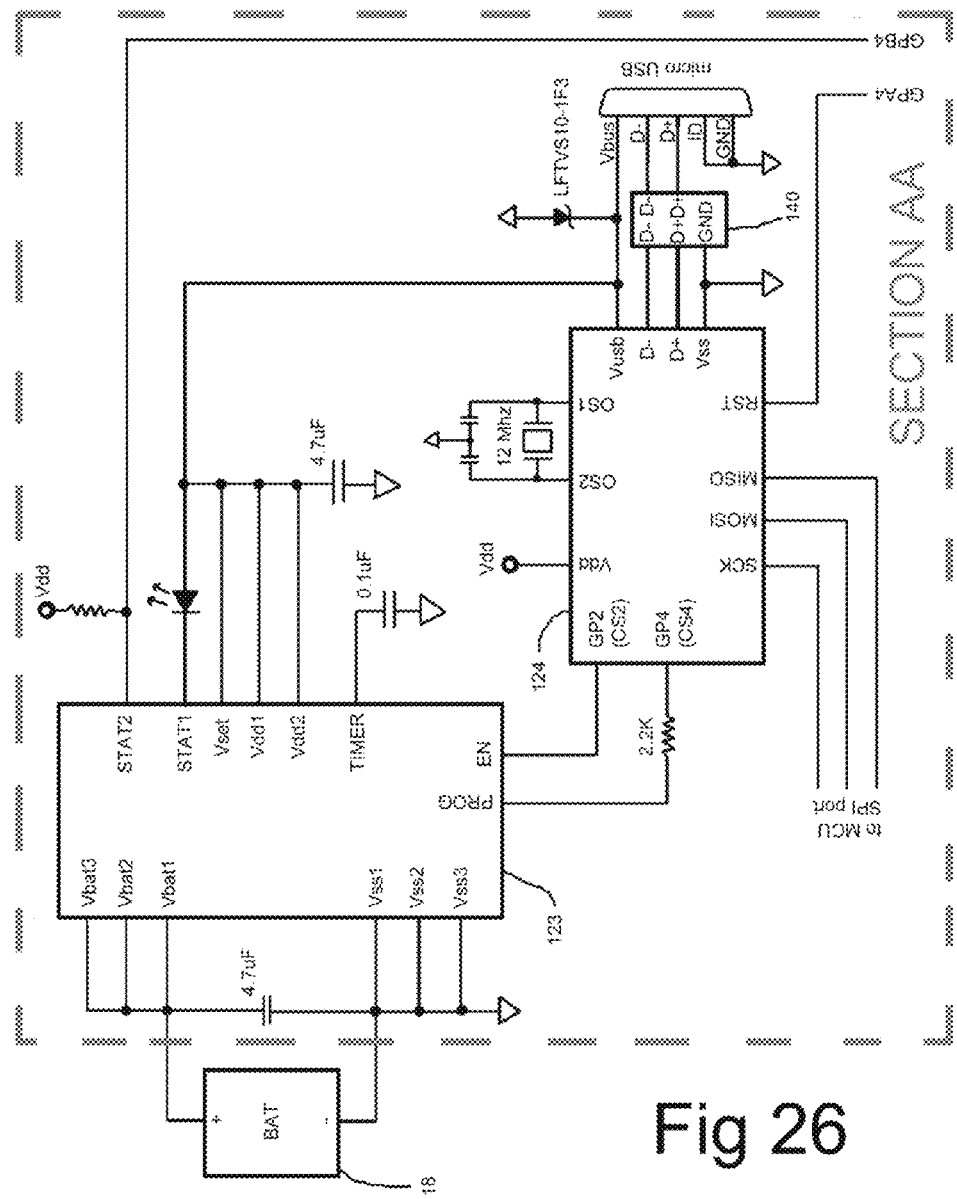

FIG. 26 is a detail of Section AA as illustrated in FIG. 23 and in particular, it details the battery charging circuit which works in concert with the USB to SPI protocol converter. The USB port signals if it is providing high or low current capacity and this information is used to control the charging circuitry appropriately.

Figure 27:
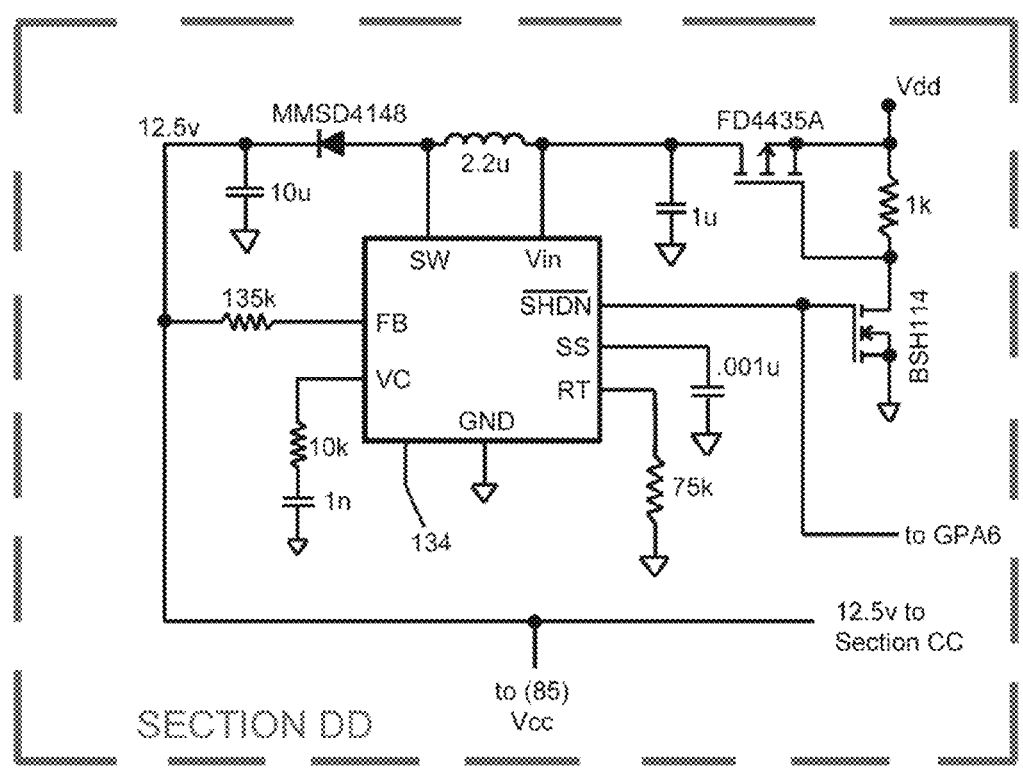
Figure 28:
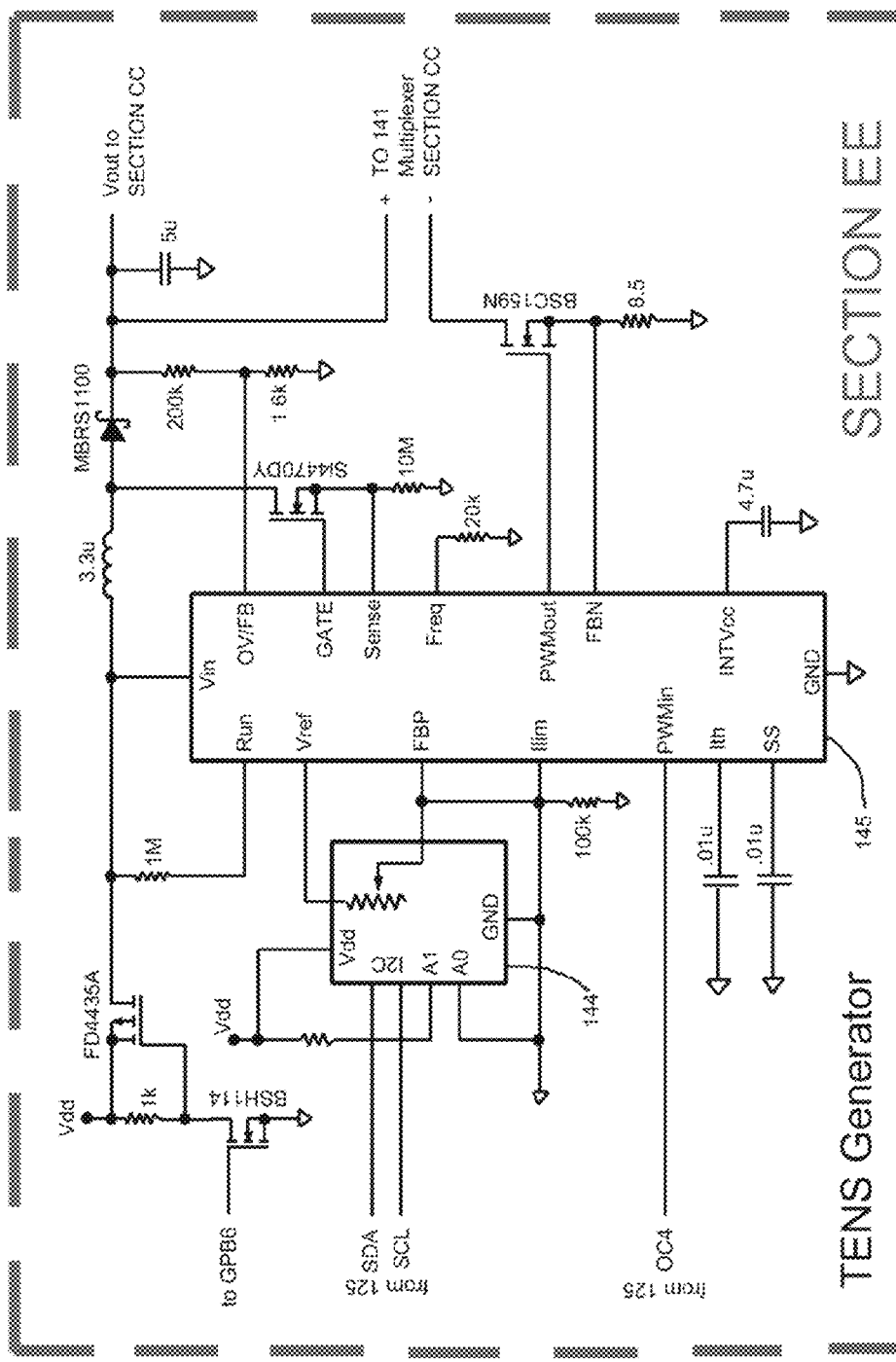

FIG. 27 is a detail of Section DD as illustrated in FIG. 23 and in particular, it details the DC to DC converter which supplies 12.5 volts to the Vcc pin of the (85) OLED display and power to the multiplexers of SECTION CC FIG. 28 is a detail of the TENS circuit which is multiplexed onto the skin sense electrically conductive pads. This circuit is a DC to DC converter whose output is chopped into a PWM output. The output is adjustable in frequency, pulse width, and intensity.

FIG. 29 Motion control feedback and feed-forward algorithm.

DETAILED DESCRIPTION OF THE DRAWINGS

Figure 1:
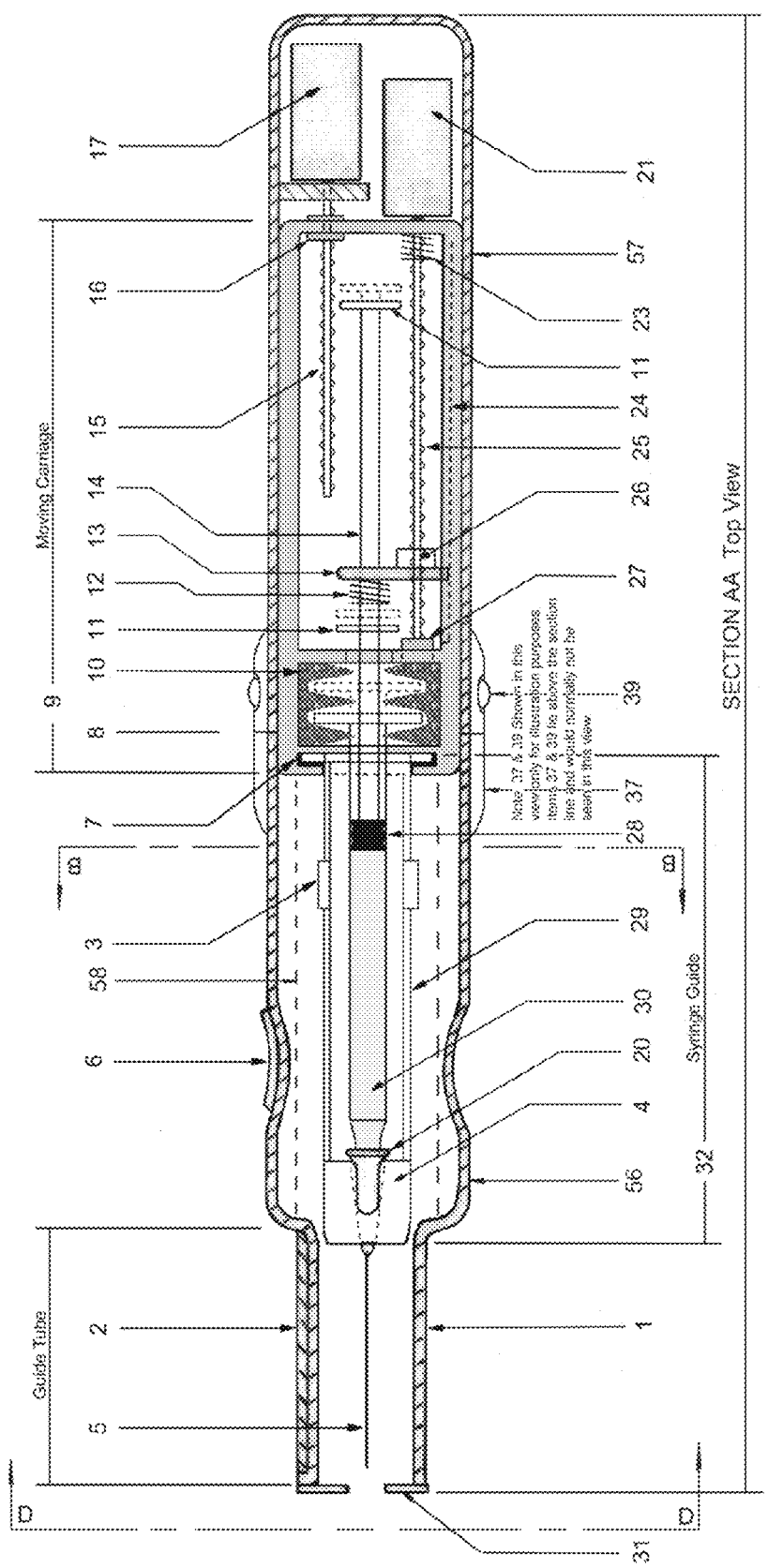
FIG. 1 is a sectional view of a 'syringe guide embodiment', looking down from the top with the upper partition from the section AA removed. That is, the injector is cut horizontal down the needle axis to illustrate the parts within from an overhead perspective.
Figure 2:
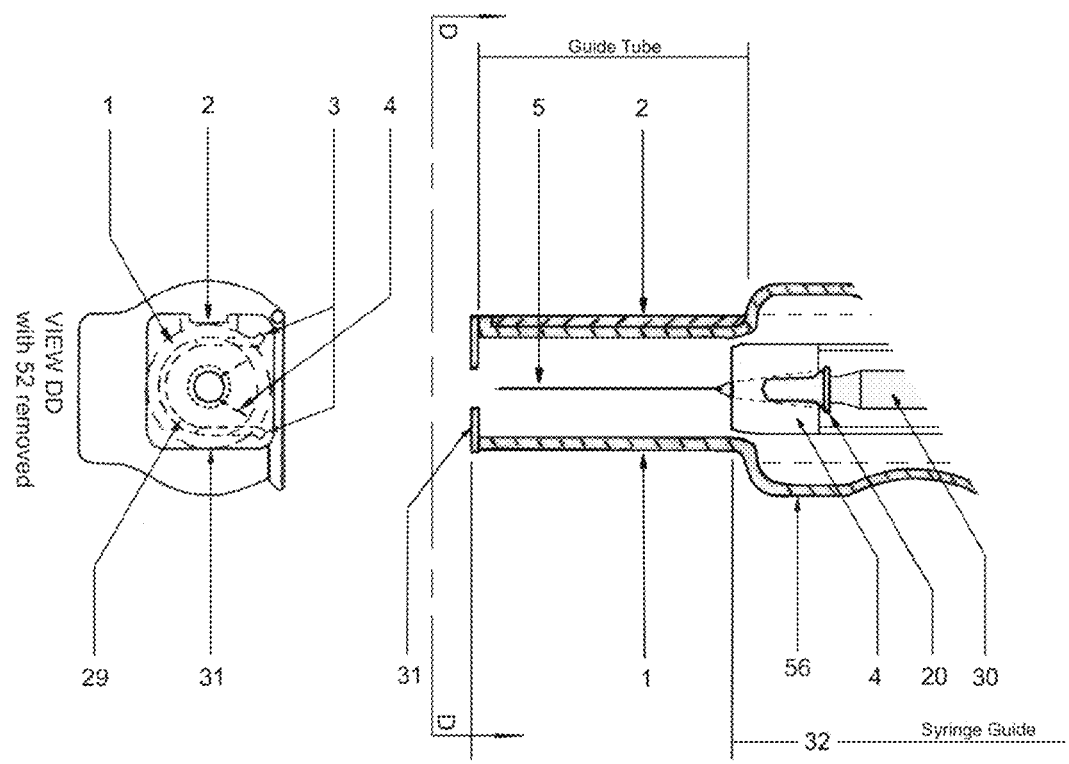
FIG. 2 is an end view of the 'syringe guide embodiment' looking toward the needle from the front (looking proximal) with a portion of the AA section shown for reference. It is pictured with the Skin Sensor Printed Circuit 52 removed thus looking at the Skin Sensor Support 31.
Figure 9:
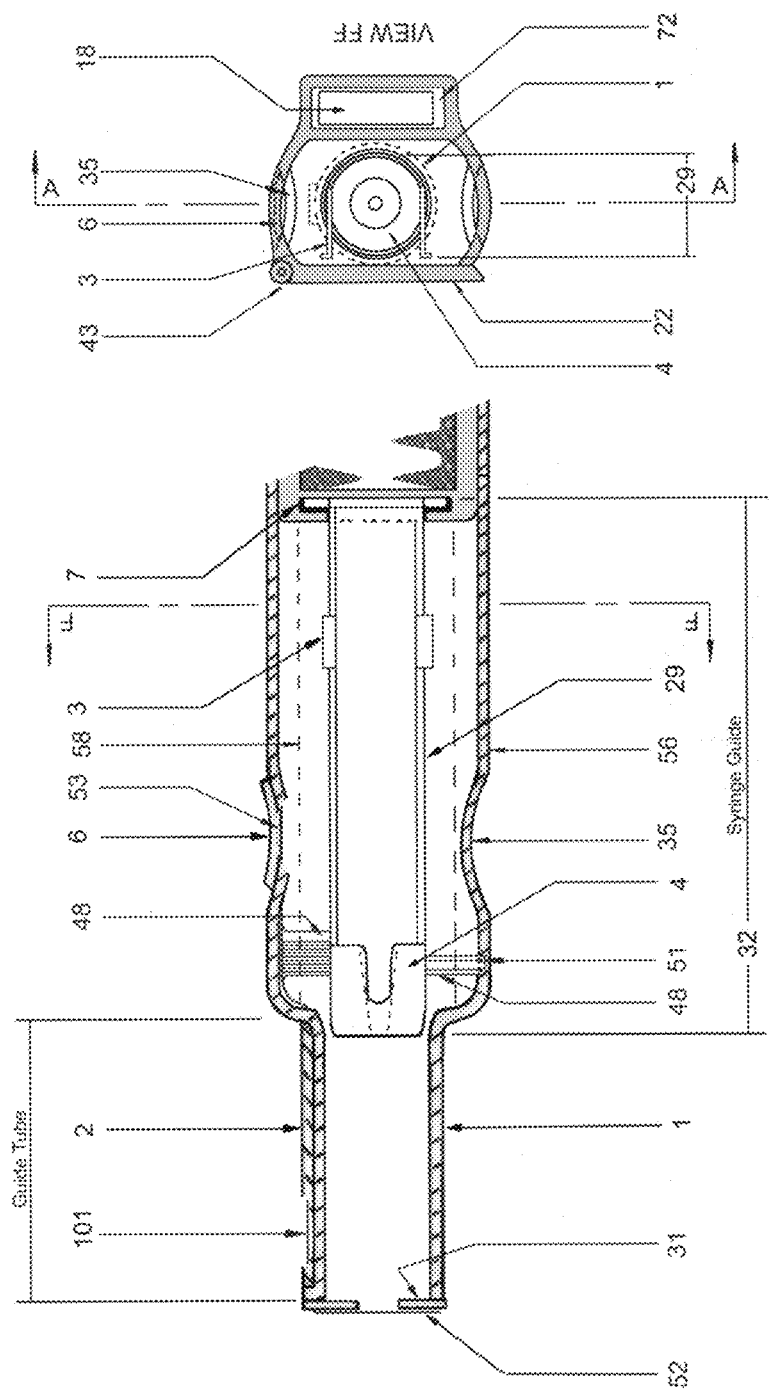
FIG. 9 is a sectional view through the Syringe Guide 32 of the 'syringe guide embodiment' without the syringe pictured. This view aids in depicting the distal end where the syringe needle (attached to the syringe) is inserted since the syringe is removed from the view. A portion of the top sectional view AA is included for reference.
Figure 10:
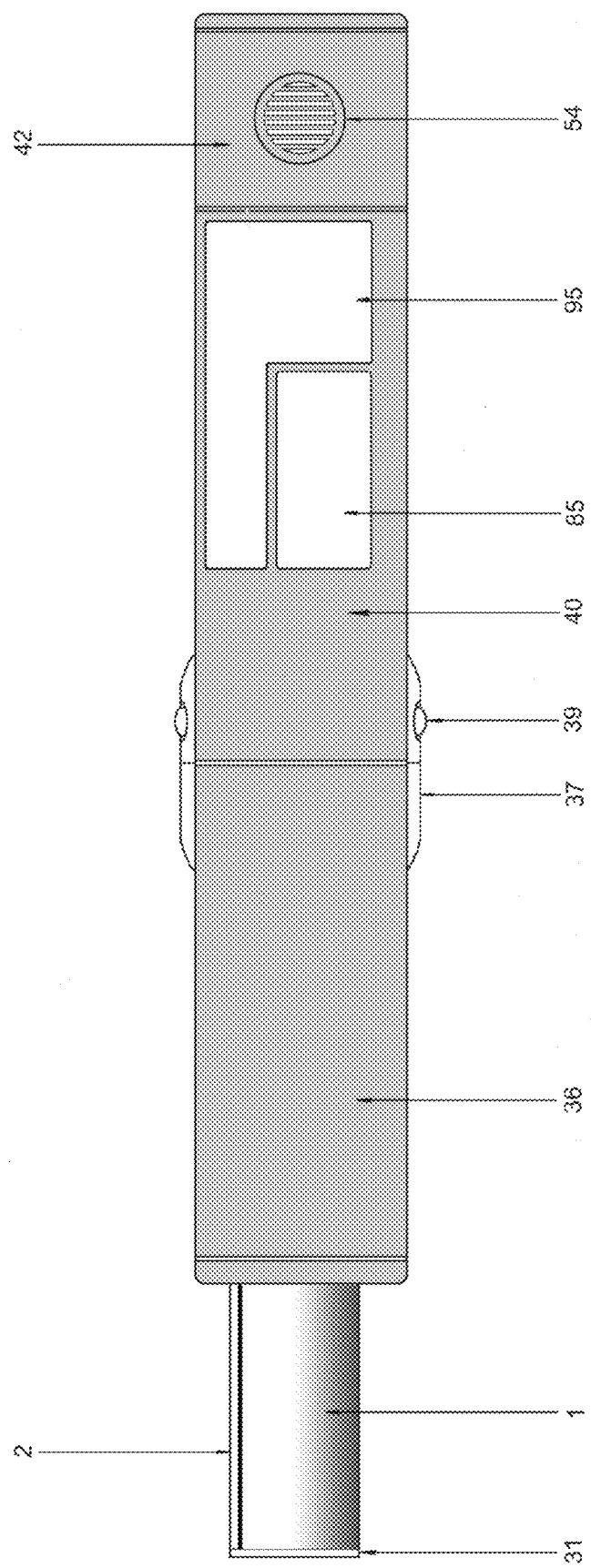
FIG. 10 is a non-sectional top view of the 'syringe guide embodiment' of the invention with the distal (needle) end on the left and the proximal (motor section) end on the right, which depicts the Access Covers 36 and 40 along with the Operator Display 85 and Speaker Grill 54 locations.
Figure 11:
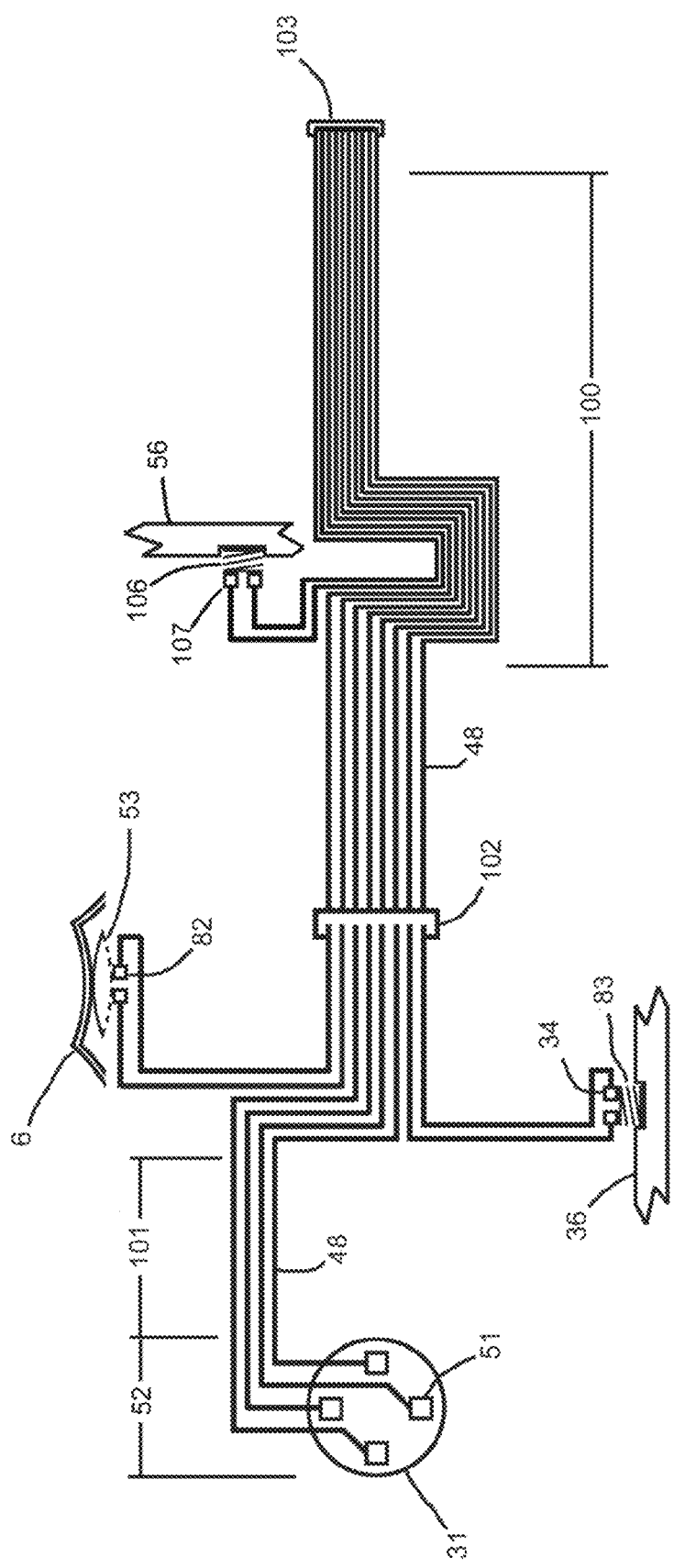
FIG. 11 is an illustration of the Flexible Electric Circuit 48 that is part of the 'syringe guide embodiment' which contains at its extreme distal end, the Skin Sensor Printed Circuit 52 and also contains as part of its circuitry, the discrete digital inputs from the Access Cover, Syringe Section 36, the Initiate Button 6, and the Unfolded and Latched Sensor 107.

FIGS. 1 through 11 exclusively depict the 'syringe guide embodiment' of the invention. FIG. 1 is a sectional view of a 'syringe guide embodiment', looking down from the top. The guide tube 1 is part of the overall housing mold, but cylindrical in shape. The skin sensor support 31 is part of the guide tube 1 or it can be a separate piece consisting of a printed circuit board. If it is a printed circuit board, it will contain the conductive pads 51 of the skin sensor circuitry. Most preferred however, the skin sensor support 31 is part of the housing guide tube 1, and the conductive pads 51 are part of the skin sensor printed circuit 52 (see FIG. 2, view DD and FIG. 11) which is part of the flexible electric circuit 48. An extension 101 (see FIG. 11) of the flexible electric circuit 48 passes from the inside of the distal portion of the housing through the wire way 2 (see FIG. 2, FIG. 5, and FIG. 9) to reach the outside surface of the skin sensor support 31. Especially in FIG. 9, one can see the skin sensor printed circuit 52 on the outside of the skin sensor support 31. A cutaway of the wire way 2 shows the flexible circuit extension 101 threading back to the main body of the flexible electric circuit 48. One can also see the flexible circuit passing underneath the syringe guide 32 to reach the access cover closed sensor, syringe section 34. The flexible circuit 48 is also shown laying flat against the inside wall to reach the tactile initiate switch 53 which consists of the snap dome sensor 82 and the snap dome 53. Referring to FIG. 11, the flexible electric circuit 48 is shown in shape but not to scale. The circuit is die cut from a solid piece of plastic that has been printed with electrical conductors (traces) and the arms of the circuit are so shaped that they can reach each of the sensors that it connects to by laying flat against the inside of the housing. The flexible circuit serpentine 100 is shaped so that it can coil through the folding hinge 49 to reach the integrated circuit board 19 where it is attached by the flexible circuit connector 103. Note, the skin sensor printed circuit 52, the flexible circuit extension 101, and the flexible circuit serpentine 100 are all part of the flexible electric circuit 48. The flexible electric circuit 48 enters the battery and vibrator compartment 72 (see FIG. 9) through a slit 102 between the upper and lower compartments of the guide tube/syringe guide housing 56 so that it can serpentine through the folding hinge 49 and terminate onto the integrated circuit board 19 which resides in the electronics bottom compartment 33 of the moving carriage and electronics housing 57.

Figure 3:
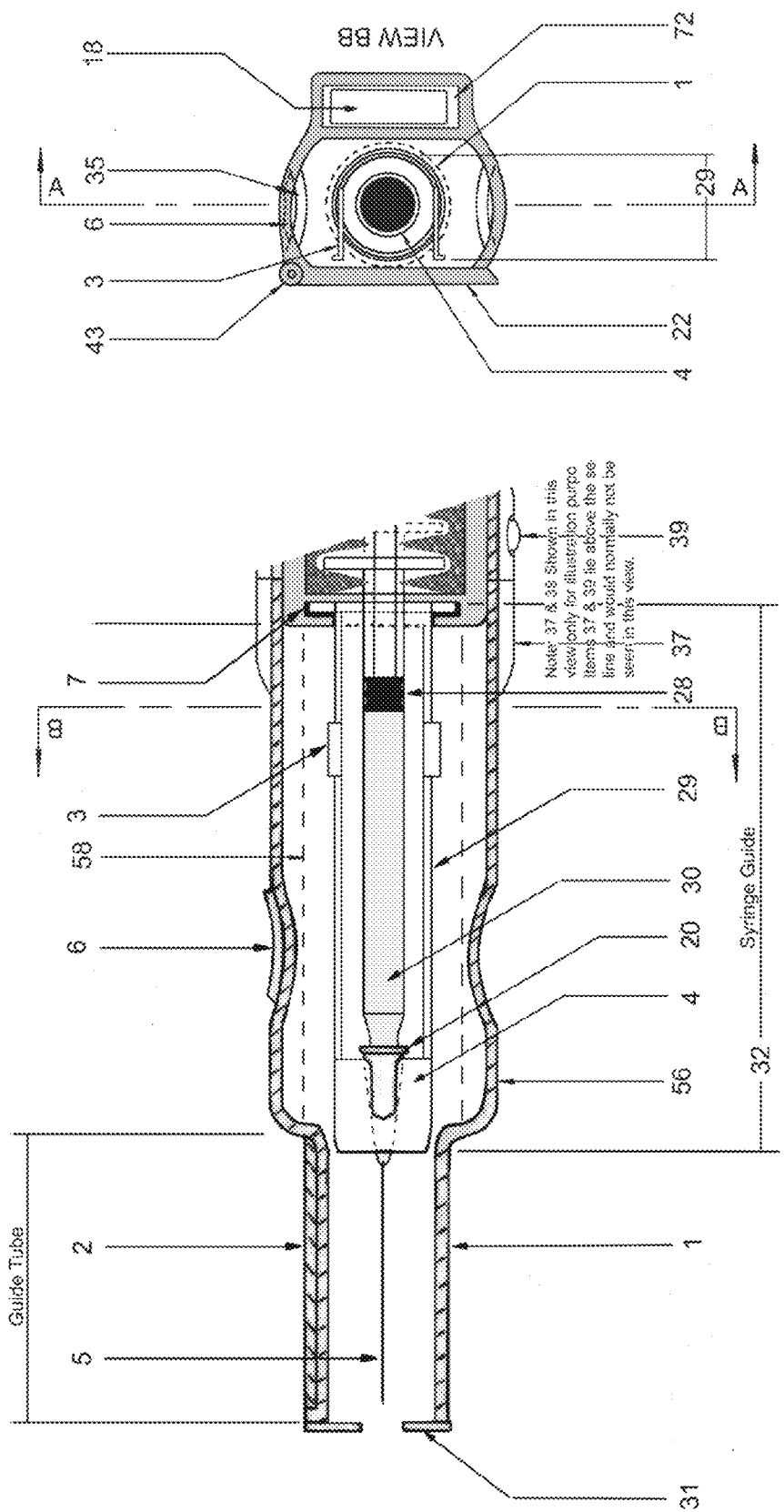
FIG. 3 is a sectional view through the Syringe Guide 32 looking distally down the needle axis of the 'syringe guide embodiment' with a portion of the AA section shown for reference.

The needle centering fixture 4 which is part of the syringe guide 32 holds the distal end of the syringe at the center of the guide tube 1 so that the needle 5 is guided straight out the center of the distal end of the injector. The needle centering fixture 4 is also molded so that the distal end of a glass syringe or the needle connector 20 of a Luer type removable needle (pictured in FIG. 1) for which the syringe guide 32 design is illustrated, fits snugly within its interior shape. Said another way, the needle centering fixture 4, which is part of the syringe guide 32, is molded of plastic with an interior shape which is made for a particular standard or non-standard syringe/needle combination. If the syringe guide 32 is made for glass syringes, the needle centering fixture is actually holding the end of the glass syringe and centering the needle by centering the end of the syringe. If the syringe guide 32 is made for removable needles, the needle centering fixture is holding the needle connector 20 and centering the needle by centering the needle's connector 20 while it is attached to the syringe 30. Specific syringe guides 32 are made for specific syringe/needle combinations. Likewise, the diameter of the syringe guide 32 and in particular, of the 140° semicircle 29, which is the major length of the syringe guide 32 is of such width to accommodate the diameter of syringes the needle centering fixture 4 is designed to accommodate. Said another way, the needle centering fixture 4 may accommodate a range of syringe diameters, for example, such as with 1 and 3 ml luer slip syringes where the distal end of the syringe is a standard luer slip shape, yet the diameter of the syringe occurs in two sizes (1 ml and 3 ml). The 140° semicircle 29 is then designed of such diameter to accommodate either syringe. Specifically, the diameter of the 140° semicircle 29 is of such size that the barrel of the syringe 30 doesn't touch the syringe guide. This is one variation of the syringe guide 32. Many other syringe guides can be fashioned to accommodate different syringe/needle combinations. Thus, to change from one needle/syringe standard to another, only the syringe guide 32 needs to be changed, and perhaps the elastomeric flange grip 10 (discussed below). Referring to FIG. 3, view BB, a section provides a view looking at the syringe guide 32 looking distal. The center black circle is the syringe plunger seal 28 and the circle around it is the needle centering fixture 4 snugly fit to the syringe distal end. The next circle drawn outward from the needle centering fixture 4 is the 140° semicircle 29 and the attached syringe guide grip 3, which is two ears or protrusions extending up from the 140° semicircle 29. The syringe guide grips 3 are provided t grip and remove the syringe guide and the syringe 30 with it. Referring to FIG. 9, view FF, a section provides a view looking at the syringe guide 32 looking distal but without a syringe in place. The central item is the needle centering fixture 4 with the needle exit hole shown as the small central circle and the interior fit for a Luer type needle shown as a circle around it. The next structure moving outward is the wall of the syringe guide 32 with the syringe guide grip 3 shown extending upward toward the access cover 22. Notice that the syringe guide 32 just barely fits into the guide tube 1, whose outer wall is shown as the dashed line. Note in the sectional top view of FIG. 9 that the distal end of the syringe guide 32 is tapered a bit and the proximal opening of the guide tube 1 is flared just a bit. This is to provide for easy insertion of the syringe guide 32 into the guide tube 1, after which, the syringe guide flange 7 is inserted into the slot at the front of the moving carriage 9.

Figure 7:
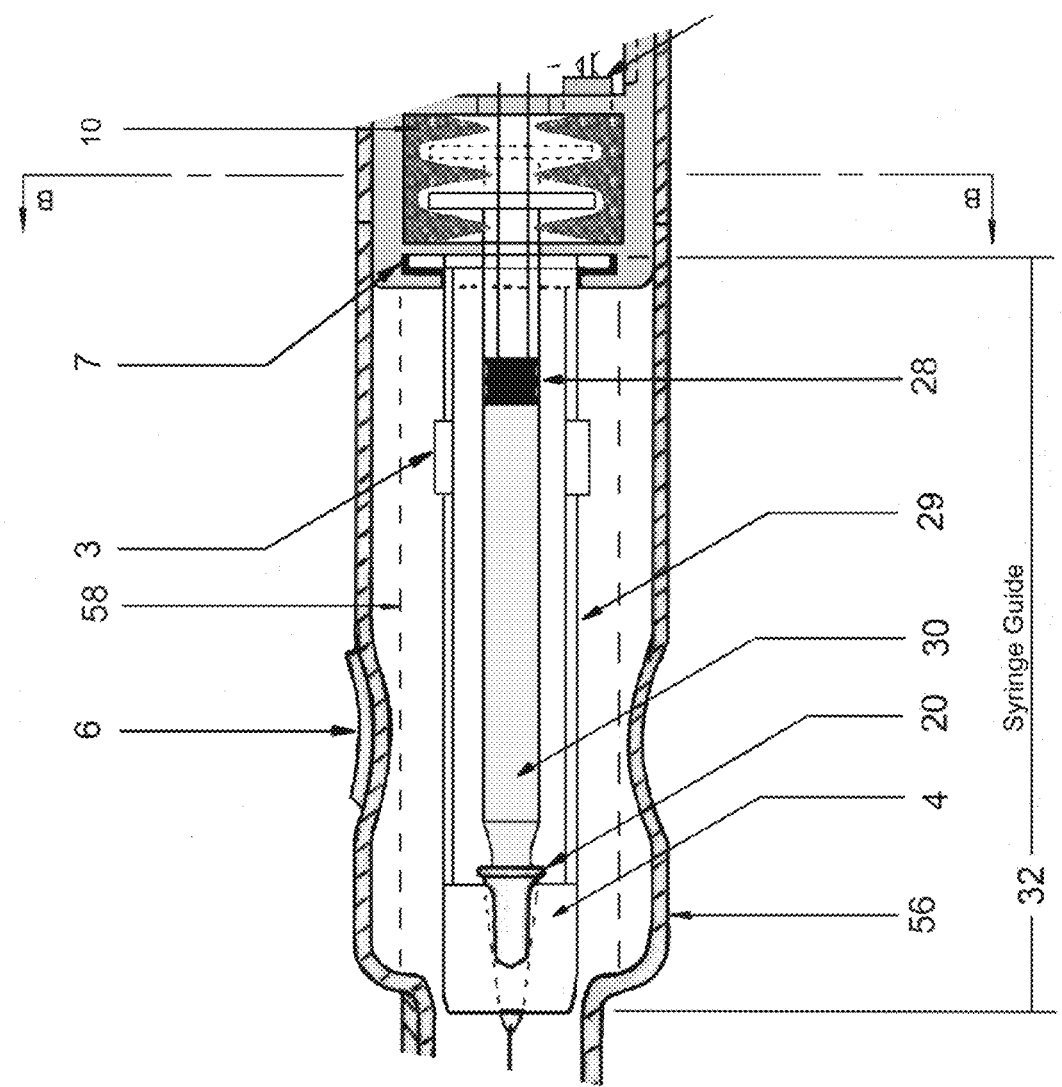
FIG. 7 illustrates the Elastomeric Flange Grip 10 as it grips the Syringe Barrel 91 and the Syringe Flange 92 by showing a sectional view through the Moving Carriage 9 where these parts are located. A portion of the top sectional view AA is shown for reference. The Elastomeric Flange Grip 10 is found in both major embodiments of the invention and so this illustration will not be repeated for the second primary embodiment of the invention, the 'disposable needle shield embodiment'.

Note that the syringe guide 32 is not sized to accommodate the length of syringe 30. The proximal end of the syringe guide 32 ends in the syringe guide flange 7 which slips into a slot at the front of the moving carriage 9 and the syringe body extends further rearward into the moving carriage 9. Referring to FIG. 7, the elastomeric flange grip 10 is the part which accommodates the length of the syringe cylinder by providing a gripping action on the syringe finger flange 92. As shown by view BB elastomer & syringe, the elastomeric flange grip 10 also provides a grip of the syringe cylinder (in addition to gripping the finger flange 92). This keeps the proximal end of the syringe stationary and centered in the x and y dimensions, with the z dimension being the longitudinal axis of the injector or essentially, the needle 5 axis held by the fins of the elastomeric flange grip 10. Said another way, the proximal end of the syringe 30 is held from moving in the z dimension (forward or rearward) by the fins of the elastomeric flange grip 10. The fins in these figures show their location to accommodate BD and Terumo Luer slip 1 ml plastic Tuberculin syringes; however, different elastomeric flange grips 10 with different fin locations and shapes could be designed to accommodate syringes who have their finger flanges 92 at different lengths on the syringe barrel. It is easy to see that by moving the fins a small amount and/or by varying their x and y cylinder gripping dimensions, and considering that they are elastomeric which flexes to different shapes, that a few versions of elastomeric flange grips 10 could accommodate a large variety of standard and non-standard syringes 30 of various lengths and diameters. To this inventor's knowledge, the arrangement where the distal end of the syringe/needle combination is held by a conformational guide that is attached to a pushing/pulling member which holds an elastomeric part which holds the proximal end of the syringe, has never been done or patented.

Figure 4:
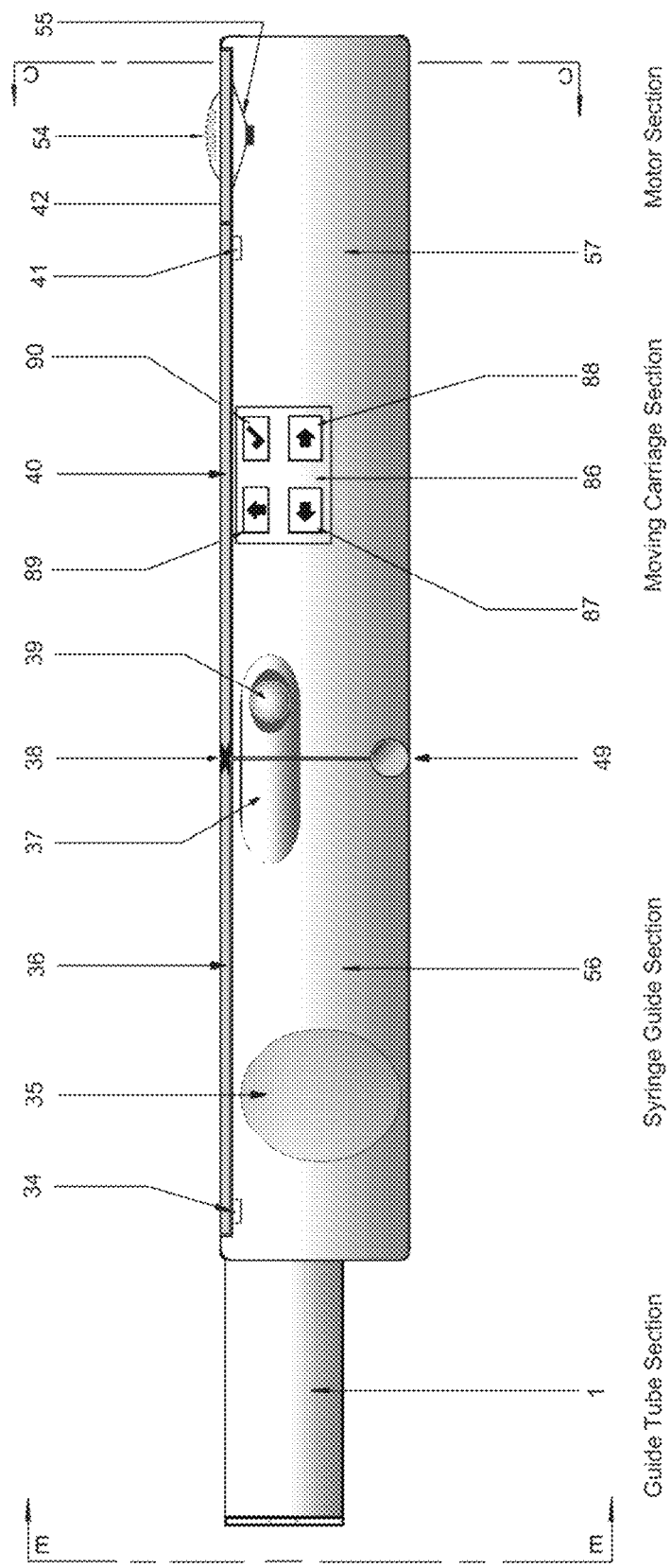
FIG. 4 is a side view of the 'syringe guide embodiment' with the needle (distal) end to the left, and the motor section (proximal) end to the right and with the location of its major sections labeled.
Figure 5:
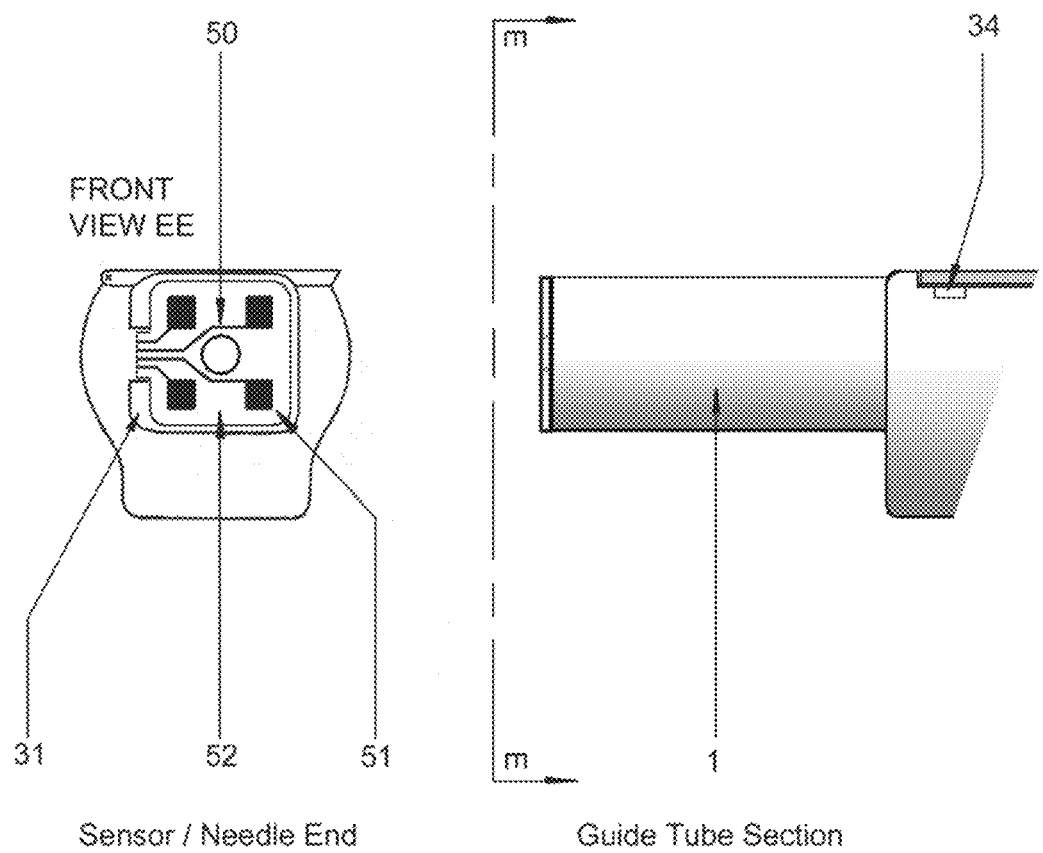
FIG. 5 is an end view of the 'syringe guide embodiment' looking toward the needle from the front (looking proximal) with a portion of the AA section shown for reference. It is pictured with the Skin Sensor Printed Circuit 52 in place on top of the Skin Sensor Support 31.

In FIG. 1 and FIG. 4 can be seen the latch protrusions 37 and the thumb buttons 39. Although in FIG. 1, they are above the plane of the section, they are shown anyway with note so the examiner can see their relative placement in relation to the internals of the housing. In FIG. 4, their actual placement in a front view is shown and in FIG. 10 they can be seen from the top in relation to the access covers. These latches hold the housing in a straight linear shape when the folding hinge 49 is straightened all the way. In FIG. 1, it can be seen that the latches must be on the outside of the housing or molded into the actual housing because if they were on the inside of the housing or protruded into the housing's smooth interior wall, they would interfere with or block the travel of the moving carriage 9. Thus, the latches are located on the outside wall of the housing. The latches consist of a piece of flat spring steel with a thumb button 39 on one end. The other end of the spring steel has barbs such that, when they are inserted into the latch protrusion 37, they cannot be removed. The shape of the spring steel is such that the thumb button 39 pops through a hole in the mating latch protrusion 37. When the folding hinge 49 is straightened, the proximal face of the guide tube/syringe guide housing 56 is brought to meet the distal face of the moving carriage and electronics housing 57, and the thumb buttons 39 mounted to the spring steel slides into the latch protrusion 37 and springs into the holes in the mating latch protrusions. The buttons pop into the holes and thus, latch the two portions of the injector housing together in a straight line. To fold the injector back in two, the thumb buttons 39 are pressed into the latch protrusions 37 so that they can exit the holes at the same time, the injector housing is folded in half.

FIGS. 1,3,7 and 8 show the initiate button 6 on the right side of the injector housing. Notice, there are thumb or finger indentations 35 (also see FIG. 4) on both the left and right sides of the housing. The injector could also be made with the initiate button 6 on the left side or it could be located on both sides with either button able to initiate an injection. This is a matter of ergonomics and the adaptability to users who are right or left handed. Note, the initiate button 6 in the location illustrated could be activated by the fore finger, little finger or thumb of either hand, yet, the feeling of the injector in the hand due to the shape of the housing may indicate that flexibility in positioning the button or buttons may be desired. The initiate button 6 presses on the snap dome 53 (see FIG. 11) which changes conformation from convex to concave and as it does so, it completes the circuit provided by the snap dome sensor 82.

Figure 8:
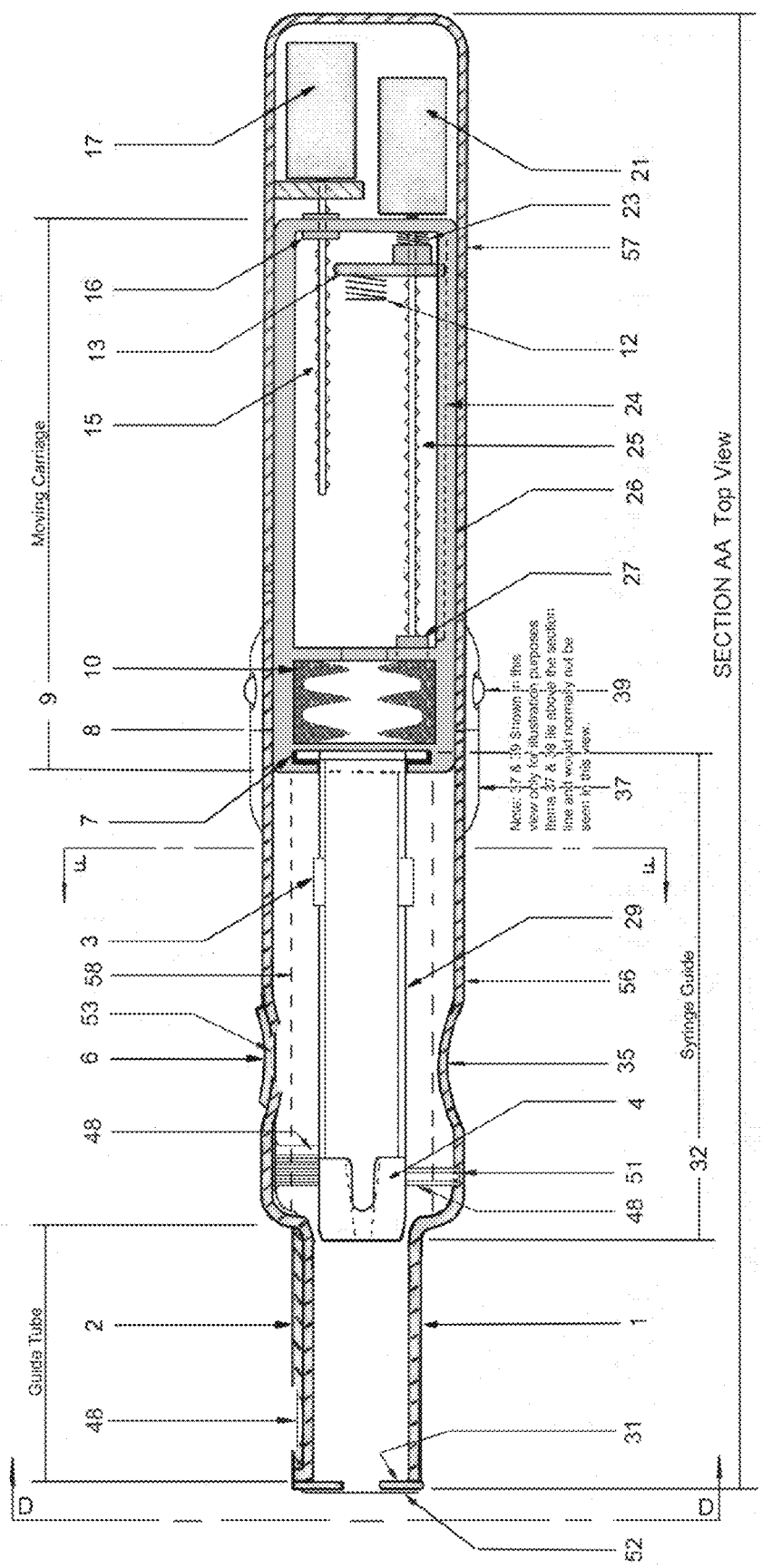
FIG. 8 is the same sectional view as FIG. 1 except the syringe including its attached needle has been removed from the view in order to clearly delineate the interior parts that are not syringe or needle parts. The syringe is not supplied as part of the invention.

FIG. 1 shows the injector housing with two different 1 ml Tuberculin syringes that have two different lengths to illustrate how the elastomeric flange grip 10 accommodates different length of syringes. FIG. 8 shows the injector housing without the syringes for reference. When the moving carriage 9 moves forward (distal), the syringe guide 32 is pushed forward so that its distal end is moved down the guide tube 1 and the needle 5 exits the housing through the distal face. The moving carriage 9 is moved forward and rearward by the carriage motor 17 which is stationary and fixed in the proximal end of the housing. The shaft of the carriage motor 17 is attached to the carriage lead screw 15, preferably by laser weld. On the carriage lead screw 15 rides a carriage lead screw nut 16 which is mounted in the proximal end wall of the moving carriage 9. It is so mounted so that it cannot rotate or move from the wall of the carriage. Therefore, when the carriage motor 17 rotates, the carriage lead screw 15 rotates, and the carriage lead screw nut 16 is forced to travel forward and rearward on the carriage lead screw 15 and since the moving carriage 9 is fixed to the nut, the moving carriage 9 is forced to slide forward and rearward inside the housing. The carriage motor 17 always rotates an amount sufficient to extend a needle 5 of one and one-half inches so that its entire exposed length is outside the housing. If a shorter needle 5 is mounted to the syringe 30, the carriage motor 17 still rotates the same amount as if the needle 5 were one and one-half inches long. Since the distance from the proximal end of the needle 5 to the distal surface is fixed by the syringe guide 32 and the guide tube 1 length, a shorter needle is necessarily extended out the distal surface of the housing to its proximal end if the moving carriage 32 moves as if it were a needle 5 of one and one-half inches. This is of course in part because the needle centering fixture 4 so holds the distal end of the syringe/needle so that the proximal end of the needle 5 is one and one-half inches from the distal face of the housing and the needle centering fixture is fixed relative to the guide tube proximal end by the syringe guide 32 whose syringe guide flange 7 is fixed to the moving carriage 9. In other words, the syringe guide 32 is shaped such that the syringe/needle it is designed to hold, is held with the proximal end of the needle exactly one and one-half inches from the distal surface of the injector. Thus, any needle 5 length is inserted into the patient up to its proximal end because the moving carriage 9 always moves the same amount (the amount necessary to insert a one and one-half inch needle up to its proximal end. Actually, to be precise, the carriage motor 9 always moves one and one-half inches plus a little extra, the extra being a distance necessary to recess the tip of a one and one-half inch needle 5 within the inside of the guide tube 1. This recess amount would be approximately 3/32nds of an inch from the distal surface. Therefore, above where the words one and one-half inches of travel occur, the actual distance traveled would be 1 and 19/32nds inches. As shown in FIG. 1, the needle 5 is shown with its tip recessed into the housing. This recess is 3/32nds inch, and the needle is a one and one-half inch needle. Therefore, to insert this needle, or any shorter needle, fully into the patient, the moving carriage 9 must move a total of 1 16/32nds plus 3/32nds equals 1 19/32nds inches.

Other injectors in the patent record either only accommodate one needle length or they provide some mechanical means of adjusting the insertion depth of a needle. If so, a needle of variable length combined with the depth adjustment can result in confusion for the user as to the actual depth since a calculation is required to get the resulting depth. With the method of this invention, needles from one-half inches to one and one-half inches can be used and the needle will always be fully inserted without making any adjustment or calculation. Instead, you simply change the penetration depth by changing the length of the needle used. Therefore, there is never any confusion as to the depth of insertion you will get as the needle length is always printed on their package it come in. You pick the depth you need by selecting the correct needle. "Full Prescribing Information" that is provided with every drug always addresses the needle length because the instructions always encompass the administration of the drug with a standard or non-standard syringe at a minimum, without any accompanying mechanical devices such as this invention. The Full Prescribing Information may also address the use of an autoinjector, injection pen device, or custom prefilled syringe, however, if the drug is provided in a syringe fillable format such as a vial, the necessary syringe and needle is addressed. To this inventor's knowledge, no injector has been devised which inserts any needle within a certain length range by supporting and moving the proximal end of the needle a fixed distance of travel to fully extend the needle beyond the distal surface of the injection device. And further, to position the proximal end of the needle by supporting the needle/syringe with a guide that conforms to the distal end of the needle/syringe and attaches to a movable positioning device which grips the proximal end of the syringe, and said positioning device moves to position the proximal end of the needle at the distal surface of the injector. Furthermore, the needle/syringe supporting guide in conjunction with the proximal syringe gripping arrangement accommodates a range of needle/syringe lengths and diameters and shapes. Example, if the user needs to administer a one inch deep injection, with this invention, you use a one inch needle to get that depth, and the range of depth accommodated is from one and one-half inches to one-half inches or smaller. Other embodiments (not illustrated) could be scaled so that other depths could be achieved. This embodiment is not intended to limit this prospect of the claims of the invention to one and one-half inches maximum depth.

Figure 6:
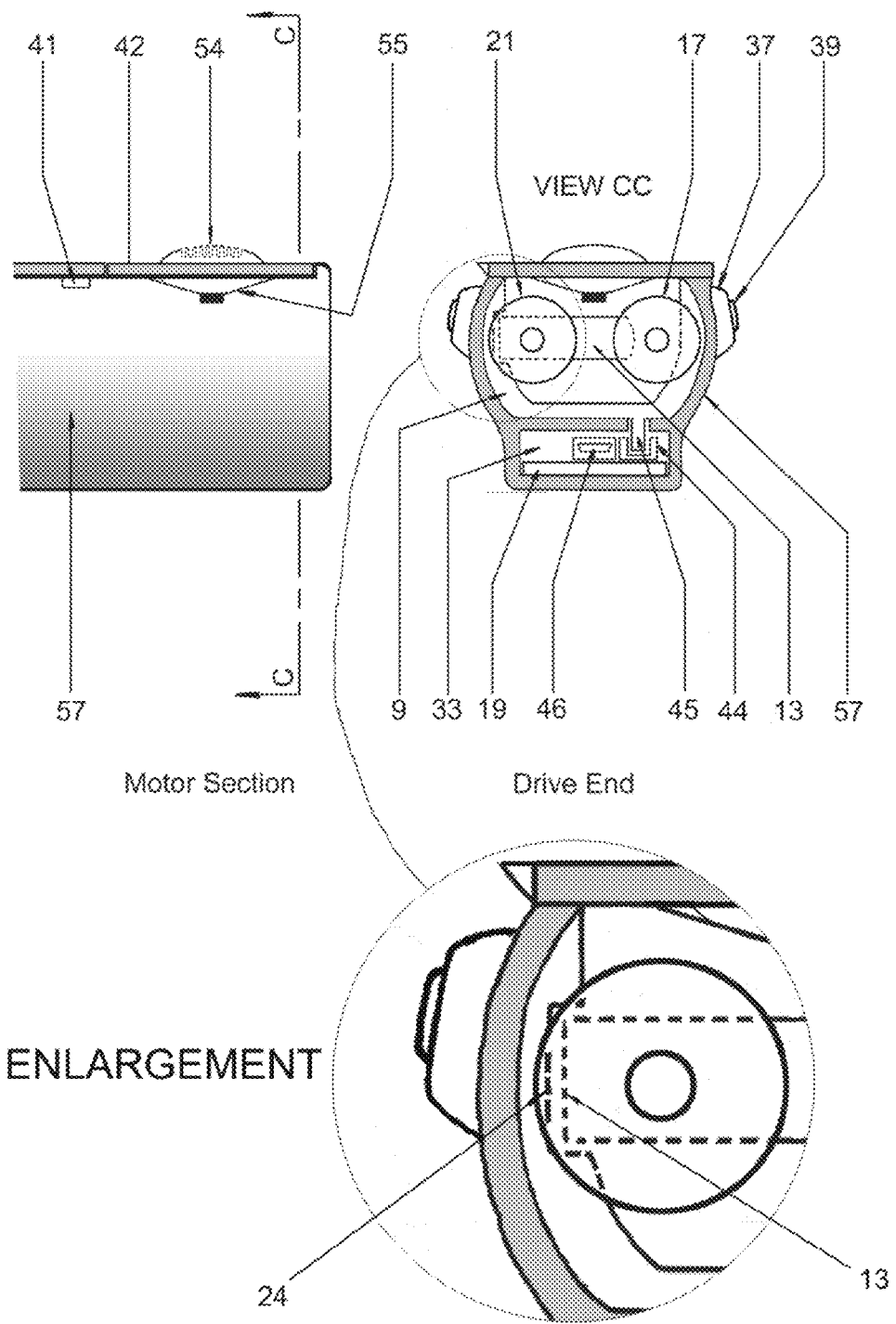
FIG. 6 is a sectional end view of the proximal (drive end) of the autoinjector. It is not specific to either of the two primary embodiments since the portion of the device to the right of the Folding Hinge 49 (the proximal end of the device) is virtually the same between both primary embodiments. The view is accompanied by a portion of the front view for reference.

This movement of 1 and 19/32nds inches is achieved by the MCU running the carriage motor 17 while monitoring the output of the carriage travel position sensor 44 (see FIG. 6, view CC). The position fin 45 which is attached to the moving carriage 9 and extends below the bottom of the moving carriage 9 and interrupts the light in the carriage travel position sensor 44 (which is mounted on the integrated circuit board 19) except at the travel limits of 1 19/32nds inch and 0 inches where the light reaches the photo sensor in the carriage travel position sensor 44 and signals the position algorithm running in the MCU which then stops the carriage motor 17. Thus, the position algorithm can insert a needle of various sizes automatically all the way into the patient and then remove the needle after the medicament has been dispensed.

Attached to the proximal outside of the moving carriage 9 and moving with the carriage forwards and rearwards, is the actuator motor 21. The shaft of the actuator motor 21 is attached to the actuator lead screw 25, preferably by laser weld. Riding on the actuator lead screw 25 is the actuator lead screw nut 26 which is attached to the actuator 13 which is prevented from rotating due to the actuator guide 24 in which the actuator 13 rides forward and rearward (see FIG. 18). Thus, when the actuator motor 21 rotates, the actuator lead screw 25 rotates, and the actuator lead screw nut is forced to travel forwards and rearwards on the actuator lead screw 25. Attached to the actuator 13 is the actuator spring 12 which presses on the plunger thumb pad 11 and forces the syringe plunger rod 14 into the barrel of the syringe 30. Note: the captive mechanism required for withdrawal of the syringe plunger rod 14 in the rearward direction as required in the aspirate analysis embodiment is not illustrated. In the pictured embodiment, the actuator 13 can push the syringe plunger rod 14 into the syringe 30, but then the plunger is left in the syringe 30 after the injection and the actuator 13 is returned to its proximal "home" position. As mentioned previously, as the actuator 13 is pushing the syringe plunger rod 14, the actuator spring 12 is partly compressed, however, when the syringe plunger seal 28 reaches the distal end of the syringe barrel it can travel no further and the syringe plunger rod 14 stops moving forward. However, the actuator motor 21 is still rotating which causes the actuator spring 12 to become further compressed. This spring force back onto the actuator 13 is reflected back through the actuator lead screw 25 to increase the torque on the actuator motor 21. Since torque is proportional to motor current and this current is being monitored by the MCU, the positioning algorithm can detect when the syringe plunger rod 14 has dispensed the entire amount of medicament and stop the motor.

FIG. 4 depicts a front view of the left side of the injector housing. The access cover, syringe section 36 and the access cover, carriage section 40 are shown at the top edge. When both access covers are in the closed position and the injector housing is straightened and the thumb buttons 39 are snapped into their holes in the latch protrusions 37, the two access covers come together and interlock at the access cover interface 38. This interface where the two access covers meet when the injector is unfolded, force the two covers to move as one. For the injector to be operational, both the access cover closed sensor, syringe section 34 and the access cover closed sensor, carriage section 41 are detected as closed and the unfolded and latched sensor 107 (see FIG. 11) detects that the housing has been unfolded and latched into place. Once the injector is locked into the unfolded position, the two covers can be flipped open as one cover, their hinges (see FIG. 3, view BB or FIG. 9, view FF) having springs (not shown) which bias the lids to either the closed or open positions. These access covers along with the internals provide for the syringe 30 to be loaded horizontally into the injector, thus providing an improvement over other patents which require the syringe to be inserted axially into the housing and then the two pieces of the housing are screwed together.

The access cover closed sensor, syringe section 34 (see FIG. 4 and FIG. 11) works by continuity of circuit. That is, a conductive spring 83 which is mounted in the access cover, syringe section 36 press on the access cover closed sensor, syringe section 34 when the lid is closed. When it so presses against the circuit, continuity is established because the spring is conductive. The completed circuit then signals to the MCU that the access cover, syringe section 36 is in the closed position. The unfolded and latched sensor 107 works by the same principle. A conductive spring 106 mounted on the distal face of the moving carriage and electronics housing 57 between the upper section and the electronics bottom compartment 33 presses on the continuity circuit that constitutes the unfolded and latched sensor 107 when the housing is unfolded and latched into place, and therefore signals the MCU that injector is in the unfolded and latched position.

Next to the access covers on the top of the proximal end of the housing is the access cover, motor section 42 (see FIG. 4) which contains the speaker grill 54 and underneath the grill, mounted to the underneath side of the access cover, motor section 42 is the speaker 55.

As illustrated in FIG. 4, mounted on the left side of the injector housing, on the outside of the moving carriage and electronics housing 57 is the operator key pad 86 which contains in the bottom row, the scroll left button 87 and the scroll right button 88 which scroll the available selection, as shown in the currently displayed menu, onto and off the operator display 85 (see FIG. 10). In the top row are the enter button 90 which accepts the currently displayed option, and the return button 89, which takes the user up one level in the displayed menu system. The menu system's current menu and option selection (as well as animation graphics and injector status) is displayed in the operator display 85 which is pictured in FIG. 10. Above and to the right of the operator display 85 is the writing surface 95 which could either be a "white board" surface or more preferably, a "pencil marking" surface which can be used to record such information as the patient name or wrist number, drug, current injector mode, etc. The "pencil marking" surface also provides for easy markable tape removal wherein, information which changes frequently can be written on a piece of markable tape affixed to the pencil marking surface and quickly removed and replaced with new information without having to erase actual pencil writing.

Referencing FIG. 6, view CC, one can see the electronics bottom compartment 33 which houses the integrated circuit board 19. On this circuit board and positioned flush to the proximal end of the moving carriage and electronics housing 57 is the micro USB port 46. This is used to connect to a personal computer or an AC charging station or an AC wall charger. FIG. 6 also provides a view of the carriage motor 17, the actuator motor 21 and the actuator 13 as it fits into the actuator guide 24. The latch protrusions 37 with the thumb buttons 39 can be seen sticking out from the upper sides of the housing.

The battery 18 and the haptic motor 129 (not pictured) are located in the battery and vibrator compartment 72 which is located in the guide tube/syringe guide housing 56 in a compartment beneath the syringe guide portion of the upper housing (see FIG. 3, view BB or FIG. 9, view FF).

Figure 12:
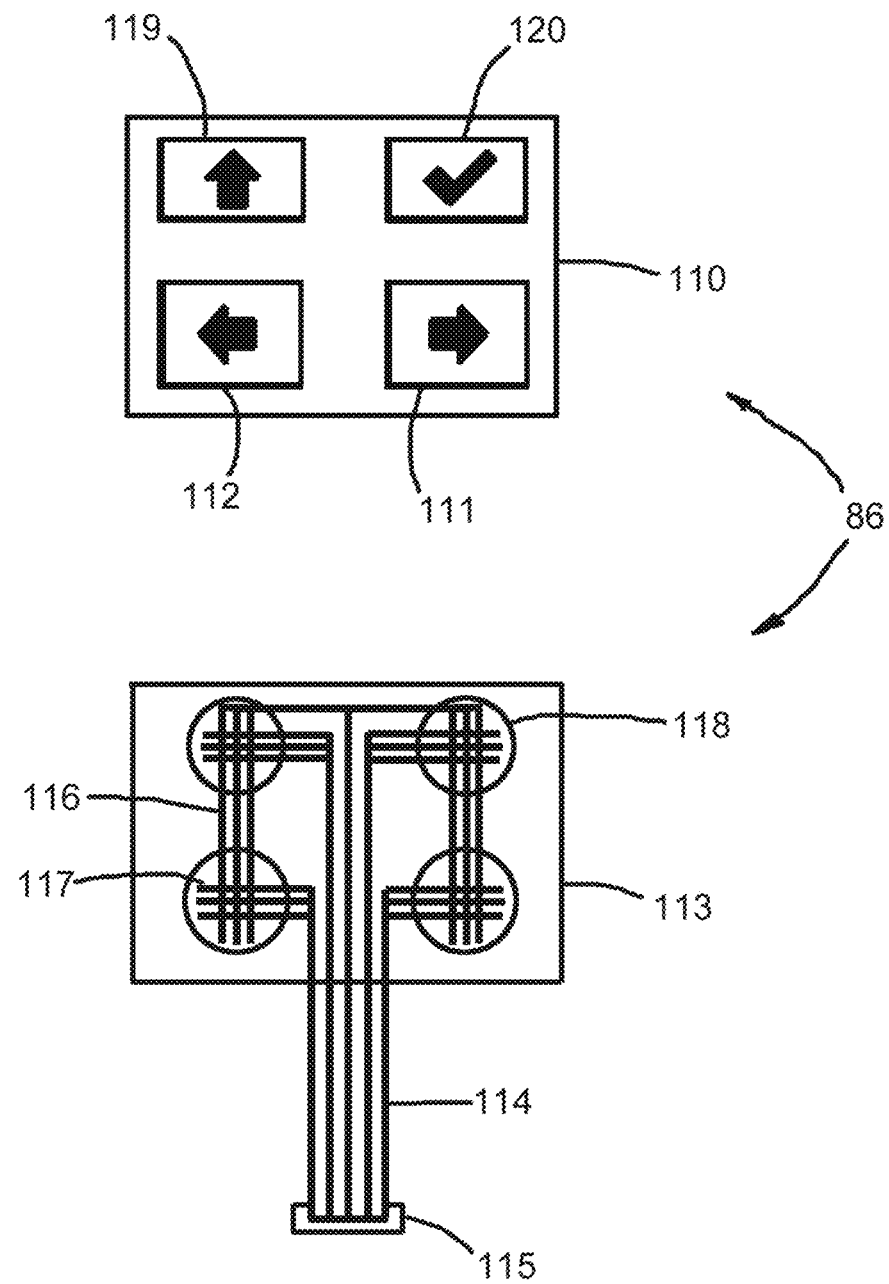
FIG. 12 is an illustration of the Operator Keypad 86 and in particular, the Membrane Keypad Overlay 110 and one possible method of arranging the lamellar contact traces under its 'Key' symbols. The Operator Keypad 86 is common to both primary embodiments of the invention.

FIG. 12 is common to both embodiments pictured in the drawings. In particular, it depicted is the operator key pad 86 which is a membrane type touch keypad. The particular design is without snap domes in order to keep it flat however, a version with snap domes to provide better tactile sense could be utilized. Pictured are the 3.3 volt traces 116 and the key traces 117. These two traces are separated from each other by a gap established by an intermediate lamella with interim substrate cutouts 118 which allow the two traces to come together and complete an electric circuit when the area above the intersection of the traces is pressed with the finger or thumb by the injector operator. The membrane keypad ribbon cable 114 is an extension of the key traces 117 which leads down and an indentation on the inside wall of the moving carriage and electronics housing 57 to reach the integrated circuit board where it is connected by a ribbon cable connector 115. The top layer of the operator keypad 86 is the membrane keypad overlay 110 which contains raised embossed symbols for four function keys. These are the return symbol 119 which when pressed signals the MCU to go up one level in the menu system as displayed on the operator display 85 (see FIG. 10). The enter symbol 120 which when pressed signals the MCU to accept the current option displayed in the lower line of text in the operator display 85. The scroll left symbol 112 causes the current option appearing in the bottom line of text in the operator display 85 to scroll off the display to the left and another option to scroll in and replace it from the right. The scroll right symbol 111 causes the current option appearing in the bottom line of text in the operator display 85 to scroll off the display to the right and another option to scroll in and replace it from the left. The options are in a loop so that if you keep scrolling to the left or right, the options will repeat.

Figure 13:
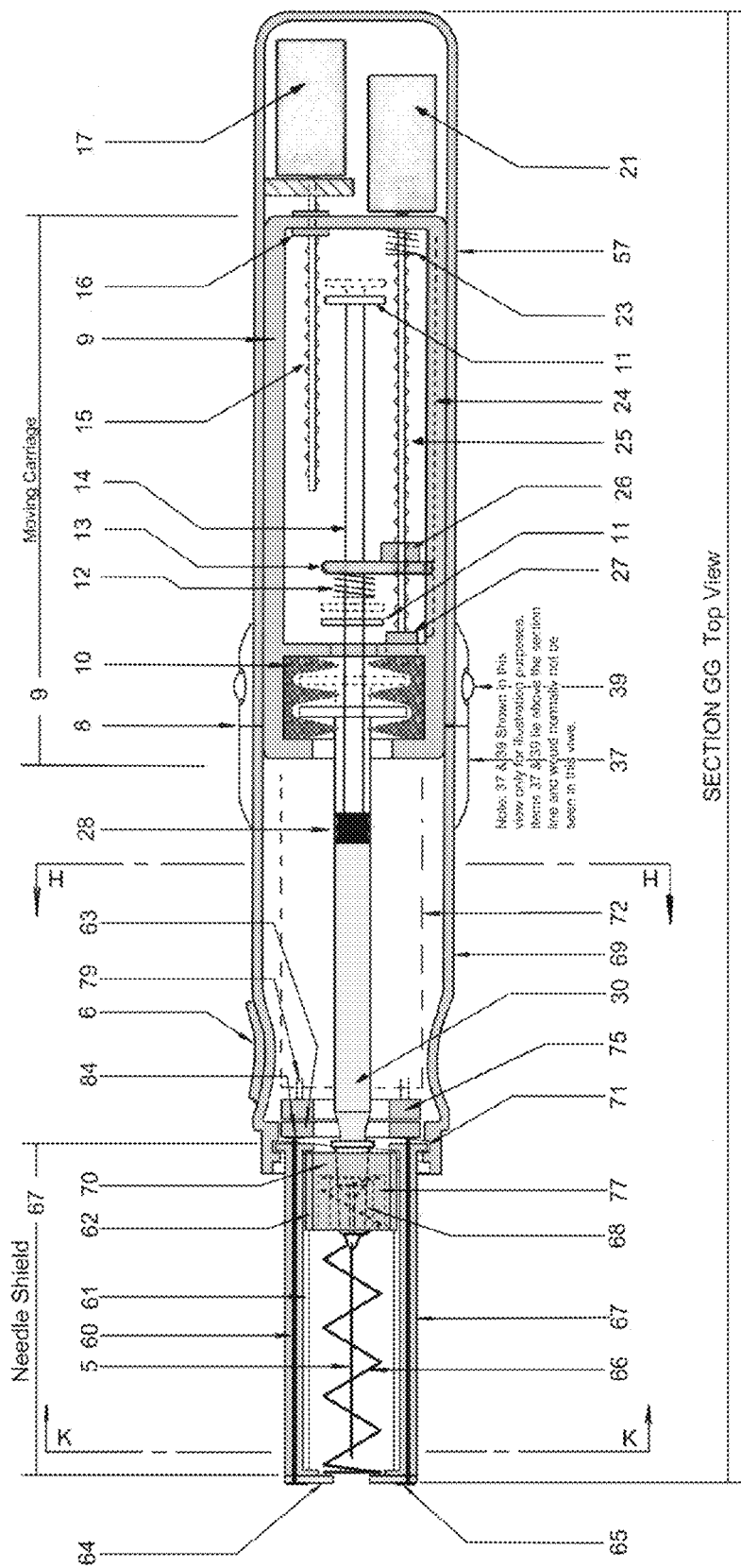
FIG. 13 is a sectional view of a 'disposable needle shield embodiment', looking down from the top with the upper partition from the section GG removed. That is, the injector is cut horizontal down the needle axis to illustrate the parts within from an overhead perspective.

FIGS. 13 through 22 exclusively depict the 'disposable needle shield embodiment' of the invention. FIG. 13 is a sectional view of the 'disposable needle shield embodiment looking down from the top. The needle shield 67 is a separate piece from the overall housing to which it attaches and detaches. It is cylindrical in shape. The skin sensor contact support 64 is part of the needle shield 67 or preferable, is a separate piece consisting of a printed circuit board which snaps onto the distal face of the needle shield 67. If it is a printed circuit board, it will contain the skin sensor contacts 65 of the skin sensor circuitry. Most preferably, it is at least a separate piece that attaches to the needle shield 67 and supports the skin sensor contacts 65 as part of traces on the printed circuit board. As a separate piece that snaps onto the needle shield 67, it allows the needle guide 70 to be loaded inside the needle shield 67 first before being attached. This is important because the needle guide 70 is captive inside the needle shield 67. With this embodiment, the flexible electric circuit 76 (see FIG. 22) does not connect directly with the skin sensor contacts 65. Instead, the flexible circuit 76 terminates at the flexible circuit connector 104 which is located on the pressure contact circuit board 63 (see FIGS. 19, 20, and 22). The pressure contact circuit board 63 makes contact with the skin sensor contacts 65 via molded in conductors 60 which are embedded into the plastic wall of the needle shield 67. Specifically, the skin sensor contacts 65 are connected to the molded-in conductors 60 which travel the length of the needle shield 67 and make contact with electrically conductive pressure contacts located on the pressure contact circuit board 63 which provides electrical traces to the flexible circuit connector 104 which attaches to the flexible electric circuit 76 which eventually connects with the integrated circuit board 19. FIG. 14, view KK provides a section through the needle shield 67 which shows the molded-in conductors 60. This arrangement provides for the detachment of a used needle shield 67 and the replacement of a new needle shield 67 with automatic connection of the skin sensor contacts 65 to the flexible electric circuit 76 as the new needle shield 67 is attached. This is important because the needle shields 67 are disposable and when a new one is attached, no operator intervention is required to establish electrical communications between the MCU and the skin sensor contacts 65. More specifically, the molded-in conductors 60 protrude from the proximal end of the needle shield 67 and are bent into a U shape or are capped with a rounded conductive ends that make a pressure contact with the conductive pressure contacts 84 that are located on the pressure contact circuit board 63. The ends of the molded-in conductors 60 which protrude from the proximal surface of the needle shield 67 are bent into a U shape or capped with rounded ends because they are pressed into the pressure contact circuit board 63 by a wiping action as the needle shield 67 is attached by a twisting motion.

Figure 22:
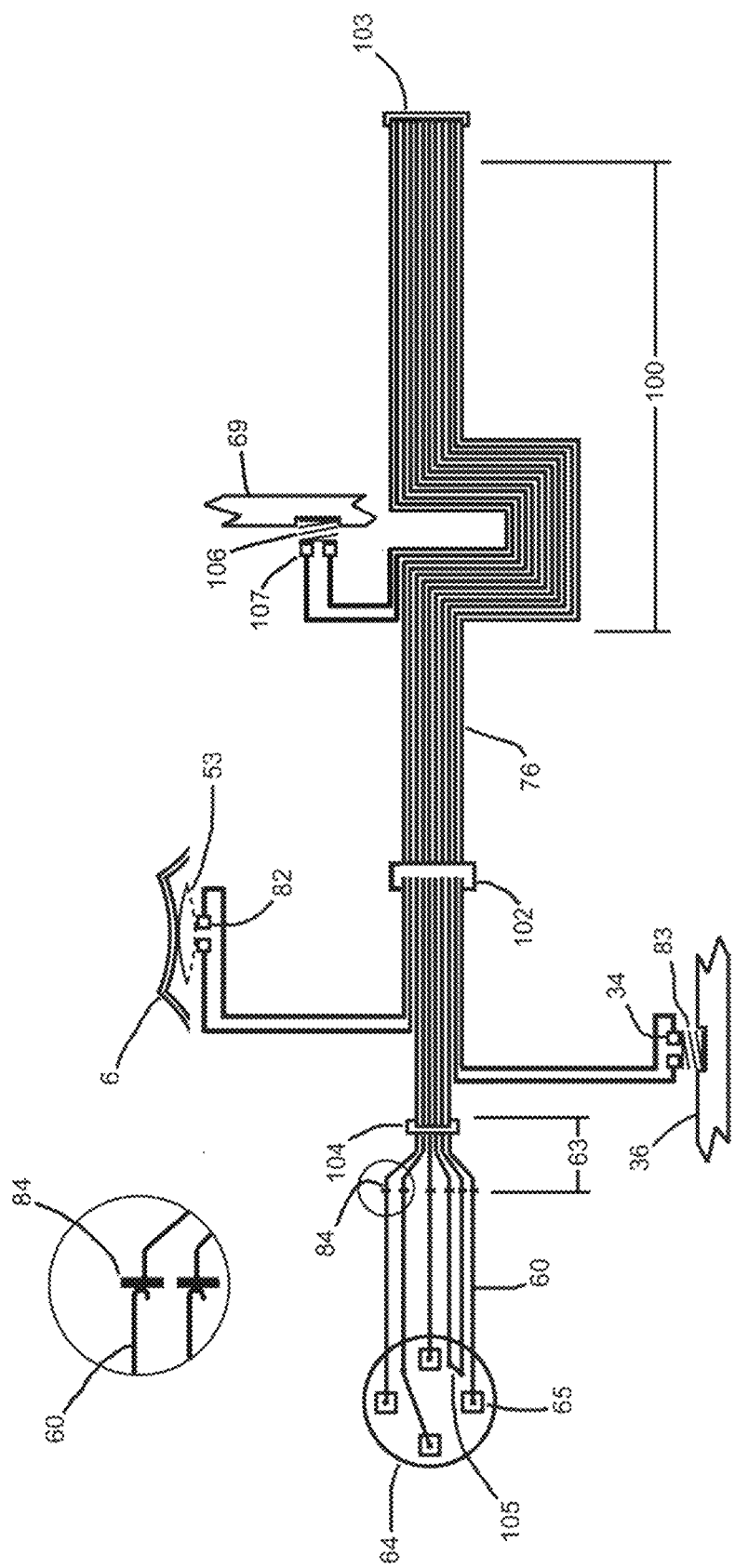
FIG. 22 is an illustration of the Flexible Electric Circuit 76 that is part of the 'disposable needle shield embodiment'. Pictured at the extreme distal end, are the Skin Sensor Contact Support 64 and the Skin Sensor Contacts 65. These are not part of the Flexible Electric Circuit 76 which however, interfaces to 64 and 65 by way of the Molded-In Conductors 60 which connect to the Pressure Contact Circuit Board 63 which makes electrical contact with the Flexible Electric Circuit by way of the Flexible Circuit Connector 104. The Flexible Electric Circuit 76 also incorporates the discrete digital inputs from the Access Cover, Syringe Section 36, the Initiate Button 6, and the Unfolded and Latched Sensor 107.

In FIG. 22 one can notice that there are two extra molded-in conductors 60 than the four that are required for the four skin sensor contacts 65. These two extra molded-in conductors 60 are connected together by a molded-in conductor bridge 105 on the skin sensor contact support 64. These two extra molded-in conductors 60 follow the same path back to the MCU as the other molded-in conductors 60 and since they are connected together at the molded-in conductor bridge 105, they naturally complete a circuit back to the MCU when the needle shield 67 is connected. This is done so that the MCU can detect that the needle shield 67 has been connected to the injector housing by monitoring the conductivity between these two electrical paths and not allow certain operations if it doesn't detect that the needle shield 67 is attached.

Figure 19:
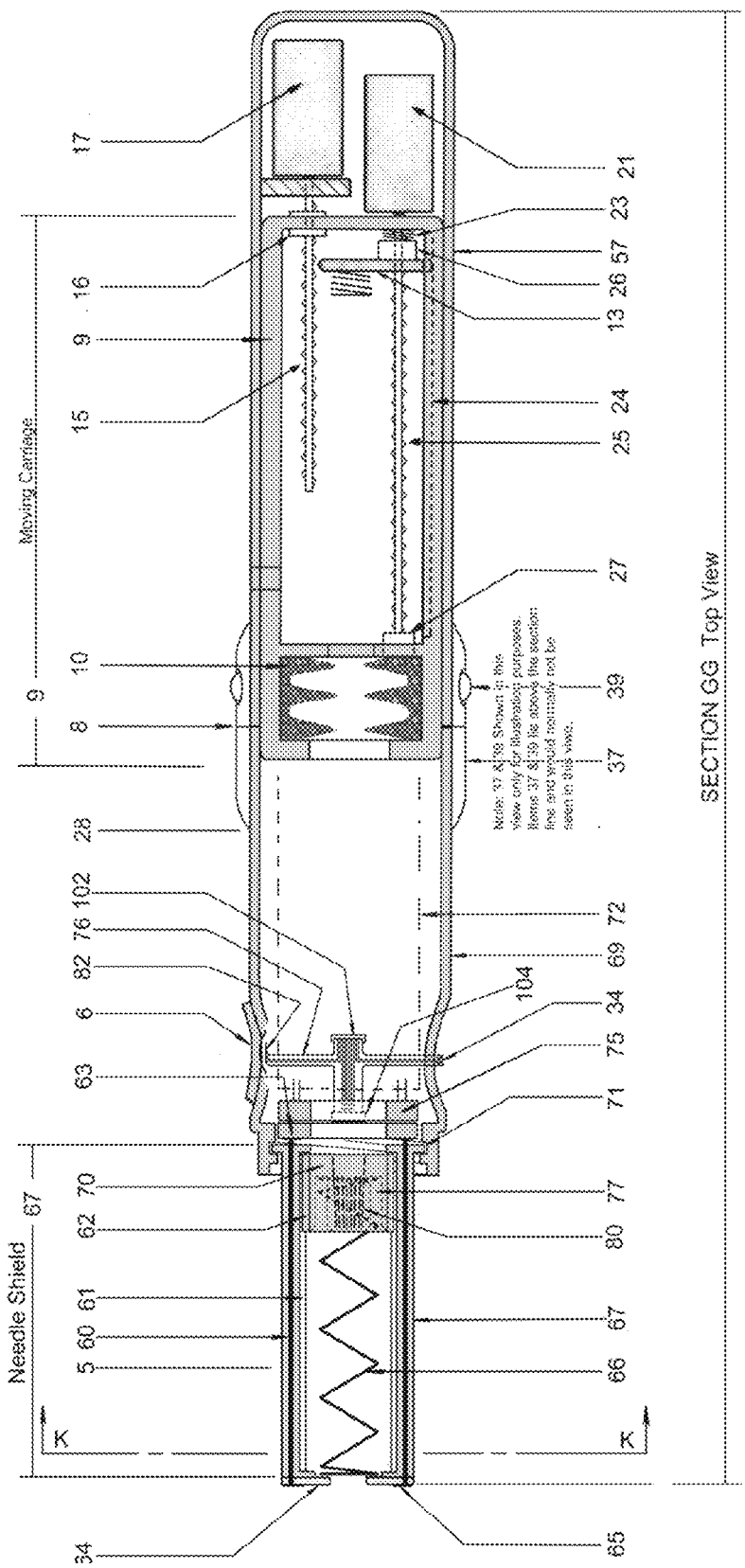
FIG. 19 is the same sectional view as FIG. 13 except the syringe including its attached needle has been removed from the view in order to clearly delineate the interior parts that are not syringe or needle parts. The syringe is not supplied as part of the invention.
Figure 20:
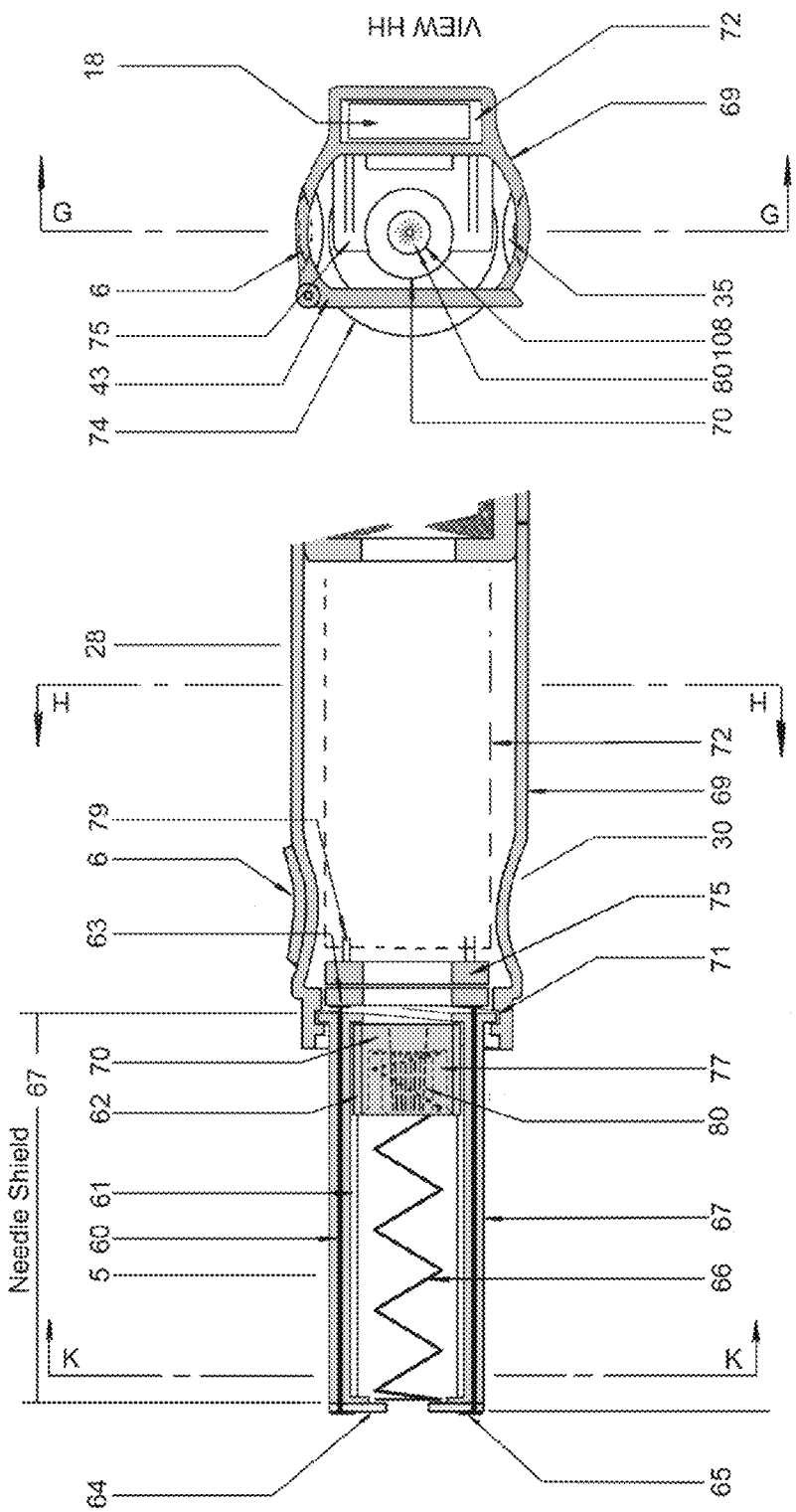
FIG. 20 is a sectional view through the Syringe Section Housing 69 of the 'disposable needle shield embodiment' without the syringe pictured. This view aids in depicting the distal end where the syringe needle (attached to the syringe) is inserted since the syringe is removed from the view. A portion of the top sectional view GG is included for reference.

Although the flexible electric circuit 76 is not pictured in FIG. 13, 14, or 15, it is pictured in FIG. 19 and FIG. 20 where it is shown making contact with the pressure contact circuit board 63 via the flexible circuit connector 104 and also providing the access cover closed sensor, syringe section 34 and also laying flat against the inside wall to reach the tactile initiate switch 53 which consists of the snap dome sensor 82 before entering the lower battery and vibrator compartment 72 through the slot 102 (see FIG. 22).

Referring to FIG. 22, the flexible electric circuit 76 is shown in shape but not to scale. The circuit is die cut from a solid piece of plastic that has been printed with electrical conductors (traces) and the arms of the circuit are so shaped that they can reach each of the sensors that it provides. The flexible circuit serpentine 100 is shaped so that it can coil through the folding hinge 49 to reach the integrated circuit board 19 where it is attached by the flexible circuit connector 103. The flexible electric circuit 76 enters the battery and vibrator compartment 72 through a slit 102 between the upper and lower compartments of the syringe section housing 69 so that it can serpentine through the folding hinge 49 and terminate onto the integrated circuit board 19 which resides in the electronics bottom compartment 33 of the moving carriage and electronics housing 57.

The 'disposable needle shield" embodiment is made especially for removable needle syringes, and in particular, Luer slip and Luer lock type needles and syringes, although other removable needle types could be accommodated by the design. Referring to FIG. 14, one can see the needle shield 67 which consists of a tube. Inside the tube is the needle guide 70. This needle guide 70 is biased toward the proximal end of the needle shield 67 by a needle guide spring 66 which keeps the needle guide at the proximal end of the tube unless a distal pressure is applied to the needle guide 70. Within the needle guide 70 is a spring recess 77 which provides for the needle guide spring 66 to compress when the needle guide 70 is pushed toward the distal end of the needle shield 67. This is important so that the needle guide can travel all the way to the inside surface of the skin sensor contact support 64. This allows the entire length of the needle 5 to protrude from the distal face of the needle guide 70, and exit the injector housing and enter the patient's tissue. The needle guide 70 has two fins at 3 and 9 o'clock which ride in needle shield grooves 61 within the inside wall of the needle shield 67. The groves permit the needle guide 70 to move forwards and rearwards but not to rotate. Therefore, if the needle shield 67 is rotated, the needle guide 70 is necessarily rotated. Likewise, the luer slip/luer lock needle 68 has a connector with four fins on it which mate with vein indentations 80 which are groves on the inside of the needle guide 70. Thus, if the needle guide 70 were rotated, the luer slip/luer lock needle 68 would be forced to rotate as well. It is rotation that is used to remove a luer type needle from a luer type syringe. Thus, if the needle shield 67 were rotated, it will rotate the needle guide 70 and thus rotate the luer slip/luer lock needle 68 thus removing it from the syringe. The needle guide 70 is internally shaped like the needle guard that comes with the needle to protect it and which stays onto the needle by a friction fit. This same friction fit is molded into the interior shape of the needle guide 70 so that, when the needle is removed from the syringe by the twisting action, it is friction fit within the needle guide 70 and remains with it, thus allowing the needle to be removed safely from the syringe and disposed along with the needle shield 67. Thus in a sense, the needle shield 67 has replaced the needle guard which is supplied with the luer type needle in as far as the needle guard protects against accidental needle stick. However, unlike using a conventional luer syringe/needle without the advent of this invention, the user does not have to re-cap or re-cover the exposed needle after injection which is the most dangerous time for needle stick is since it has already been exposed to bodily tissues and possible pathogens of the patient. With this invention, the user merely twists the needle shield 67 to remove the needle from the syringe, and then disposes of it in a biohazard container.

The injector housing attaches to the needle shield 67 much the same way that a luer lock syringe attaches to a luer needle. All luer needles have an oval flange at the proximal end of their connector. This oval flange engages internal threads at the distal face of a luer lock syringe. Then, a twist causes the threads to pull the needle's oval flange into the syringe and hold it firmly. The same arrangement has been designed into the front of the injector housing which contains luer-like threads 71 and the proximal surface of the needle shield 67 which consists of an oval flange. Thus, when the oval flange of the needle shield 67 is inserted into the luer like threads 71 at the front of the injector and twisted, the needle shield 67 is drawn into the injector housing luer like threads 71 where the projecting bent ends of the molded-in conductors 60 are pressed into the conductive pressure contacts 84 of the pressure contact circuit board 63, and thus, the MCU by way of the flexible electric circuit 76 comes into electrical communication with the skin sensor contacts 65.

Since an oval flange of the needle shield 67 has 180° symmetry, the flange could be inserted into the luer-like threads 71 in two different orientations. However; it is necessary that the molded-in conductors 60 line up with the conductive pressure contacts 84. Therefore, only one orientation of insertion can be allowed. This is accomplished by placing an alignment tab 73 onto the inside rim of the luer-like thread 71 and a mating notch 78 into the oval flange of the needle shield 67. Thus, the needle shield 67 can only be inserted into the luer-like thread 71 in one orientation and the molded-in conductors 60 will necessarily line-up with the conductive pressure contacts 84 when the needle shield 67 is twisted snug.

To this inventor's knowledge, no patent or device exists until this invention that provides a needle shield designed for Luer type needles which prevents needle stick by twisting the needle off of the syringe after injection and contains a needle guide within which friction grips the Luer needle 68 and guides the needle during automatic needle insertion with automatic injection devices.

The needle guide 70 holds the removable needle connector 20 and the syringe 30 to which it is attached at the center line of the needle shield 67 so that the needle 5 is guided straight out the center of the distal end of the injector housing. As mentioned, the needle guide 70 is so molded that the needle connector 20 of a luer type removable needle, fits snugly with a friction fit within its interior shape. Said another way, the needle guide 70 is molded of plastic with an interior shape which is made to friction grip luer type needles 68 in the same way that a luer needle cover friction grips a luer needle connector 20. This arrangement can accommodate a wide range of syringe diameters since luer needle connectors 20 are of one standard size but the syringe barrel can vary and use the same luer connector. In between the needle guide 70 and the elastomeric flange grip 10 there is only open space. With this embodiment, there is no syringe guide and one isn't needed. When the moving carriage 9 moves forward, the elastomeric flange grip 10 pushes the syringe and therefore, the needle into the patient as the needle guide 70 moves forward against the needle guide spring 66. When the moving carriage 9 moves rearward to withdraw the needle, the elastomeric flange grip 10 pulls rearward on the syringe finger flange thus pulling the syringe 30 with it and the attached needle is withdrawn from the patient's tissue due to the friction grip between the luer slip type needle connector 20 and the syringe and also due to the needle guide spring 66 pushing back on the needle guide 70, which pushes back on the needle connector 20 thus helping to keep the needle with the syringe. The friction between the luer type needle 68 and the needle guide 70 is only require to keep the needle connected to the syringe in the case of Luer slip connections. In the case of Luer lock connections, the needle connector 20 is locked into the syringe and must follow the syringe rearward when the moving carriage 9 is moved rearward.

To insert a Luer type syringe/needle combination into the injector, the user simply inserts the end of the luer needle 5 into the needle guide 70 and pushes the syringe finger flange 92 into the elastomeric flange grip 10. If a different elastomeric flange grip 10 is needed for the particular syringe, it can be replaced. The elastomeric flange grip 10 rests within a rectangular cavity within the moving carriage 9. To change it out, simply remove it by pulling it out of its and replace it with the appropriate one by pushing it into the cavity in the moving carriage 9. The elastomeric flange grips may be color coded to facilitate selecting the correct one for the brand and model of the luer type syringe chosen.

Referring to FIG. 15*a*, view HH, a section provides a distal view looking at the syringe 30 and the needle guide 70 from a sectional plane through the syringe section housing 69. The center black circle is the syringe plunger seal 28 and the circle around it is the needle connector 20. The next circle outward represents the needle guide 70. In this view, one can easily see the proximal side of the pressure contact circuit board support 75. The arc drawn over the access cover represents the exterior of the luer-like thread 74 which is part of the housing which accepts the needle shield 67 from the other side. Referring to FIG. 20, view HH, a sectional view provides a look at the needle guide 70 but without a syringe in place. The central item shown is the interior of the needle guide 70 depicting the vein indentations 80 (groves) as radial lines which engage the fins on a Luer type needle 68 (see FIG. 15*a*). A Luer type needle 68 has four fins, however, the inside of the needle guide 70 has many groves or vein indentations 80 so that the Luer needle connector's fins align up with a set of four groves no matter at what angle the Luer type needle 68 is inserted into the needle guide 70 (slip type Luer needle connectors 20 slip onto a Luer slip type syringe at any angle. Therefore, the plurality of groves accommodates the four fins of the luer needle connector 20 no matter what angle the four fins take in space.) Note in the sectional top view of FIG. 20, that the groves (vein indentations 80) on the interior of the needle guide 70 can be seen.

Referring to FIG. 15*b*, the elastomeric flange grip 10 is the part which accommodates the length of the syringe by providing a gripping action on the syringe finger flange 92. As shown by view JJ elastomer & syringe, the elastomeric flange grip 10 also provides a grip of the syringe cylinder. This keeps the proximal end of the syringe stationary and centered in the x and y dimensions, with the z dimension being the longitudinal axis of the injector or essentially, the needle 5 axis. The proximal end of the syringe 30 is held from moving in the z dimension (forward or rearward) by the fins of the elastomeric flange grip 10. The fins in these figures show their location to accommodate BD and Terumo Luer slip 1 ml plastic Tuberculin syringes; however, different elastomeric flange grips 10 with different fin locations and shapes could be designed to accommodate syringes who have their finger flanges 92 in different locations. It is easy to see that by moving the fins a small amount and/or by varying their x and y cylinder gripping dimensions, and being that they are elastomeric which flexes to different shapes, that a few versions of elastomeric flange grips 10 could accommodate a large variety of standard removable needle syringes 30 of various lengths and diameters. To this inventor's knowledge, this arrangement where the distal end of the syringe/needle combination is held by a needle guide 70 which is spring biased toward the syringe (biased rearward) and the syringe finger flange is held by an elastomeric gripper which pushes the syringe into the patient and pulls the syringe out of the patient, has never been done or patented. Additionally, to this inventor's knowledge, no finger flange grip has been devised which grips the proximal end of the syringe by an arrangement of fins which hold the finger flange in the z dimension which also grip the barrel of the syringe in the x and y dimensions.

Figure 16:
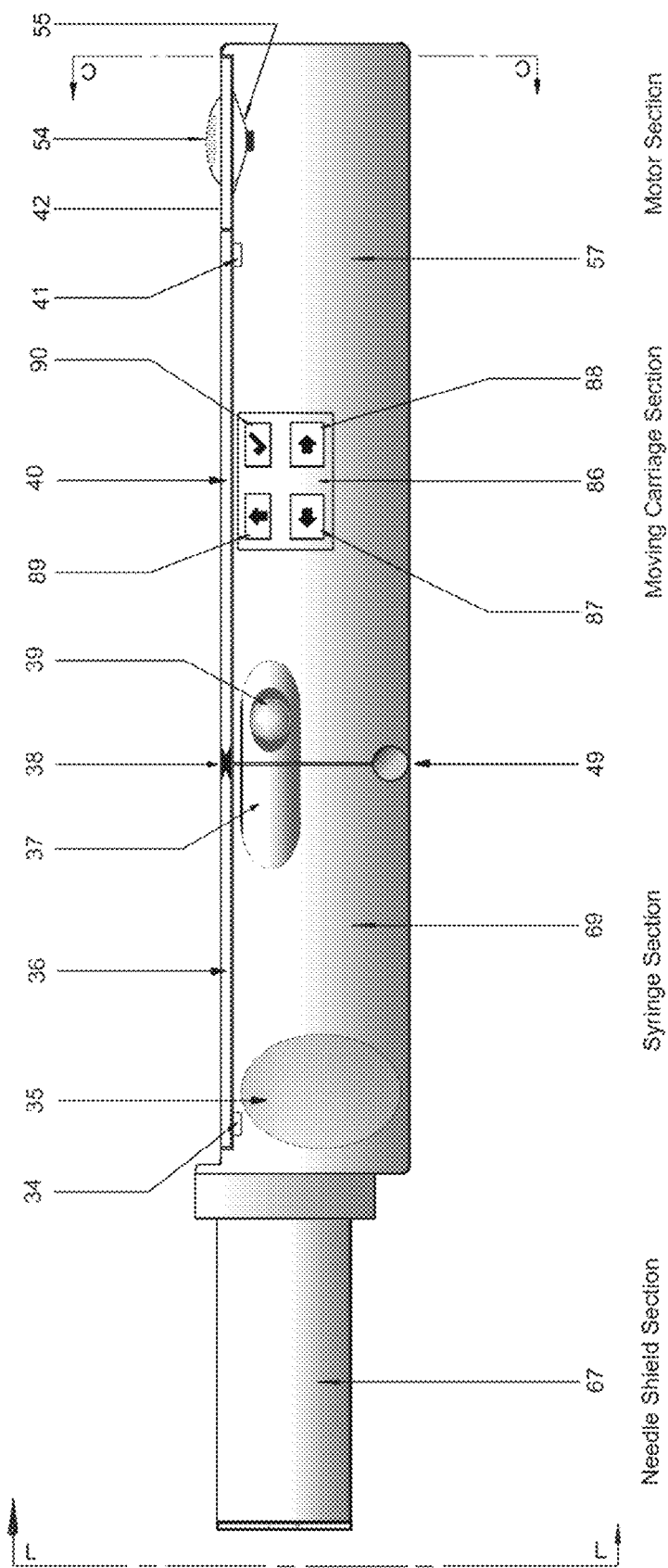
FIG. 16 is a side view of the 'disposable needle shield embodiment' with the needle shield section (distal) end to the left, and the motor section (proximal) end to the right and with the location of its major sections labeled.
Figure 17:
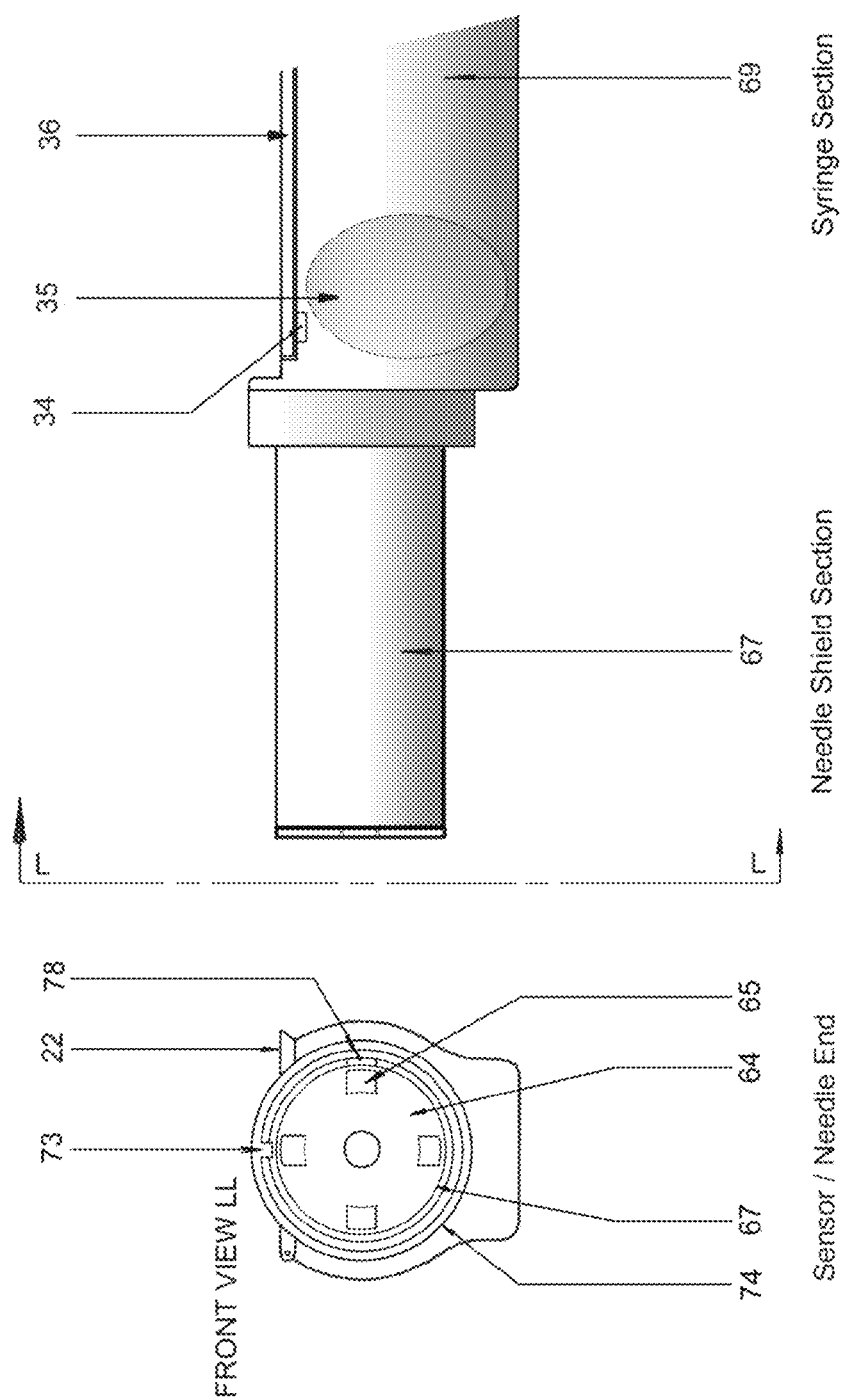
FIG. 17 is an end view of the 'disposable needle shield embodiment' looking toward the needle from the front (looking proximal) with a portion of the GG section shown for reference. The Skin Sensor Contact Support 64 and the Skin Sensor Contacts 65 are pictured.
Figure 21:
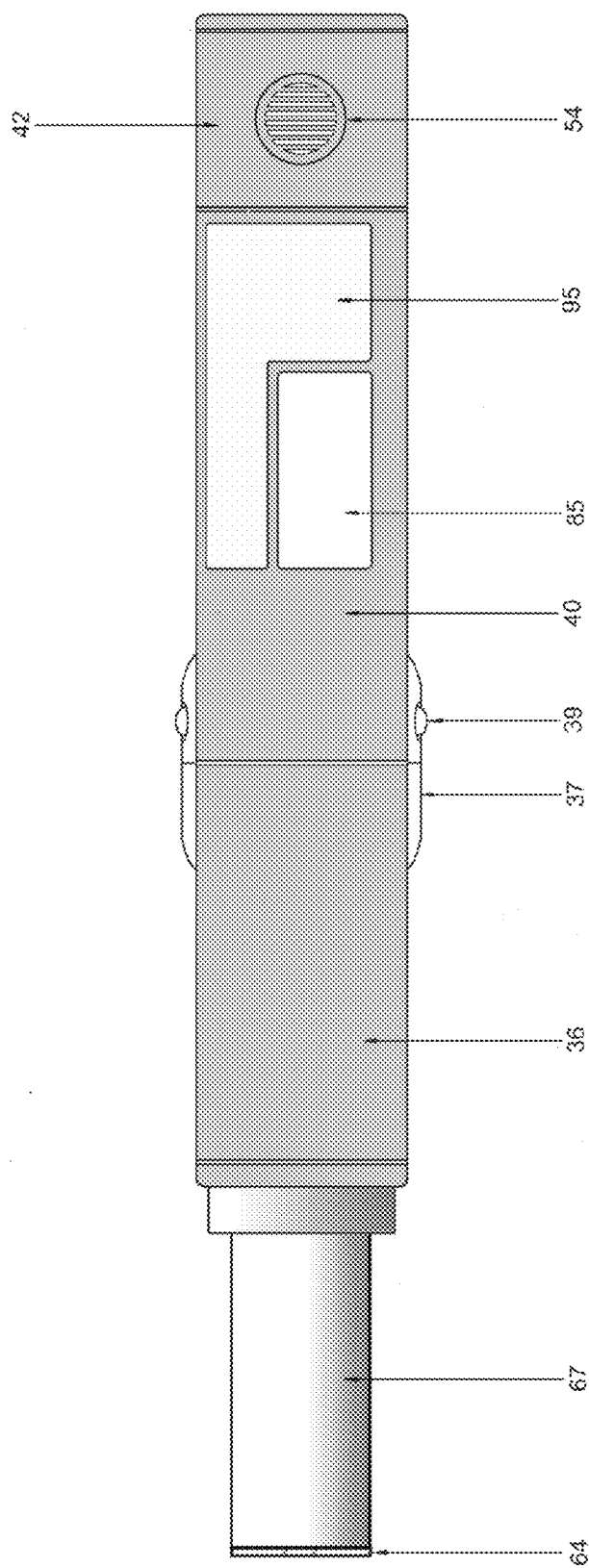
FIG. 21 is a non-sectional top view of the 'disposable needle shield embodiment' of the invention with the distal (needle) end on the left and the proximal (motor section) end on the right, which depicts the Access Covers 36 and 40 along with the Operator Display 85 and Speaker Grill 54 locations.

In FIG. 13, FIG. 16 and FIG. 21 can be seen the latch protrusions 37 and the thumb buttons 39. Although in FIG. 13, they are above the plane of the section, they are shown anyway with note so the examiner can see their relative placement in relation to the internals of the housing. In FIG. 16, their actual placement in a front view is shown and in FIG. 21, they can be seen from the top in relation to the access covers. These latches hold the housing in a straight linear shape when the folding hinge 49 is straightened all the way. In FIG. 13, it can be seen that the latches must be on the outside of the housing or molded into the actual housing because if they were on the inside of the housing, they would interfere with the travel of the moving carriage 9. The latches consist of a piece of flat spring steel with a thumb button 39 on one end. The other end of the spring steel has barbs such that, when they are inserted into the plastic latch protrusion 37, they cannot be removed. The shape of the spring steel is such that the thumb button 39 pops through a hole in the mating latch protrusion 37. When the folding hinge 49 is straightened, the proximal face of the syringe section housing 69 is brought to meet the distal face of the moving carriage and electronics housing 57, and the thumb buttons 39 mounted to the spring steel slide into the mating latch protrusion 37 with the button holes. The buttons pop into the holes and thus, latch the two portions of the injector housing together in a straight line. To fold the injector back in two, the thumb buttons 39 are pressed into the latch protrusions 37 so that the buttons can exit the holes while at the same time, the injector housing is folded in half.

FIGS. 13, 14, 15*a*, 15*b*, 19, and 20 show the initiate button 6 on the right side of the injector housing. Notice, there are thumb or finger indentations 35 (see FIG. 16) on both the left and right sides of the housing. The injector could also be made with the initiate button 6 on the left side or it could be located on both sides and either button could be able to initiate an injection. This is a matter of ergonomics and the adaptability to users who are right or left handed. Note, the initiate button 6 in the location illustrated could be activated by the fore finger, little finger or thumb of either hand, yet, the feeling of the injector in the hand due to the shape of the housing may indicate that flexibility in positioning the button or buttons may be desired. The initiate button 6 presses on the snap dome 53 (see FIG. 22) which changes conformation from convex to concave and as it does, it completes the electric circuit provided by the snap dome sensor 82.

FIG. 13 shows the injector housing with two different 1 ml Luer type Tuberculin syringes that have two different lengths to illustrate how the elastomeric flange grip 10 accommodates different lengths of syringes. FIG. 19 shows the injector housing without the syringes for reference. When the moving carriage 9 moves forward (distal), the syringe is pushed forward by the elastomeric flange grip 10 so that the distal end of the syringe, which is connected to the Luer needle 68 which is inserted into the needle guide 70, is moved down the tube of the needle shield 67 and the needle 5 exits the housing through the distal face of the housing. The moving carriage 9 is moved forward and rearward by the carriage motor 17 which is stationary in the proximal end of the housing. The shaft of the carriage motor 17 is attached to the carriage lead screw 15, preferably by laser weld. On the carriage lead screw 15 rides a carriage lead screw nut 16 which is mounted in the proximal end wall of the moving carriage 9. The carriage lead screw nut 16 is so mounted so that it cannot rotate or move axially or move in relation to the moving carriage 9. Therefore, when the carriage motor 17 rotates, the carriage lead screw 15 rotates, and the carriage lead screw nut 16 is forced to travel forward and rearward on the carriage lead screw 15 and since the moving carriage 9 is affixed to the nut, the moving carriage 9 is forced to slide forward and rearward inside the housing. The carriage motor 17 always rotates an amount sufficient to extend a needle 5 of one and one-half inches so that its entire exposed length is outside the housing. If a shorter needle 5 is mounted to the syringe 30, the carriage motor 17 still rotates the same amount as if the needle 5 were one and one-half inches long. Since the distance from the proximal end of the needle 5 to the distal surface is fixed by the length of the needle shield 67, a shorter needle is necessarily extended out the distal surface of the housing to its proximal end if the moving carriage 32 moves as if it were a needle 5 of one and one-half inches. This is of course in part because the needle guide 70 so holds the needle connector 20 so that the proximal end of the needle 5 is one and one-half inches from the distal face of the housing no matter what the needle length and the moving carriage 9 always moves as if it were a one and one-half needle attached to the syringe. In other words, the needle shield 67/needle guide 70 are sized such that the proximal end of the needle 5 is one and one-half inches from the distal surface of the housing. Thus, a one and one-half inch movement of the needle guide will always insert any needle into the patient up to its proximal end because the moving carriage 9 always moves the same amount (the amount necessary to insert a one and one-half inch needle. Actually, to be precise, the carriage motor 17 always moves one and one-half inches plus a little extra, the extra being a distance necessary to recess the tip of a one and one-half inch needle 5 within the inside of the needle shield 67. This recess amount would be approximately $3/32$nds of an inch from the distal surface. Therefore, above where the words one and one-half inches of travel occur, the actual distance traveled would be 1 and $19/32$nds inches. As shown in FIG. 13, the needle 5 is shown with its tip recessed into the housing. This recess is $3/32$nds inch, and the needle is a one and one-half inch needle. Therefore, to insert this needle, or any shorter needle, fully into the patient, the moving carriage 9 must move a total of $1^{16}/32$nds plus $3/32$nds equals $1^{19}/32$nds inches.

Other injectors in the patent record either only accommodate one needle length or they provide some mechanical means of adjusting the insertion depth. If so, a variable needle length needle combined with the depth adjustment can result in confusion for the user as to the actual depth they will get because a calculation is now required to get the resulting depth. With the method of this invention, needles from one-half inches or shorter to one and one-half inches long can be used and the needle will always be fully inserted. The user can change the penetration depth by changing the length of the needle. Therefore, there is never any confusion as to the depth of insertion you will get as the needle length is always printed on its package. The user picks the depth administered by selecting the correct needle. "Full Prescribing Information" that is provided with every drug always addresses the needle length because the instructions always encompass the administration of the drug with a standard or non-standard syringe at a minimum, without any accompanying mechanical devices such as this invention. The "Full Prescribing Information" may also address the use of an autoinjector, injection pen device, or custom prefilled syringe, however, if the drug is provided in a syringe fillable format such as a vial, the necessary syringe and needle requirements are addressed. To this inventor's knowledge, no injector has combined a movable carriage gripping the syringe's finger flange 92 with a separate needle guide 70 holding and guiding the distal end of the syringe 30 a fixed distance to accommodate different lengths of needles without having to do a calculation or make an adjustment. If the user needs a one inch deep injection, with this invention, they use a one inch needle to get that depth. No adjustments or calculations are required. The range accommodated is from one and one-half inches to one-half inches or less. Other embodiments (not illustrated) could be scaled so that other depths could be achieved. This embodiment is not intended to limit this aspect of the claims of the invention to one and one-half inches maximum depth or a minimum of one half inches.

Figure 18:
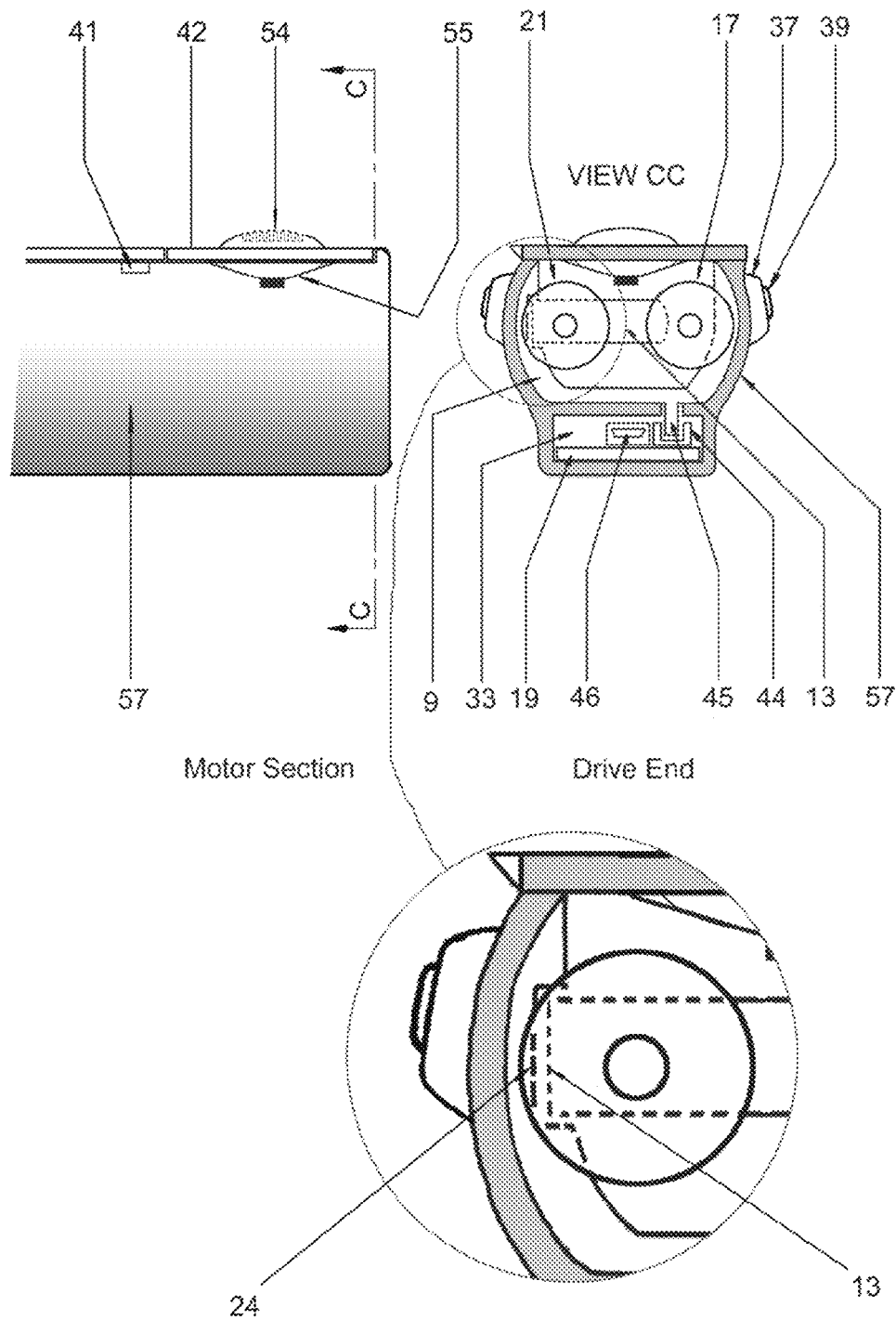
FIG. 18 is a sectional end view of the proximal (drive end) of the autoinjector. It is not specific to either of the two primary embodiments since the portion of the device to the right of the Folding Hinge 49 (the proximal end of the device) is virtually the same between both primary embodiments. The view is accompanied by a portion of the front view for reference.

This movement of 1 and $19/32$nds inches is achieved by the MCU running the carriage motor 17 while monitoring the output of the carriage travel position sensor 44 (see FIG. 18, view CC). The position fin 45 which is attached to the moving carriage 9 and extends below the bottom of the moving carriage 9 and interrupts the light in the carriage travel position sensor 44 (which is mounted on the integrated circuit board 19) except at the travel limits of 1 19/32nds inch and 0 inches where the light reaches the photo sensor in the carriage travel position sensor 44 and signals the position algorithm running in the MCU which then stops the carriage motor 17. Thus, the position algorithm can insert a needle of various sizes automatically all the way into the patient and then remove the needle after the medicament has been dispensed.

Attached to the proximal outside of the moving carriage 9 and moving with it forwards and rearwards, is the actuator motor 21. The shaft of the actuator motor 21 is attached to the actuator lead screw 25, preferably by laser weld. Riding on the actuator lead screw 25 is the actuator lead screw nut 26 which is attached to the actuator 13 which is prevented from rotating due to the actuator guide 24 in which the actuator 13 rides forward and rearward (see FIG. 18). Thus, when the actuator motor 21 rotates, the actuator lead screw 25 rotates, and the actuator lead screw nut is forced to travel forwards and rearwards on the actuator lead screw 25. Attached to the actuator 13 is the actuator spring 12 which presses on the plunger thumb pad 11 and forces the syringe plunger rod 14 into the barrel of the syringe 30. Note: the captive mechanism required for withdrawal of the syringe plunger rod 14 in the aspirate analysis embodiment is not illustrated. In the pictured embodiment, the actuator 13 can push the syringe plunger rod 14 into the syringe 30, but then the plunger is left in the syringe 30 after the injection and the actuator 13 is returned to its proximal "home" position. As mentioned previously, as the actuator 13 is pushing the syringe plunger rod 14, the actuator spring 12 is partly compressed, however, when the syringe plunger seal 28 reaches the distal end of the syringe barrel, it can travel no further and the syringe plunger rod 14 stops moving forward. However, the actuator motor 21 is still rotating which causes the actuator spring 12 to become further compressed. This spring force onto the actuator 13 is reflected back through the actuator lead screw 25 to increase the torque on the actuator motor 21. Since torque is proportional to motor current and this current is being monitored by the MCU, the positioning algorithm can detect when the syringe plunger rod 14 has dispensed the entire amount of medicament and stop the actuator motor.

FIG. 16 depicts a front view of the left side of the injector housing. The access cover, syringe section 36 and the access cover, carriage section 40 are shown at the top edge. When both access covers are in the closed position and the injector housing is straightened and the thumb buttons 39 are snapped into their holes in the latch protrusions 37, the two access covers come together and interlock at the access cover interface 38. This interface where the two access covers meet when the injector is unfolded, force the two covers to move as one. For the injector to be operational, both the access cover closed sensor, syringe section 34 and the access cover closed sensor, carriage section 41 must be detected as closed and the unfolded and latched sensor 107 (see FIG. 22) must detect that the housing has been unfolded and latched into place. Once the injector is locked into the unfolded position, the two covers can be flipped open as one cover, their hinges (see FIG. 15b, view HH, or FIG. 20, view HH) having springs (not shown) which bias the lids to either the closed or open positions. These access covers along with the internals provide for the syringe 30 to be loaded horizontally into the injector, thus providing an improvement over other patents which require the syringe to be inserted axially into the housing and then the two pieces of the housing are screwed together.

The access cover closed sensor, syringe section 34 (see FIG. 16 and FIG. 22) works by continuity of circuit. That is, a conductive spring 83 which is mounted in the access cover, syringe section 36 presses on the access cover closed sensor, syringe section 34 when the lid is closed. When it is so pressed against the circuit, continuity is established because the spring is conductive. The completed circuit then signals to the MCU that the access cover, syringe section 36 is in the closed position. The unfolded and latched sensor 107 works by the same principle. A conductive spring 106 mounted on the distal face of the moving carriage and electronics housing 57 between the upper section and the electronics bottom compartment 33 presses on the continuity circuit that constitutes the unfolded and latched sensor 107 when the housing is unfolded and latched into place. And therefore signals the MCU that the injector is in the unfolded and latched position.

Next to the access covers on the top of the proximal end of the housing is the access cover, motor section 42 (see FIG. 21) which contains the speaker grill 54 and underneath the grill, mounted to the underneath side of the access cover, motor section 42 is the speaker 55.

As illustrated in FIG. 16, mounted on the left side of the injector housing, on the outside of the moving carriage and electronics housing 57 is the operator key pad 86 which contains in the bottom row, the scroll left button 87 and the scroll right button 88 which scroll the available selection for the current menu onto and off of the operator display 85 (see FIG. 21). In the top row are the enter button 90 which accepts the currently selected option, and the return button 89, which takes the user up one level in the menu system. The menu system's current menu and option selection (as well as animation graphics and injector status) is displayed in the operator display 85 which is pictured in FIG. 21. Above and to the right of the operator display 85 is the writing surface 95 which could either be a "white board" surface or more preferably, a "pencil marking" surface which can be used to record such information as patient name or wrist number, drug, current injector mode, etc. The "pencil marking" surface also provides for easy markable tape removal wherein, information which changes frequently can be written on a piece of markable tape affixed to the pencil marking surface and quickly removed and replaced with new information without having to erase actual pencil writing.

Referencing FIG. 18, view CC, one can see the electronics bottom compartment 33 which houses the integrated circuit board 19. On this circuit board and positioned flush to the proximal end of the moving carriage and electronics housing 57 is the micro USB port 46. This is used to connect to a personal computer or an AC charging station, or an AC wall charger. FIG. 18 also provides a view of the carriage motor 17, the actuator motor 21 and the actuator 13 as it fits into the actuator guide 24. The latch protrusions 37 with the thumb buttons 39 can be seen sticking out from the upper sides of the housing.

The battery 18 and the haptic motor 129 (not pictured) are located in the battery and vibrator compartment 72 which is located in the syringe section housing 69 in a compartment beneath the syringe portion of the upper housing (see FIG. 15a, view HH, or FIG. 20, view HH).

FIG. 23 illustrates the integrated circuit board 19 in electrical schematic form. Note, most bypass capacitors and some other discrete passive components are not shown. Sections marked AA, BB, CC, DD, and the TENS circuit are further illustrated in detail in subsequent figures. The central item of the integrated circuit board 19 is the Micro Controller Unit (MCU) 125 which is a Microchip dsPIC33FJ128GP804 digital signal controller (DSC). The dsPIC33FJ model is a 16 bit microcontroller with a built in digital signal processor (for processing the audio features of the autoinjector) and operates up to 40 MIPS. The DSC CPU has a 16 bit data path and 24 bit instructions and two 40-bit accumulators. On-chip are 16 k of RAM and 128 k of flash program memory, eight DMA channels, a real-time clock/calendar, 4 PWM outputs, flexible digital IO (configurable), wake-up on pin change-of-state, Analog-to-Digital Converters (ADC), Stereo Audio Digital-to-Analog Converters (DAC), two SPI serial ports and one I2C serial port, all of which are utilized in implementing the functions and algorithms of this autoinjector.

Continuing at the top left, is the battery 18 which is preferably a rechargeable battery or batteries. If they are AAA batteries, the user can use non-rechargeable or they can use rechargeable batteries which can be charged while in the injector at the current supplied by the USB port (limited to 85 mA or 450 mA), or they can be removed from the injector and placed into a fast-charge device. This provides more flexibility to the user. If the battery is a single cell lithium ion, then the EaglePicher 072248 Carefree Li-Ion Prismatic cell or equivalent is sufficient. If the battery is composed of three AAA cells, the Duracell DC2400 or better is sufficient as a rechargeable battery and the Energizer EA92 or better is sufficient as a non-rechargeable battery.

Attached to the battery 18 output is a voltage divider whose output is measured by AN2, an analog-to-digital converter channel of the MCU. This provides information to the control logic of what the charge on the battery is and in particular, it provides information of when the battery is getting low. The charge on the battery can be illustrated by a graphic on the operator display 85 or announced by human spoken language.

Next is the 3.3 v regulator 121, which supplies the logic voltage for all of the digital circuitry and some of the analog circuitry. This is a very low drop out regulator which allows the most mAh (milliamp hours) of use from lithium ion batteries (to the knee of their discharge curve). The 3.3 Volt Regulator 121 is an ST LDS3985xx33 or equivalent. It provides ultra low drop out BiCMOS 3.3 volts of regulation for use with very low ESR output capacitor. The regulator provides up to 300 mA. It is stable with ceramic and high quality tantalum capacitors. The ultra low drop voltage, low quiescent current and low noise makes it suitable for low power applications in battery powered systems.

The next regulator; 3.0 v regulator 122, supplies the power to the two DC motors. Using a separate regulator provides for better isolation and the ability to match the motor voltage specification. The 3.0 v regulator 122 is an ultra low drop out, low noise voltage regulator. This is an ST LDS3985xx30 or equivalent. It provides ultra low drop out BiCMOS 3.0 volts of regulation for use with very low ESR output capacitor. The regulator provides up to 300 mA. It is stable with ceramic and high quality tantalum capacitors. The ultra low drop voltage, low quiescent current and low noise makes it suitable for low power applications in battery powered systems.

Section AA illustrates the battery charger 123 and the USB port 124 which work together. When the USB port is plugged into a USB master, the master communicates information of whether "high power" or "low power" is available. These are a maximum of 500 mA or 100 mA respectively. This Section AA circuit (further illustrated in FIG. 26) provides for control of the battery charger so that the correct current is drawn from the USB port to charge the battery. The battery charger 123 provides for trickle charge, constant current and constant voltage charging with timeout protection. The USB port 124 is a protocol converter which translates USB communications into SPI (Serial Peripheral Interface) signals and interfaces to one of two SPI ports on the MCU.

Heading down the left side of the schematic, we encounter the external flash memory with SPI port 126. The flash memory is used specifically to store human spoken language, ringtones, and audio queues. The human spoken language is pre-recorded phrases, directions, instructions, etc. The ringtones are used during the injection and also for the reminder alarms when injections are due. The audio queues let the user know when the injector is ready to inject, when the injection is complete, and other functions such as when keys are pressed. The flash memory 126 shares the CS (Chip Select) pin of an SPI port with the operator display 85. It is shared by multiplexing the line with one third of a triple SPDT switch 138. The flash memory is an SST (Silicone Storage Technology) SST25VF080B-80-4I-QAE-8 Mbit Flash with SPI serial interface or equivalent. It writes (Program or Erase) with a single power supply of 2.7-3.6V. The memory array is organized in uniform 4 Kbyte erasable sectors with 32 Kbyte overlay blocks and 64 Kbyte overlay erasable blocks.

Next is the photointerrupter 127 which houses both a photo emitter and a photo transistor in one package which has a slot between them. When the position fin 45 that extends down from the moving carriage 9 is present in this slot, the light is interrupted. This position fin 45 has a length such that, at the ends of travel, the position fin 45 is not present in the slot, thus signaling the end of travel by turning on the phototransistor. The photointerrupter 127 is a Rohm RPI-0226 or equivalent, which uses a single chip molded technology in place of the conventional casing method. This allows for an ultra-small package. A slit in the package allows an outside "interrupter" (the (45) "Position Fin") to block light from reaching the phototransistor from the photo emitter.

Continuing down we encounter the haptic motor 59 and it's power MOSFET 128 driver chip. The MOSFET is driven by the OC3 PWM output of the MCU. Driving the MOSFET with PWM provides for speed control of the DC haptic motor. This effectively varies the vibration frequency and is used as one of the biofeedback mechanism of the injector. The power MOSFET 128 is an N-Channel enhancement mode field effect transistor, and is a Fairchild 2N7002 or equivalent, which is designed to minimize on-state resistance and current switching up to 400 mA and the gate threshold is at logic level.

Next, digital inputs to the MCU are provided to the operator keypad 86 and the initiate button 6. These inputs of the MCU are configured as "Change Notification" inputs wherein, change of state of an input causes an interrupt of the processor. This is useful in that the buttons don't have to be continually scanned, which saves processor clock cycles.

Further down, is Section DD which is the DC to DC converter which steps up the 3.3 volt logic regulator to 12.5 volts needed to run the OLED operator display 85. Central to this circuit is the Linear Tech LT3580 charge pump converter. Detail of this circuit is found in FIG. 27. This circuit also provides power to the multiplexers of Section CC.

Next is the operator display 85. This is an Organic Light Emitting Diode (OLED) display with a matrix size of 128 columns by 32 rows of pixels. Being LED in nature, it is bright and viewable form a wide symmetric angle. The part contains its own driver electronics and interfaces to the MCU through an SPI port. Its CS (Chip Select) is shared with the flash memory through the multiplexer 138. The display is an OSD12832P0906-10 by OSD Displays or an OE19M0064-Y-E by Truly Semiconductors. Both are 128×32 pixel OLED displays with integrated SSD1305 driver by Solomon Systech featuring an SPI interface.

Next is a 32.768 kHz quartz watch crystal 143. This low frequency source provides slow MCU clock cycles during sleep mode. Sleep mode is used primarily to keep the real-time clock-calendar alive as it stores and operates to sound injection reminder alarms according to the patient's schedule.

Last down the left side of the schematic, is the 3.3 volt regulator 129 for the analog-to-digital module of the MCU. Using a separate reference provides for isolation and high accuracy of conversion. This particular reference has a power capability to supply the MCU analog module plus the power to drive the circuit of Section CC. The 3.3 v regulator 129 is a National Semiconductor (now TI) LM4132 Precision Low Dropout voltage reference or equivalent. This device performs comparable to the best laser-trimmed bipolar references due to the use of EEPROM registers for correction of curvature, tempco, and accuracy on a CMOS bandgap architecture that allows package level programming to overcome assembly shift. The LM4132 is a reference that is capable of delivering up to 20 mA of current, and therefore, is usable of supplying the current requirement of the AVdd pin specification, yet it is a precision reference as opposed to a "regulator".

Continuing counter clockwise up the right side of the schematic is the IO Expander with I2C 135. This is a discrete IO peripheral port expander which interfaces with the MCU through an I2C serial interface. The MCU is a 44 pin device which is limited for the number of connections necessary. Therefore, the I2C serial interface is used to expand the IO capability of the processor beyond its footprint by addressing the IO expansion. The IO Expander's inputs also feature Change Notification and therefore, the inputs don't have to be continually scanned but rather, when an input changes, an interrupt to the MCU is created. The IO expander with I2C 135 is a Microchip MCP23017 or equivalent. Along with the (136) and (142) "Digital Potentiometers" it shares the MCU's I2C buss. The IO expander provides two ports of eight pins which can be configurable as active-high, active-low or open-drain. Each port has a separate interrupts to the MCU, however, they will be internally OR'ed in this application. The pins can, when configured as inputs, provide an interrupt on change from configured register defaults or on pin change of state. This is utilized for the inputs from contact switches such as the "Lid Closed" sensors and other inputs.

Continuing upward we encounter the audio output components. These are the digital potentiometer 136, the audio amplifier 137, and the speaker 55. These are driven by one channel of the MCU's stereo DAC (Digital to Analog Converter). This is a differential output which drives the differential input of the class D audio amplifier. First, however, the differential outputs pass through a digital potentiometer 136 which sets the gain of the audio amplifier 137. The digital potentiometer 136 is controlled through the I2C serial interface of the MCU. The digital potentiometer 136 is a Microchip MCP4642 Dual Rheostat or equivalent with I2C port. It provides digital potentiometer functionality by combining internal resistors to produce a total resistance between terminals. It is used in this application to vary the gain (volume) of the audio amplifier 137 without providing a traditional potentiometer and the associated costs and considerations of providing user access to its setting. In this case, the volume of the audio amplifier is controlled by the MCU which allows the user to change the volume through the menu/display system. The audio amplifier 137 is an ST TS4962 filter-free mono class D audio power amplifier or equivalent. This power amplifier provides a standby mode so it is not using power except when needed. The unit will output 1.7 W into an 8 ohm speaker with 10% THD+N maximum. That is quite sufficient to hear human speech clearly when the autoinjector is behind you giving a buttock injection, even for the hard-of-hearing. Typical signal to noise ratio is 85 dB. The speaker 55 is a PUI AS01508MR-R, 1.2 watt, 15 mm speaker or equivalent, with 8 ohm impedance, mylar cone and Nd—Fe—B magnet.

Continuing counter clockwise is Section CC which contains the skin contact sensor circuit. This is a 0.1 microamp current source which causes a voltage drop across the conductive skin contacts and the skin and the skin itself. The current source is only 0.1 microampere in order to limit the voltage drop to 3 volts even with 30 megaohms of resistance between the conductive pads, as can be presented by dry skin. The 3 volt drop fits within the measurable range of the AN1 Analog-to-Digital conversion channel of the MCU. In order to allow the TENS circuit to utilize the same conductive skin pads, high voltage multiplexers 141 and 133 are provided since the TENS voltage can reach 70 volts. Further detail of Section CC can be found in FIG. 24.

Last in this counter clockwise loop of the schematic, is Section BB which illustrates the PWM H-Bridge Driver 130 and current sensing circuit for the carriage motor 17 and the actuator motor 21. Two PWM outputs from the MCU (OC1 and OC2) are multiplexed between the two motor H-Bridge circuits by multiplexer 132. The dual H-Bridge Driver 130 contains two separate H-Bridges. The H-Bridge provides for two PWM signals to control a motor's velocity and direction. The current sensing circuit is accomplished by channeling the armature current through a low-side shunt resistor and accompanying Op-Amp circuitry whose output is measured by the Analog-to-Digital Converter channel AN0. Further details of this circuit are provided in FIG. 25.

FIG. 24 illustrates Section CC which is the skin contact conductance sensing circuit. An Op Amp 131 provides a 0.1 microamp current source when skin completes the circuit between two electrically conductive pads. These pads are arranged as two pairs of contacts. A multiplexer 133 switches rapidly between the pairs of contacts. The voltage drop produced by the resistance between the electrical pads is measured by the AN1 Analog-to-Digital input of the MCU. The 0.1 current source is developed by the Op Amp 131 maintaining a 0.05 v drop across resistor R1, a % resistor. The non-inverting input of the Op Amp 131 receives the 0.05 v input reference from a voltage divider made of 1% resistors. The Op Amp 131 is a Linear Technology LT6004 operational amplifier or equivalent. The LT6004 is a dual op amp designed to operate at low voltage, and maximize battery life and performance for portable applications. It provides rail-to-rail operation. It draws only 1 µA maximum quiescent current. It has an input offset voltage of 500 µV maximum with a typical drift of only 2 µV/° C., input bias current of 90 pA maximum, open loop gain of 100 k and the ability to drive 500 pF capacitive loads. The small bias current is required so that the 0.1 microamp current can be obtained without offset. Since the TENS function also uses the conductive electrical pads, the TENS is multiplexed in with the multiplexer 141. Both the 133 and 141 multiplexers are high voltage switches (+70 v). This is necessary because when the TENS current is passing through the electrical pads, both multiplexers must withstand the high voltage and provide isolation. The multiplexers 133 and 141 are Maxim Quad SPST+70 v analog switches with a low on-resistance of 10 ohm max and rail-to-rail operation. The MAX 14757 is a quad normally open SPST switch with low on-leakage current of 0.01 nA (typ.). Because the multiplexers must have their Vcc pin=>than the switch voltage and the minimum Vcc is 10 v, the multiplexers are powered by the DC to DC converter 134 when the circuit is measuring conductance across the pads. The DC/DC converter 134 supplies 12.5 volts to the operator display 85, and this meets the 10 v minimum supply for the multiplexers. When the TENS is being applied to the electrical pads, the multiplexers receive their Vcc power from the TENS Vout, which varies to maintain current, but this voltage is always equal to the switched voltage since the switched voltage is the TENS Vout chopped by a PWM function (see the TENS circuit of FIG. 28).

FIG. 25 illustrates Section BB which is the H-Bridge driver to the motors and the motor current sensor. PWM signals OC1 and OC2 from the MCU are multiplexed through multiplexer 132 to one of two sets of FETs in the Dual H-BridgeFET driver 130. One of these driver sets is shown in Section BB. The current supplied by the 3.0 v reference 122 is gated through two of four FET's depending upon the direction the motor is being driven or if it is in brake or coast mode. This current exits the H-Bridge driver 130 and passes through a current shunt resistor 139 of 0.1 ohms before returning via the ground path back to the 3.0 v reference 122. The voltage across this shunt resistor 139 is scaled by an Op Amp 131 and the scaled output is measured by the AN0 Analog-to-Digital channel of the MCU. The dual H-Bridge FET driver 130 is a Toshiba TB6590FTG monolithic dual DC motor driver IC or equivalent. The TB6590TG utilizes LDMOS output transistors with low ON-resistance and operation down to 2.2 v. The TB6590FTG provides four operation modes selectable via IN1 and IN2: Forward, Reverse, Short Brake, and Stop. These modes are affected by PWM inputs applied by the MCU. The IC also provides a Standby pin which will be asserted whenever the motors aren't required, thus saving significant power for a hand-held battery powered device. The Op Amp 131 is a Linear Technology LT6004 operational amplifier or equivalent. The LT6004 is a dual op amp designed to operate at low voltage, and maximize battery life and performance for portable applications. It provides rail-to-rail operation. It draws only 1 µA maximum quiescent current. It has an input offset voltage of 500 µV maximum with a typical drift of only 2 µV/° C., input bias current of 90 pA maximum, open loop gain of 100 k and the ability to drive 500 pF capacitive loads. The small offset voltage is necessary for measuring the small shunt voltage drop without offset error.

FIG. 26 illustrates Section AA which is the combined battery charger 123 and the USB to SPI protocol converter 124. A USB cable plugs into micro-USB port 46. Since this port is exposed, it is susceptible to electrostatic discharge. Therefore, the port is protected with a common mode filter with ESD protection 140 on the two data lines, and a zener diode on the power pin. The filtered data lines then terminate on the USB to SPI protocol converter 124 which converts between USB and SPI serial communications. The converted serial data is connected to one of the two SPI ports on the MCU. The USB to SPI protocol converter 124 responds to signals according to the USB 2.0 specification. Specifically, USB devices must support suspend mode wherein the devices must consume very small power. This state is asserted on the GP2 (CS2) pin which is connected to the enable pin EN of the battery charger 123, thus disabling system drain on the USB power pin when GP2 is low. Additionally, according to the USB 2.0 specification, the host signals the available power that can be drawn through the port as 'low power' or 'high power', corresponding to 100 mA or 500 mA maximums. This communication is received by the USB to SPI protocol converter 124 and gets set on the GP4 (GS4) pin which is connected to the current PROG pin of the battery charger 123 through a PROG resistor which sets the high power current draw. When the PROG pin is pulled high, low power charging of the battery at 85 mA ensues. If the PROG pin is pulled low through the PROG resistor, a high power mode of 420 mA is provided by the battery charger 123 to the battery. The STAT1 pin causes the connected LED to flash when charge is complete. The STAT2 indicates an error and is connected to an input to the MCU. The battery charger 123 is a Microchip MCP73861-Advanced Single, Fully Integrated Li-Ion, Li-Polymer Charge Management Controller or equivalent. The MCP7386X family of devices features highly advanced linear charge management controllers for use in space-limited, cost-sensitive applications. The devices combine high-accuracy, constant voltage and current regulation, cell preconditioning, cell temperature monitoring, advanced safety timers, automatic charge termination, internal current sensing, reverse blocking protection, charge status and fault indication. The MCP7386X provides a complete, fully functional, stand-alone charge management solution with a minimum number of external components. The MCP73861 is intended for applications utilizing single-cell Lithium-Ion or Lithium-Polymer battery packs. The USB to SPI protocol converter 124 is a Microchip MCP2210 USB to SPI protocol converter or equivalent part. The MCP2210 device is a USB-to-SPI Master converter which enables USB connectivity to the SPI serial port. USB termination resistors are provided within. The MCP2210 also has 256 bytes of integrated user EEPROM and has nine general purpose input/output pins. Seven pins have alternate functions to indicate USB and communication status. Two of these pins are utilized to interface with the battery charger 123 to enable the charger and to the set the charge current depending upon the source.

FIG. 27 illustrates Section DD which is the 12.5 v voltage source for the operator display 85. The central part is the DC/DC converter 134 which is a Linear Technology LT3580 PWM DC/DC converter containing an internal switch. In this circuit, the LT3580 is configured as a boost, capable of generating 12.5 v from the 3.3 v logic supply. In the circuit, the shut down pin is connected to a FET combination which performs the function of disconnect so that the battery is not drained when the converter is off.

FIG. 28 illustrates Section EE which is the TENS generation circuit. A digital potentiometer 144 sets the intensity of the current. It has non-volatile Memory and an I2C serial port for communications with the MCU. This is a Microchip MCP4542 Single Rheostat or equivalent with I2C port. It provides digital potentiometer functionality by combining internal resistors to produce a total resistance between terminals. It is used in this application to vary the intensity of the PWM TENS Generator 145 without providing a traditional potentiometer and the associated costs and considerations of providing user access to its setting. In this case, the intensity of the TENS current can be controlled by the user through the menu/display system from 5 to 20 mA. The actual TENS current is generated by a TENS generator 145 which is a PWM LED driver adapted for TENS generation. This is a Linear Technology LTC3783 PWM LED Driver and boost controller or equivalent. The digital potentiometer 144 controls the current limited through the low side power MOSFET and the PWM signal from pin OC4 of the MCU 125 controls the pulse width and frequency of the power MOSFET.

GLOSSARY TO THE DRAWINGS

1) Guide Tube: Cylindrical tube which the (32) "Syringe Guide" slides forwards and backwards (distal and proximal) to insert the (5) "Syringe Needle" into the patient's tissue.

2) Wire Way: Conduit trough which holds a section of the (48) "Flexible Electric Circuit" and in particular, the section which provides the electrical conductors coming from (31) the "Printed Sensor Board" to the rest of the "Flexible Electric Circuit" which lays flat on the inside of the upper chamber of the (56) "Guide Tube/Syringe Guide Housing" and extends through a slot between the upper and lower compartments of the "Guide Tube/Syringe Guide Housing" into the (58) "Battery and Vibrator Bottom Compartment" and finally passes through the (49) "Folding Hinge" to terminate on the (19) "Integrated Circuit Board".

3) Syringe Guide Grip: Extension up from the (29) "140° semicircle" part of (32) the "Syringe Guide". The "Syringe Guide Grip" is used to hold the (29) "140° semicircle" part of (32) the "Syringe Guide" while inserting and removing the guide into the (56) "Guide Tube/Syringe Guide Housing".

4) Needle Centering Fixture: Molded fixture that is part of (32) "Syringe Guide" which aims the needle straight down the (1) "Guide Tube" when the syringe is so inserted and the flange of the syringe is placed into the (10) "Elastomeric Flange Grip". The "Needle Centering Fixture" is open on top so that (5) the "Syringe Needle" can be slotted into the Fixture. Different Fixture molds can accommodate different needle/syringe types. Shown is a "Needle Centering Fixture" for (20) a "Needle Connector" which accommodates a standard Luer Slip type removable needle.

5) Syringe Needle: Needles from ¼ inch to 1½ inch long and of any gauge can be accommodated by the autoinjector ("device"). Shown is a 1½ inch long needle. Note: the Needle is part of the (30) "Syringe" and is not provided with the "device".

6) Initiate Button: Button to press to begin the "injection process": $1^{st}$, insert needle into tissue by advancing (9) "Moving Carriage", $2^{nd}$, empty contents of syringe by moving the (14) "Syringe Plunger Rod" into the syringe by advancing the (13) "Actuator", $3^{rd}$, remove needle from tissue by retracting (9) "Moving Carriage", and $4^{th}$, retracting (13) the "Actuator". Note, the plunger stays in the fully depressed position when the "Actuator" is retracted. The "injection process" will not begin when the "Initiate Button" is pressed unless the electronics and software algorithm first detects that the (31) "Printed Sensor Board" containing elements of "Sensor Technology" is suitably pressed against the skin. Nonconductive inanimate objects will not be detected by "Sensor Technology" and therefore, the Initiate Button will not be enabled by pressing the "Printed Sensor Board" against such objects. The "Sensor Technology" is calibrated to measure resistance, such as skin resistance. Audio biofeedback provides an indication of how perpendicular the "Printed Sensor Board" is pressed against the skin as well as how steady and firmly pressed. Once the algorithm detects that the "Printed Sensor Board" is adequately pressed, the audio feedback is changed to a "ready" sound and the "Initiate Button" is enabled.

7) Syringe Guide Flange: Square flange molded onto (32) the "Syringe Guide". The "Syringe Guide Flange" is used to attach the Syringe Guide to (9) the "Moving Carriage" and to center the flange end of the Syringe Guide. Note: the actual syringe flange does not fit into the slot that this Syringe Guide Flange occupies. Instead, the syringe flange fits into (10) the "Elastomeric Flange Grip".

8) Seam/Hinge Point: Flush with the bottom of the "device" is a (49) "Hinge" that provides for the "device" to be folded in half; the two ends folding down into the drawing if viewed from the top. Electrical conductors from the (58) "Battery & Vibrator Bottom Compartment" which is located in the (56) "Guide Tube/Syringe Guide Housing" pass through the (49) "Folding Hinge" into the (33) "Electronics Bottom Compartment" of the (57) "Moving Carriage/Electronics Housing" half of the device and terminate onto the (19) "Integrated Circuit Board" located there. On the outside of the device are the (37) "Latch Protrusions" and the (39) "Thumb Buttons" which latch the two halves of the device into the straight operational position at the "Seam/Hinge Point". Pressing the "Thumb Buttons" in allows the device to be folded in half for storage or transport." At the "Seam/Hinge Point", the (22) "Access Cover" (which consists of two covers, one over each half of the device), come together and meet at the "Seam/Hinge Point" and interlock together which forces them to move as one cover when the "device" is unfolded and latched into the straight position. Thus, pushing up to open one cover automatically opens the other cover and vice versa.

9) Moving Carriage: Movable U-shaped carriage that holds and moves the (32) "Syringe Guide" by way of the (7) "Syringe Guide Flange". The "Moving Carriage" also holds the (10) "Elastomeric Flange Grip" which centers the flange end of the syringe, and the "Moving Carriage" contains, as part of its assembly, parts (12), (13), (15), (16), (21), (23), (25), (26), and (27), which make up the actuating system for (14) and (11) the "Syringe Plunger Rod" and "Plunger Thumb Pad". The "Moving Carriage" is moved in a controlled, gentle velocity profile back and forth to insert the needle and remove it by the (17) "Carriage Motor" in conjunction with the (15) "Carriage Lead Screw" and (16) "Carriage Lead Nut" and the motion control software.

10) Elastomeric Flange Grip: a moldable elastomeric insert which centers the syringe barrel and flange end of the syringe in the x, y and z dimensions which affixes the (20) "Needle Connector" here pictured as a Standard Luer Slip Needle (molded-in needles of a glass syringes can also be accommodated) into and against the (4) "Needle Centering Fixture" that is molded into the (32) "Syringe Guide". Different Elastomeric Flange Grips can be used to hold syringes of different lengths. Illustrated is an "Elastomeric Flange Grip" capable of holding either a BD-1 ml plastic Tuberculin syringe, or a Terumo-1 ml plastic Tuberculin syringe. Both are standard Slip Luer syringes used for a multitude of injectables.

11) Plunger Thumb Pad: The part of a syringe that is normally pushed by the thumb to inject liquid into tissue. The "Plunger Thumb Pad" is part of (14) "Syringe Plunger Rod", which is connected to (28) "Syringe Plunger Seal", which is part of (30) the "Syringe", which is not supplied as part of the "device". A "Syringe", when loaded into the AutoInjector, is operated on by the (13) "Actuator" and directly by the (12) "Actuator Spring".

12) Actuator Spring: Cushions the force on the (13) "Actuator" as the (14) "Syringe Plunger Rod" reaches the end of travel (when the syringe becomes completely emptied). The "Actuator Spring" also provides an increasing resistance near the end of travel which causes an increase in motor torque which is accompanied by an increase in motor current, which is sensed by the motor drive electronics and processed by a software algorithm to stop the forward motion provided by the (21) "Actuator Motor".

13) Actuator: A paddle with attached (12) "Actuator Spring" which pushes against the (11) "Plunger Thumb Pad" to inject liquid into tissue. The "Actuator" is attached to (26) "Actuator Lead Screw Nut". As the (25) "Actuator Lead Screw" rotates, the "Actuator" is prevented from rotating by a (24) "Actuator Guide" on the inside wall of (9) the "Moving Carriage" in which the "Actuator" rides back and forth. Since the "Actuator" is attached to the Nut and the "Actuator" cannot rotate, the nut is forced to travel up and down the (25) "Actuator Lead Screw", thus driving the "Actuator" toward or away from the "(11) "Plunger Thumb Pad".

14) Syringe Plunger Rod: The part of a (30) "Syringe" that is connected to (28) the "Syringe Plunger Seal", which forces the liquid ingredients form the syringe through the needle when the "Syringe Plunger Rod" is pressed and advanced by the "Actuator". Note: the "Syringe Plunger Rod" is part of the (30) "Syringe" and is not supplied with the device.

15) Carriage Lead Screw: Is threaded through (16) the "Carriage Lead Screw Nut" which is mounted in the (9) "Moving Carriage". When the "Carriage Lead Screw" rotates, the "Carriage Lead Screw Nut" is pinned in place and therefore is prevented from rotating. Therefore, when the "Carriage Lead Screw" rotates, the Nut travels up and down the Lead Screw, taking the "Moving Carriage" with it (the Nut pushes the "Moving Carriage" back and forth, thus pushing the (5) "Needle" into the tissue and removing the "Needle" from the tissue. Rotational power is supplied to the "Carriage Lead Screw" by the (17) "Carriage Motor".

16) Carriage Lead Screw Nut: A Lead Screw Nut which is threaded onto the (15) "Carriage Lead Screw" and pinned in place in the wall of the (9) "Moving Carriage". Because the "Carriage Lead Screw Nut is prevented from rotating when the (15) "Carriage Lead Screw" is rotated by the (17) "Carriage Motor", the "Carriage Lead Screw Nut" is forced up and down the "Lead Screw" and therefore translates the torque of the (17) "Carriage Motor" to the linear motion of the (9) "Moving Carriage".

17) Carriage Motor: A DC Gear Motor which receives energy from a PWM driver on the (19) "Integrated Circuit Board" and produces rotational energy. The motor's rotational velocity is controlled so that its motion is smooth yet swift and the velocity profile is a modified parabola. The "Carriage Motor" drives the (15) "Carriage Lead Screw) and the (16) "Carriage Lead Screw Nut" which rides on the "Carriage Lead Screw" but is held stationary in the wall of the (9) Moving Carriage", thus producing linear motion to insert a full 1½ inch needle in about one second. Shorter needles are inserted in less time. The motion control algorithm executed in software receives information of when the motor driven (9) "Moving Carriage" has reached the travel limit in each direction via discrete inputs. The "Carriage Motor" always drives the (9) "Moving Carriage" the same distance with each "Needle" insertion and extraction cycle. That distance is the distance from the tip of the (32) "Syringe Guide" to the inside of the (31) "Printed Sensor Board" minus a little bit of clearance. This arrangement provides for the use of any length of "Syringe Needle" from ¼ inch to 1½ inches.

The following are the approximate specs of the carriage motor:

Assuming Lead Screw pitch=L=3.18 mm/rev

Converting: (3.18 mm/rev)/2 pi rad/rev)=0.506 mm/rad or $5.06 \times 10^{-4}$ m/rad And assuming Screw Eff=0.75

And F=sticky friction of Moving Carriage plus load=1.4 N

And $S_L$=Moving Carriage travel velocity=30 mm/sec $T_{travel}$=Torque of Gearmotor output at travel velocity= (1.4 N*$5.06 \times 10^{-4}$ m/rad/Eff=0.00708/0.75=0.00095 Nm/rad=0.94 mNm/rad=0.094 Ncm/rad $RPM_L$ of Gearmotor at travel velocity=(30 mm/sec)*(rev/3.18 mm)*(60 sec/min)=566 RPM of gearbox output shaft.

$T_{stall}$ (Equating the travel torque to 50% of stall torque gives) 0.94 mNm/0.5=1.88 mNm No Load Speed=1132 RPM since y=mx+b and m=−(566/(1.88-0.94))=−602 and therefore b=602 (1.88)=1132 RPM 18) Battery: is a battery (or batteries) which supplies its power to the (19) "Integrated Circuit Board" and is either a rectangular shaped single cell rechargeable lithium ion battery or three rechargeable AAA lithium cells or three non-rechargeable AAA cells. In the case of the rectangular battery, the "Integrated Circuit Board" will include a (123) "Battery Charging Circuit" and the battery will receive its charge through an attachable USB cable which can plugged into a USB port on a personal computer or any powered USB port, or a 5 volt DC wall plug adaptor (also known as a wall cube) equipped with a USB jack. If the battery is a single cell lithium ion, then the EaglePicher 072248 Carefree Li-Ion Prismatic cell or equivalent is sufficient. If the battery is composed of three AAA cells, the Duracell DC2400 or better is sufficient as a rechargeable battery and the Energizer EA92 or better is sufficient as a non-rechargeable battery.

19) Integrated Circuit Board: Is a printed circuit board mounted in the (33) "Electronics Bottom Compartment" underneath the (9) "Moving Carriage" and contains a (125) "Microcontroller", a (130) "Dual H-bridge" to drive the (17) "Carriage Motor" and (21) "Actuator Motor", a (122) "3.0 Volt Regulator" for the dual H-bridge, a separate (121) "3.3 Volt Regulator" for the rest of the electronics, a current sensor circuit to detect (21) "Actuator Motor" current, a 0.1 micro amp current source circuit to detect skin contact conductance, a (120) "Op Amp" for the current source and current sensor circuits, a (133) "Multiplexer" for the skin contact sensor, a (137) "Audio Amp" to power the (55) "Speaker", a (136) "Programmable Pot" controlling the audio amp's gain, a (126) "EEPROM" used to house the audio data, a (127) "Photointerrupter" to detect carriage position, a (128) "Power MOSFET" to drive the (129) "Haptic Motor" and a (124) "USB Controller" and (46) "Micro USB Connector", plus resistors, capacitors, diodes, etc, and electrical connectors for cables and flexible printed circuits which connect it to the various peripherals.

20) Needle Connector: specifically refers to the shape of a removable needle connection, or the shape of the distal end of a glass syringe with a molded-in needle. In this example, a popular type removable needle, the Luer Slip, is illustrated. The (32) "Syringe Guide" in this case has a (4) "Needle Centering Fixture" so shaped that a standard Luer Slip needle connector will fit into it snuggly". By changing the shape of the (4) "Needle Centering Fixture" that is part of the (32) "Syringe Guide", other types of needles can be accommodated including glass syringes with molded-in needles. Therefore, most needle/syringe combinations from luer to glass and from 1 ml to 3 ml can be accommodated by changing the "Syringe Guide" to the type of needle/syringe combination that is required. A few types (designs) of "Syringe Guides" can in this way accommodate many needle/syringe combinations.

21) Actuator Motor: A DC Gear Motor which receives energy from a PWM driver on the (19) "Integrated Circuit Board" and produces rotational energy. The motor's rotational velocity is controlled so that its motion is smooth. The "Actuator Motor" is connected to the (25) "Actuator Lead Screw". The rotation of the "Lead Screw" pushes the (14) "Syringe Plunger Rod" by way of the (13) "Actuator" attached to the (26) "Actuator Lead Screw Nut" that is riding on the "Actuator Lead Screw". The motion control algorithm executed in software receives information of when the motor driven (13) "Actuator" has pushed the (14) "Syringe Plunger Rod" to its end-of-travel by way of an increasing linear force exerted by the (12) "Actuator Spring". The increasing force is sensed because it results in an increasing torque on the motor which results in increased current to the motor. The motor current is monitored by a current sensor that is part of the (19) "Integrated Circuit Board". When the algorithm determines that the (14) "Syringe Plunger Rod" has been pushed to its end-of-travel, the "Actuator Motor" is reversed and the "Actuator" is returned to its starting position in the back of the (9) "Moving Carriage". Again, the end of this travel is sensed by the (23) "Actuator Return Spring" which again causes an increase in motor current which motion control algorithm determines to be the return end-of-travel.

The following are the approximate specs of the actuator motor:

Assuming Lead Screw pitch=L=3.18 mm/rev.

Converting: (3.18 mm/rev)/2 pi rad/rev)=0.506 mm/rev or 5.06×10^-4 M/rad

And assuming Screw Eff=0.75

And F=sticky friction of Actuator plus load=3.5 N

And $S_L$-Actuator travel velocity=10 mm/sec $T_{travel}$=Torque of Gearmotor output at travel velocity=3.5 N*5.06×10^-4 m/rad)/Eff=0.00177/0.75=0.00236 Nm/rad=2.36 mNm/rad=0.236 Ncm/rad $RPM_L$ of Gearmotor at travel velocity=(10 mm/sec)*(rev/3.18 mm)*(60 sec/min)=189 RPM of gearbox output shaft $T_{stall}$ (Equating the travel torque to 70% of stall torque gives) 2.36 mNm/0.7=3.37 mNm No Load Speed=630 RPM (since y=mx+b and m=-(189/(3.37-2.36))=-187 and therefore b=187 (3.37)=630 RPM 22) Access Cover: Two hinged covers, one over the (32) "Syringe Guide" section and one over the (9) "Moving Carriage" section. The two covers dove-tail together when the "device" is unfolded and latched in the straight position and the two covers act as one. Friction latches keep the "Access Cover" in position and digital sensors ensure that the "Access Cover" is in the closed position for operation of the motors. The "Access Cover" is opened by two overhanging sections at each end, which are easily pushed open by the thumbs.

23) Actuator Return Spring: is located on the back wall of the (9) "Moving Carriage" but it may also be located on the (13) "Actuator" opposite the (12) "Actuator Spring". The purpose of the "Actuator Return Spring" is to provide the position algorithm with feedback as to when the "Actuator" has been returned to its starting position. It does this by causing an increase in torque on the (21) "Actuator Motor" which is sensed as an increase in motor current.

24) Actuator Guide: A slot in which the (13) "Actuator" rides and is prevented from rotating as the (25) "Actuator Lead Screw" rotates. Since the (13) "Actuator" is attached to the (26) "Actuator Lead Screw Nut", when the "Actuator Lead Screw" rotates, the "Actuator" is forced toward and away from the (11) "Plunger Thumb Pad".

25) Actuator Lead Screw: Is threaded through (26) the "Actuator Lead Screw Nut" which is attached to the (13) "Actuator" in the (9) "Moving Carriage". When the "Actuator Lead Screw" rotates, the "Actuator Lead Screw Nut" is prevented from rotating because it is attached to the "Actuator" which rids in the (24) "Actuator Guide". Therefore, when the "Actuator Lead Screw" rotates, the Nut is forced to travel up and down the "Actuator Lead Screw". When the "Actuator Lead Screw" rotates to force the "Actuator" toward the "Needle End" of the device, it pushes on the (11) "Plunger Thumb Pad" forcing liquid from the "Syringe" and into the tissue. Rotational power is supplied to the "Actuator Lead Screw" by the (21) "Actuator Motor".

26) Actuator Lead Screw Nut: A Lead Screw Nut which is threaded onto the (25) "Actuator Lead Screw" and attached to the (13) "Actuator". Because the "Actuator Lead Screw Nut is prevented from rotating when the (25) "Actuator Lead Screw" is rotated by the (21) "Actuator Motor", the "Actuator Lead Screw Nut" is forced up and down the "Actuator Lead Screw" and therefore translates the torque of the (21) "Actuator Motor" to the linear motion of the (13) "Actuator".

27) Support Unit: A sleeve bearing support for the end of the (25) "Actuator Lead Screw". The "Support Unit is fit into the forward wall of the (9) "Moving Carriage" next to the compartment that holds the (10) "Elastomeric Flange Grip".

28) Syringe Plunger Seal: Is connected to the end of the (14) "Syringe Plunger Rod". The "Syringe Plunger Seal" forces the liquid from the "Syringe" when the "Syringe Plunger Rod" is pushed in by the (13) "Actuator. Note, the "Syringe Plunger Seal" which is part of (30) the "Syringe", is not supplied as part of the "device".

29) 140° Semicircle: Is part of the (32) "Syringe Guide". The "140° Semicircle" is actually a 140° section of a cylinder, which forms the structural connection between the (7) "Syringe Guide Flange" and the (4) "Needle Centering Fixture". The "140° Semicircle" also supports the (3) "Syringe Guide Grip" which are extensions of the "140° Semicircle" which protrude up toward the inside of the (22) "Access Cover". The "140° Semicircle" is only 140° of a cylinder, in other words, it is open on top, in order to allow the (30) "Syringe" to be placed within the radius of the cylinder. Specifically, when the "Syringe" is inserted into the "device", its centerline is equal to the centerline of the "140° Semicircle".

30) Syringe: This is not supplied with the "device" but is rather, what the "device" operates on. The "device" is designed in such a way that it can accommodate many different types and sizes of "Syringes". Shown are two different sizes (brands) of 1 ml plastic tuberculin syringes but with 1½ inch needles (to show the maximum needle length). Additionally, the part (5) "Needle" is considered part of the "Syringe" and the device can accommodate any length of "Needle" from ¼ inch to 1½ inches. The "Needle" can be removable, as illustrated by the (20) "Needle Connector" picturing a standard Luer Slip needle connector, or it could be a molded-into-glass syringe needle (not illustrated), or the "Needle" could be a standard Luer Lock needle (not illustrated). This flexibility in accommodating different sizes, styles of syringes and syringe needles is provided by several aspects of the injector. The (32)

"Syringe Guide" is molded plastic and therefore, different molds can accommodate different syringes. To accommodate the different syringe lengths, the (10) "Elastomeric Flange Grip" is also a molded part which can be switched out to accommodate different length and diameters of syringes. The "Elastomeric Flange Grip" is flexible Elastomer so as to offer a push-in and retain effect upon the various syringe types the particular insert is designed for. Different molds can provide for different flange locations. Shown is an "Elastomeric Flange Grip" that can accommodate the two brands of syringe (BD and Terumo) which are also illustrated. To accommodate different needle lengths, the "device" has been designed to have the same stroke length of movement for the (9) "Moving Carriage" and the (1) "Guide Tube" sets this stroke length for the 1½ inch needle. Therefore, smaller needles will still be fully inserted into the tissue since the stroke is still the full stroke.

31) Skin Sensor Support: is a flat surface of plastic with a hole in the middle (for passage of the needle), which is located at the end and perpendicular to the (1) "Guide Tube" and integral to it. The "Skin Sensor Support" provides a flat surface to which the (52) "Skin Sensor Printed Circuit" can be glued.

32) Syringe Guide: This part of the "device" is disposable and comes sterile and individually packaged. The "Syringe Guide" holds and guides the "Needle" and "Syringe" as the "Needle" is inserted into the tissue and the "Syringe" contents are injected. Several "Syringe Guide" designs accommodate different needle/syringe combinations by varying the (4) "Needle Centering Fixture". The "Needle Centering Fixture" is so molded to fit snug with the various removable needles and molded-in needles of glass syringes. Of particular interest would be designs of the "Needle Centering Fixture" that can accommodate Luer type removable needles and various diameters of glass syringes. The various lengths of the various syringe cylinders are not accommodated by the length of the "Syringe Guide" but rather, by the (10) "Elastomeric Flange Grip" which has multiple cavities in which to insert the syringe flanges". This cuts down on the number of permutations between the (20) "Needle Connectors" and number of syringe lengths because all the different lengths of syringes and diameters (between 1 ml and 3 ml syringes in the embodiment shown) can be accommodated by just two "Elastomeric Flange Grips". Only two "Elastomeric Flange Grip" designs (configurations) are anticipated to be required (to accommodate all syringes between standard 1 and 3 ml) because by shifting the location of the recesses between two recesses for one insert to three recesses for the second insert, the location of the recesses is effectively shifted by the with of one recess. Since the insert is an elastomer, this arrangement will allow the various lengths of syringes and sizes of syringes to have their flanges pressed in and gripped by the elastomer. During the injection, due to the (9) "Moving Carriage" moving forward and holding the syringe flange in the (10) "Elastomeric Flange Grip" and the back end of the "Syringe Guide" is the (7) "Syringe Guide Flange" which is slotted into the front of the "Moving Carriage", the motive force to push the needle into the patient is provided. The "Syringe Guide" and specifically, the (4) "Needle Centering Fixture" holds the needle centered as it slides down the (1) "Guide Tube". Different "Syringe Guides" in conjunction with two different "Elastomeric Flange Grips" can accommodate a range of different syringe lengths and capacities as described.

33) Electronics Bottom Compartment: A space below the (9) "Moving Carriage" and the (17) and (21) electric motors and is part of the (57) "Moving Carriage/Electronics Housing". The "Electronics Bottom Compartment" houses the (19) "Integrated Circuit Board".

34) Access Cover Closed Sensor, Syringe Section: is a digital "lid closed" sensor which consists of two neighboring traces on the (48) "Flexible Electric Circuit" or (76) "Flexible Electric Circuit" which extends up to the open edge of the (56) "Guide Tube/Syringe Guide Housing" or the (69) "Syringe Section Housing" and is effected by a (83) "Conductive Spring" on the inside edge of the (36) "Access Cover, Syringe Section" which when closed, completes an electric circuit between the two conductive traces on the "Flexible Electric Circuit". The state of the (36) "Access Cover, Syringe Section" is detected by the microcontroller which detects the closure of the electric trace circuit by a digital input.

35) Thumb or Finger Indentation: This is a slightly concave indentation on the otherwise rounded exterior of the device. There is a matching indentation on the other side of the device which has the (6) "Initiate Button" inside the indentation. These indentations may be of other than oval shape in order to affect an ergonomic hand grip of the device. When a patient is self administering an injection into the outer thigh or gluteus maximus, the thumb of the patient would normally be located into one indentation and the fore finger onto the "Initiate Button" which resides in the other indentation. Alternatively, when a patient is self administering a belly or quadriceps injection, the little finger would normally rest on the "Initiate Button" with the thumb pointing away from the distal end of the injector and the other indentation not used. In this case, the "Initiate Button" would be pressed by the little finger. The "Initiate Button" lying in an indentation facilitates this action.

36) Access Cover, Syringe Section: is an access cover to the syringe section of the injector. It offers protection to the user from motion of the internal components during an injection and hides the syringe from sight. The "Access Cover, Syringe Section" has spring loaded hinges such that it is motivated to spring closed or open from the half way point. To open the cover, a light pressure on its edge upwards and past the half way point causes it to spring open and remain open. Likewise, to close the cover, a light pressure on its edge downwards and past the half way point causes it to spring closed and to remain closed. This downward pressure exerted by its spring hinge to keep the cover closed also causes a (83) "Conductive Spring" on the inside edge of the lid to contact the (34) "Access Cover Closed Sensor, Syringe Section" which is located on the (48) "Plastic Flexible Printed Circuit" which extends up to the open edge of the (56) "Guide Tube/Syringe Guide Housing". When the "Conductive Spring" on the underside edge of the access cover completes an electric circuit between two neighboring traces of the "Flexible Electric Circuit", it provides a sensor input to the microcontroller as a "closed" state of the access cover. The "Access Cover, Syringe Section" must be detected as closed by the microcontroller for motion to occur inside the device. The microcontroller monitors this sensor through the (48) "Flexible Electric Circuit" and requires its "closed" state as a requirement for movement of the motors. The (36) "Access Cover, Syringe Section" has protrusions and indentations on its proximal edge. Likewise, the (40) "Access Cover, Carriage Section" has mating protrusions and indentations on its distal edge such that, when the injector is unfolded and locked into its linear operating orientation, the protrusions and indentations of each access cover become mated and cause the two access covers to operate as one cover. Thus, closing or opening one cover causes both covers to move as one.

37) Latch Protrusion: This slightly raised section of the injector housing with a cavity therein, that is divided between the (56) "Guide Tube/Syringe Guide Housing" and the (57) "Moving Carriage and Electronics Housing" at the (8) "Hinge/Seam Point" of the injector. The left side of the protrusion (distal side) is fitted with and holds or retains about half of the length of a rectangular shaped piece of flat spring steel (not shown) onto which the (39) "Thumb Button" is mounted at one end. The mating right side of the protrusion has a hole through it so that, when the two halves of the device unfolded and are swung into its linear operating position, the (39) "Thumb Button" will pop through the hole, thus latching or locking the two halves into its linear operating position. A similar protrusion and thumb button arrangement or "latch" is located on the other opposite side of the injector from the one depicted.

38) Access Covers Interface: is an interlocking of the (36) "Access Cover, Syringe Section" and the (40) "Access Cover, Carriage Section". Specifically, each lid mechanically interlocks with the other at the interface. The "Access Cover, Syringe Section" has protrusions and indentations on its proximal edge. Likewise, the "Access Cover, Carriage Section" has mating protrusions and indentations on its distal edge such that, when the injector is unfolded and locked into its linear operating orientation, the protrusions and indentations of each access cover become mated and cause the two access covers to operate as one cover. Thus, closing or opening one cover causes both covers to move as one.

39) Thumb Button: is a dome shaped button affixed to a short piece of flat spring steel which is inserted into the (37) "Thumb Button Protrusion" thus anchoring the steel. The button protrudes through a hole in the "Thumb Button Protrusion" which affords a latching effect. To unlatch the injector in order to fold it up for storage or transport, the "Thumb Button" must be pushed in so that it is flush with the inside surface of the hole at which point, the "Thumb Button" will slide out of the "Thumb Button Protrusion" and the device can then be folded. There is an identical "Thumb Button" and "Thumb Button Protrusion" on the opposite side as the one depicted to affect a bilateral stiffness to the injector. Therefore, in order to unlatch the two halves, both 'Thumb Buttons" must be pressed in at the same time before the injector will fold.

40) Access Cover, Carriage Section: is an access cover to the carriage section of the injector. It offers protection to the user from motion of the internal components during an injection and hides the syringe from sight. The "Access Cover, Carriage Section" has spring loaded such that it is motivated to spring closed or open from the half way point. To open the cover, a light pressure on its edge upwards and past the half way point causes it to spring open and remain open. Likewise, to close the cover, a light pressure on its edge downwards and past the half way point causes it to spring closed and to remain closed. This downward pressure exerted by its spring hinge to keep the cover closed also causes the (83) "Conductive Spring" on the inside edge of the lid to contact the (41) "Access Cover Closed Sensor, Carriage Section" which is located on a dedicated "Plastic Flexible Printed Circuit" (not shown) which extends up from the (19) "Integrated Circuit Board" to the open edge of the (57) "Moving Carriage and Electronics Housing" and contains only two electrical traces. When the "Conductive Spring" on the underside edge of the access cover completes an electric circuit between two neighboring traces of the "Flexible Electric Circuit", it provides a sensor input to the microcontroller as a "closed" state of the access cover. The "Access Cover, Syringe Section" must be detected as closed by the microcontroller for motion to occur inside the device. The microcontroller monitors this sensor through the dedicated "Plastic Flexible Printed Circuit" (not shown) and requires a "closed" state of the access cover as a requirement for movement of the motors. The (40) "Access Cover, Carriage Section" has protrusions and indentations on its distal edge. Likewise, the (36) "Access Cover, Syringe Section" has mating protrusions and indentations on its proximal edge such that, when the injector is unfolded and locked into its linear operating orientation, the protrusions and indentations of each access cover become mated and cause the two access covers to operate as one cover. Thus, closing or opening one cover causes both covers to move as one.

41) Access Cover Closed Sensor, Carriage Section: is a digital "lid closed" sensor which consists of two neighboring traces on a dedicated "Flexible Electric Circuit" (not shown) which extends up to the open edge of the (57) "Moving Carriage and Electronics Housing" and is effected by a (83) "Conductive Spring" on the inside edge of the (40) "Access Cover, Carriage Section" which, when closed, completes an electric circuit between the two conductive traces on the dedicated "Flexible Plastic Electric Circuit". The state of the (40) "Access Cover, Carriage Section" is detected by the microcontroller which detects the closure of the electric trace circuit by a digital input.

42) Access Cover, Motor Section: is a lid fixed by screws or other fasteners, and covers the motors and electrical conductors to the motors. The "Access Cover, Motor Section" also supports the (55) "Speaker" for audio feedback. The "Speaker" is protected by the (54) "Speaker Grill" which is molded into the "Access Cover, Motor Section".

43) Access Cover Hinges: These are hinges with a spring mechanism which causes the lid to spring either open or spring closed from a middle position. The result is, when the injector is unfolded and locked the linear operating position and the lids are functioning as one (due to (38) "Access Covers Interface"), you will flip the access covers open by the edges with the thumbs, and then, the syringe is loaded into the device, and then, giving the lids a push downward, they both snap closed completing the (34) and (41) "Access Cover Closed Sensor" circuits and letting the software know that the covers are in closed position. This spring open or closed action is accomplished with a mechanism similar to that described by U.S. Pat. No. 4,993,772 which describes a spring-loaded dual-action hinge assembly.

44) Carriage Travel Position Sensor: This is a photodiode/photo transistor combination which detects if the (45) "Position Fin" is occluding light from the photo diode in reaching the photo transistor, thus indicating the ends of travel of the carriage. The fully retracted carriage position is referred to as the "Carriage Home" position, and the fully extended carriage position is referred to as the "Carriage Travel Limit" position. The (45) "Position Fin" extends from the carriage bottom into the light crossing from the photo diode to the photo transistor, except when the carriage is in the "Home" or "Travel Limit" positions. In these position, the light from the photo diode reaches the photo transistor and this tells the (19) "Integrated Circuit Board" that the carriage has reached these travel positions. The Carriage Travel Position Sensor is an optical sensor commonly referred to as transmission type photo interrupters, and more specifically, this is the typical device used to detect position in optical encoders. It incorporates a photon emitting diode and a photon detecting transistor in one package shaped like a U with the two photo elements facing each other. When an obstruction (the Interrupter) passes inside the U-shape (between the emitter and detector), the light is cut off and this turns the transistor off. This device is used to sense position of the carriage by the (44) "Position Fin" which serves as the "interrupter" which extends underneath the carriage lengthwise of sufficient length to keep the transistor turned off except at the ends of travel (the sensor is positioned half way between the travel limits).

45) Position Fin: An extension of the (9) "Moving Carriage" which protrudes through a slit between the upper and lower compartments of the (57) "Moving Carriage and Electronics Housing" into the (33) "Electronics Bottom Compartment" where the (19) "Integrated Circuit Board" is located and specifically, where the (44) "Carriage Travel Position Sensor" is located just below the "Position Fin". The "Position Fin" performs the function of "Interrupter" to the (44) "Carriage Travel Position Sensor" by blocking light from the photo diode in reaching the photo transistor in all carriage travel positions except the "Home" and "Travel Limit" positions. These positions do not occlude the light and allow the transistor to turn on and indicate to the microcontroller that those positions have been reached by the "Moving Carriage". The microcontroller uses this information in executing the carriage positioning algorithm.

46) Micro USB Port: A jack for attaching a USB 2.0 or later cable used for connecting to either, an AC adapter fitted with a USB jack, or a USB port on a personal computer or other such device for the purpose of charging the device, or a USB port on a personal computer or other such device for the purpose of data communications.

47) Battery/Vibrator Cable: not shown; is a small flexible cable which connects the (18) "Battery" and the (59) "Haptic Vibrator" to the (19) "Integrated Circuit Board". The "Battery/Vibrator Cable passes through the (49) "Folding Hinge".

48) Flexible Electric Circuit: This is a printed circuit of electrical conductive traces on flexible plastic (such as Mylar) which provides connections to the patient's skin via the (52) "Skin Sensor Printed Circuit" (which is part of the "Flexible Electric Circuit") as well as connections to the (53) "Initiate Switch" (located under the (6) "Initiate Button") and to the (34) "Lid Closed Sensor, Syringe Section". The "Flexible Electric Circuit" is shaped in such a fashion that it can lay flat against the inside of the upper compartment of the (56) "Guide Tube/Syringe Guide Housing" and pass through the (2) "Wire Way" and lay flat on the (31) "Skin Sensor Support" to, and also pass through a slot between the upper and lower compartments into the (58) "Battery/Vibrator Bottom Compartment", and then pass through the (49) "Folding Hinge, and terminate on the (19) "Integrated Circuit Board" located in the (33) "Electronics Bottom Compartment" of the (57) "Moving Carriage/Electronics Housing".

49) Folding Hinge: Used to fold the device in half in order to reduce the device length for easy storage or transportation. The hinge provides a spring force which tends to fold the injector in half or straighten the injection into a linear meeting of the two housings when the hinge is rotated close to either of these positions. When the "Folding Hinge" is rotated toward the linear configuration of the injector, the spring in the "Folding Hinge" will try to bring the two housings into a line, however, it will require operator assistance to cause the two (39) "Thumb Buttons" to snap into their detent positions inside the (37) "Latch Protrusions". The "Folding Hinge" provides a path for passage of the (48) Flexible Electric Circuit" and the (47) "Battery/Vibrator Cable" through the hinge.

50) Electrical Trace: an electrically conductive path on the (48) "Flexible Electric Circuit" which is covered with a non-conductive coating.

51) Conductive Pad: an electrically conductive pad on the (48) "Flexible Plastic Electric Circuit" that is not covered with an insulating coating. Thus, the "Conductive Pad" is able to make an electrical connection with another conductive element and complete a circuit, as is the case with the (51) "Lid Closed Sensor, Syringe Section" wherein the (36) "Access Cover, Syringe Section" is equipped with a (83) "Conductive Spring" which completes an electric circuit by bridging two "Conductive Pads" on the "Flexible Plastic Electric Circuit" when the "Access Cover, Syringe Section" is closed. Likewise, the "Conductive Pads" of the (52) "Skin Sensor Printed Circuit" are not covered with an insulating coating and in this case, the patient's skin completes a circuit from one "Conductive Pad" to another.

52) Skin Sensor Printed Circuit: a printed circuit that is part of the (48) "Plastic Flexible Electrical Circuit" that is located on the (31) "Skin Sensor Support". The "Skin Sensor Printed Circuit" is glued to the "Skin Sensor Support" and is connected to the rest of the "Flexible Electric Circuit" via (2) the "Wire Way". The "Skin Sensor Printed Circuit has a hole in the middle (for the needle to protrude) and contains four electrical conductive sensor pads arranged as conductance circuits across the hole, in an x-y sensing arrangement. The "Skin Sensor Printed Circuit" senses conductance provided by skin contact from one conductive pat to another conductive pad across the needle exit hole. That is, there are two electrical circuits in the "Skin Sensor Printed Circuit". One of the electrical circuits, designated the "x" circuit, is from one pad to another pad which is on the other side of the needle hole. The second circuit, designated the "y" circuit, is from another pad to one on the other side of the needle hole and is 90° rotated form the other circuit. The two sets of electrical circuit pads form an x-y arrangement where conductivity between the skin and the pads is measured across the needle hole in two dimensions x and y. The measurement of electrical conductivity between the skin and the conductive pads is provided by the (19) "Integrated Circuit Board" and acted upon by way of the "Skin Sense" algorithm. A measurement of conductivity can be used by the "Skin Sense" algorithm to sense when the "device" is firmly pressed against the skin, and a difference in conductivity between one circuit and the other indicates that the injector is being held at an angle and the dimension of lower conductivity is due to the injector being held at an angle in that dimension. This differential scheme is used to sense if the device is pressed perpendicular to the skin surface in both dimensions and is supplied back to the user as audio and/or haptic feedback. The audio feedback is supplied by the (55) "Speaker and the haptic feedback is supplied by the (59) "Haptic Vibrator". Since the two circuits are measuring across the same skin, any difference between the two conductances indicates that the injector is being held at an angle in the dimension of the circuit that has the lower conductance. Feedback to the user indicating the pressure of the injector against the skin and the angle of the injector as it is held against the skin, is provided by audible tones from the "Speaker" and/or a tactile sense from the "Haptic Vibrator". Feedback can be represented as two audio signals whose tone drops in pitch as conductivity increases, one pitch for each dimension x and y and/or a haptic vibration whose vibration frequency drops to represent the averaged conductivity or a reduced difference in conductivity between the two circuits. Alternately, feedback can be represented as one audio tone representing the differential conductivity between the circuits x and y and/or a haptic vibration whose frequency represents the average of conductivity between the circuits or the difference in conductivity between the two circuits x and y. The audio tone or tones and the haptic vibration will indicate better conductance by providing a lower pitch and/or vibration frequency. This feedback allows the user to audibly or tactilely tell if they are pressing the device adequately against and perpendicular to their skin. This is particularly useful if the injection is around back (a buttocks injection) or if the user is visually impaired or if they have problems orienting their arms with respect to their body. When the skin sense algorithm senses that they have a good position of the device and it is being held steady, the feedback can change the audible feedback to a "ready to inject" signal such as by playing a sound byte or by playing directions in human spoken language, and the haptic vibration can be continued or discontinued, and the (6) "Initiate Button" can then be made active (enabled). If the conductivity becomes inadequate before the patient presses the "Initiate Button", the button can be made inactive again and the positioning audio tone and/or the haptic vibration are returned. If the algorithm senses adequate positioning again and the "Initiate Button" is made active and is pressed by the patient, the injection sequence is begun. If during the sequence, either circuit's conductance drops suddenly or is lost, the needle is withdrawn and the "Actuator" is returned to its initial position, and an audible error feedback signal is presented to the user. At this point, the patient will have to start over by resetting the injector. Human spoken language as played by the speaker can provide constant feedback and directions to the user as well.

53) Tactile Initiate Switch: a "Dome Switch" connected to the (48) "Plastic Flexible Printed Circuit", the dome being positioned under the elastomeric (6) "Initiate Button". The "Initiate Button" when pressed collapses the dome, which then makes contact with the "Plastic Flexible Printed Circuit" completing connection between two parts of a circuit and thereby signaling the (19) "Integrated Circuit Board" that the button has been pressed.

54) Speaker Grill: is an area of the plastic (42) "Access Cover; Motor Section" which has molded-in slots to allow sound from the (55) "Speaker" to pass into the air and be heard by the user.

55) Speaker: an audio speaker used to convey audio feedback tones, sound bytes and human spoken directions or queues to the user in using the injector and responding various states of the injector as detected by the various algorithms running in the software. The speaker is a PUI AS01508MR-R, 1.2 watt, 15 mm speaker or equivalent, with 8 ohm impedance, Mylar cone and Nd—Fe—B magnet.

56) Guide Tube/Syringe Guide Housing: The plastic housing which consists of the (2) "Guide Tube" as part of its distal end and which accommodates the (32) "Syringe Guide" in the upper compartment of its proximal end and which also accommodates the (18) "Battery" and (59) "Haptic Vibrator" in the (58) "Battery & Vibrator Bottom Compartment" of its proximal end.

57) Moving Carriage and Electronics Housing; The plastic housing which accommodates the (9) "Moving Carriage" and the (17) and (21) Motors and the (54) "Speaker" in its upper compartment and which accommodates the (19) "Integrated Circuit Board" in the (33) "Bottom Section".

58) Battery & Vibrator Bottom Compartment: the lower compartment of the (56) Guide Tube/Syringe Guide Housing" which houses the (18) Battery (or Batteries) and optionally, the (59) "Haptic Vibrator".

59) Haptic Motor: a shaftless offset cam motor (such as found in mobile phones) which provides audio and haptic sensory feedback (vibration) to the user. The rotational speed of the motor is reduced when the conductance, as detected by the (52) "Skin Sensor Printed Circuit", increases which indicates higher pressure between the (65) "Skin Sensor Contacts" and the patient's skin and/or a more perpendicular contact of the injector to the skin.

60) Molded-in Conductors: these are electrical conductors molded into the (67) "Needle Guard" which convey electrical information from the (65) "Skin Sensor Contacts" on the (84) "Conductive Pressure Contacts" which are part of the (63) "Pressure Contact Circuit Board". When the (67) "Needle Guard" is attached to the (69) "Syringe Section Housing", the "Molded-in Conductors" (which have bent rounded ends) are pressed against the "Conductive Pressure Contacts" on the (63) "Pressure Contact Circuit Board" which then convey the electrical information to a (76) "Flexible Electric Circuit" via a (104) "Flexible Circuit Connector" made for such connections that is mounted on the "Pressure Contact Circuit Board". The "Flexible Electric Circuit" then conveys the electrical information to the (19) "Integrated Circuit Board".

61) Needle Shield Grooves: two grooves, one on either side (180° apart) of the inside of the (67) "Needle Shield" which keep the (70) "Needle Guide" from rotating because the (62) "Needle Guide Fins" which form part of the (70) "Needle Guide" are captured by and slide in the "Needle Shield Grooves". Thus, the (70) "Needle Guide" can only move forward or backward but not rotate about the needle axis.

62) Needle Guide Fins: two fins which are part of the (70) "Needle Guide". These fins fit into the (61) "Needle Shield Grooves" which keep the (70) "Needle Guide" from rotating inside the (67) "Needle Guard".

63) Pressure Contact Circuit Board: a printed circuit board with conductive contacts so positioned so that the rounded bent ends of the (60) "Molded-In Conductors" of the (67) "Needle Shield" make contact with the (84) "Conductive Pressure Contacts" of the d(63) "Pressure Contact Circuit Board" when the "Needle Shield is attached. These contacts are electrically connected by printed circuit traces to a connector made for flexible plastic circuit termination. Into this connector is inserted the (76) "Flexible Electric Circuit" which is connected to the (19) "Integrated Circuit Board" Thus, the electrical information from the (65) "Skin Sensor Contacts" are conveyed to "Flexible Electric Circuit" and ultimately to the (19) "Integrated Circuit Board".

64) Skin Sensor Contact Support: a supporting surface, which could be plastic or printed circuit board, which supports the (65) "Skin Sensor Contacts" on its surface which make contact with the patient's skin.

65) Skin Sensor Contacts: are electrical contacts which, with the patient's skin, form two electrical circuits which are used to measure conductivity between the contacts. The "Skin Sensor Contacts" are four in number and are arranged at the 12, 3, 6 and 9 O'clock positions. The 12 and 6 O'clock contacts with the skin form one electrical circuit, and the 3 and 9 O'clock contacts with the skin form another electrical circuit. These two circuits sense conductivity in the x and y positions which provide information indicating pressure and angle information between the "Skin Sensor Contacts" and the patient's skin at the injection site, which is used and conveyed to the patient in audio and haptic feedback to assist the patient in holding the injector perpendicular to the skin and to provide information to the injector such that decisions about the "readiness for injection" of the device's location on the skin and it's perpendicularity to the skin can be made by the skin sense algorithm.

66) Needle Guide Spring: a low force spring used to keep the (70) "Needle Guide" toward the proximal end of the (67) "Needle Shield" so that the user can insert a (68) "Luer Fitting Needle" (or other similar removable needle) into the (70) "Needle Guide". The "Needle Guide Spring" also assists in removing the needle from the patient's skin after the injection and in the event that the (68) "Luer Fitting Needle" is a Luer Slip type needle, the spring assists in preventing separation of the needle from the syringe. Said another way, in this type of needle (a luer slip as opposed to a luer lock needle), friction is the only means that keeps the needle attached to the syringe slip connector, so as the syringe is retracted after the injection, should the friction be lower than that required to pull the needle from the skin (thus keeping the needle with the syringe), the "Needle Guide Spring" will push the needle from the skin thus keeping the needle with the syringe as the syringe is withdrawn backward. Much less force is required to remove a needle from tissue as compared to inserting a needle into tissue. Therefore, a relatively low force (and low spring constant) spring is required.

67) Needle Shield: provides a guide tube for the (70) "Needle Guide" to slide forwards and backwards, and also acts as a shield to retain the needle after injection and thus guard against "needle stick". The "Needle Shield" has a flange on the proximal end (the end away from the patient) much like a luer type needle has a flange on its proximal (connector) end. This flange on the "Needle Shield" when connected to the (69) "Syringe Section Housing" is engaged with the (71) "Luer-Like Thread" of the housing. That is, the "Needle Shield" connects to the (69) "Syringe Section Housing" much the same way that a Luer Lock needle engages with the threads of a Luer Lock syringe. This flange on the "Needle Shield" has a (78) "Alignment Notch" which, when oriented to the top of the device, mates with (73) an "Alignment Tab" on the "Syringe Section Housing". This alignment allows the "Needle Guard" to slide into the "Syringe Section Housing" and thus allow the flange to engage with the "Luer-Like Thread". Then, a partial rotation of the "Needle Shield" in the clockwise direction (to the right when facing the distal end of the injector) causes a torque of the "Needle Shield" into the injector and rotated less than a half of a turn, the "Needle Shield" locks into place. That is, it causes the bent ends of the (60) "Molded-In Conductors" to contact the conductive pads on the (63) "Pressure Contact Circuit Board" which generates an opposing force halting the rotation. This results in the (65) "Skin Sensor Contacts" becoming in electrical communication with the (63) "Pressure Contact Circuit Board" via the (60) "Molded-In Contacts" and ultimately, allows the processor to be in electrical communication with the (65) "Skin Sensor Contacts" via the (76) "Flexible Electric Circuit". The "Needle Shield" has two grooves in its inside wall that are 180 degrees apart and these grooves accommodate the (62) "Needle Guide Fins" which are on the (70) "Needle Guide". The "Needle Guide" holds the connector (proximal) end of the Luer type needle and guides the needle down the length of the "Needle Guard" during the injection. Once the injection is complete, the syringe is withdrawn bringing "Needle Guide" and the needle with it and out of the patient. Then, the "Needle Shield" can be rotated counter clockwise (to the left) a partial revolution to release it from the "Luer-Like Thread" of the "Syringe Section Housing". When so rotated, the "Needle Guide" is rotated with the "Needle Shield" due to the engagement between the (61) "Needle Shield Grooves" and the "Needle Guide Fins". The "Needle Guide" holds the Luer type needle which itself has fins and these fins engage with matching indentations on the inside of the "Needle Guide". Therefore, the rotation of the "Needle Shield" Causes the (68) "Luer Type Needle" to be slipped off the syringe or unlocked from the syringe, depending upon if the syringe/needle combination is a Luer Slip or Luer Lock arrangement. Thus, the needle is removed from the syringe and stays inside the "Needle Shield" for disposal in a sharps/bio-hazard container.

68) Luer Slip/Luer Lock Needle: This is a standard needle connection device made for use with standard Luer Slip or Luer Lock syringes (or similar). The "(70) "Needle Guide" has a cavity on its interior that matches the exterior shape of Luer needle connectors, including the four fins present on the needle's connector. These fins which mate with the "Needle Guide" allow the needle to be rotated and slipped off or unlocked from standard Luer type syringes when the "Needle Guide" is rotated, which is rotated when the (67) "Needle Shield" is rotated thus removing the needle from the syringe.

69) Syringe Section Housing: The plastic housing which attaches to the (67) "Needle Shield" via the (71) "Luer-Like Threads" on the distal end and the (49) "Folding Hinge" on its proximal end. The "Syringe Section Housing" accommodates the (75) "Pressure Contact Circuit Board Support" and the (6) "Initiate Button" as well as the (76) "Flexible Electric Circuit" which makes contact to the (63) "Pressure Contact Circuit Board" and the (53) "Tactile Initiate Switch" mounted underneath the "Initiate Button". Also, the "Syringe Section Housing" has a (72) "Battery & Vibrator Bottom Compartment" which accommodates the (18) "Battery", the battery contacts and the (59) "Haptic Vibrator", and the (47) "Battery/Vibrator Cable" (not shown).

70) Needle Guide, a plastic sliding guide which has a molded interior cavity which matches the shape of Luer type Needle connectors or other similar needle connector arrangements. The "Needle Guide" has (62) "Needle Guide Fins" which slide back and fourth in the (61) "Needle Shield Grooves". Because of the engagement between these fins and the grooves, when the (67) "Needle Shield" is rotated, the "Needle Guide" is forced to rotate with it. Likewise, the interior of the "Needle Guide" has a cavity shape which matches the exterior of the (68) Luer Slip/Luer Lock Needles" and so when the "Needle Guide" is rotated by rotation of the "Needle Shield", the "Luer Slip/Luer Lock Needles" are also rotated, thus removing the needle from the syringe. In other words, the Needle Guide removes Luer type needles from syringes much the same way that a Luer type needle is removed from a syringe by the needle shield which originally accompanies the needle from the manufacturer. In this case, the original needle shield is replaced by the "Needle Shield"/"Needle Guide" combination of this injector.

71) Luer-Like Thread: is a spiral thread much the same as a Luer Lock thread of a Luer Lock syringe, only larger. The purpose of the thread is to pull the "Needle Shield's flange into the (69) "Syringe Section Housing" and apply a torque force between the (60) "Molded-In Conductor" ends which are bent into a rounded arc, and the conductive pads on the (63) "Pressure Contact Circuit Board". The (67) "Needle Shield" so tightened into the "Luer-Like Thread" causes electrical information from the (65) "Skin Sensor Contacts" to be conducted to the "Pressure Contact Circuit Board" by the (60) "Molded-In Electrical Conductors". The "Pressure Contact Circuit Board" is connected to the (76) "Flexible Electric Circuit" which is connected to the microcontroller.

The Luer-Like Threads" also provide for quick attachment and removal of the "Needle Shield" from the injector.

72) Battery and Vibrator Compartment: is a lower compartment in the (69) "Syringe Section Housing". The lower compartment houses the (18) "Battery" and optionally the (59) "Haptic Vibrator". The (47) "Battery/Vibrator Cable" (not shown) connects these devices to the (19) "Integrated Circuit Board" by passing through the (49) "Folding Hinge".

73) Alignment Tab: a protrusion from the cylindrical (74) "Exterior of Luer-Like Thread" facing toward the center of the "Needle Shield" and into the clearance space provided by the interior of the (71) "Luer-Like Thread" to just insert the (67) "Needle Shield" flange. The "Alignment Tab" prevents the insertion of the "Needle Shield" except when the (78) "Alignment Notch" of the "Needle Shield" flange is brought into alignment with the "Alignment Tab". By aligning the "Needle Shield" in a specific orientation (by alignment of the notch and tab) before it's rotation and engagement with the "Luer-Like Thread" and subsequent torque upon rotation, the landing spot of the (60) "Molded-In Conductors" can be controlled so that they come into contact with their mating conductive pads of the (63) "Pressure Contact Circuit Board" as the "Needle Shield" reaches a tightened position.

74) Exterior of Luer-Like Thread: is a circular protrusion from the distal end of the (69) "Syringe Section Housing".

75) Pressure Contact Circuit Board Support: is a protrusion from the bottom of the upper compartment of the (69) "Syringe Section Housing" which supports the (63) "Pressure Contact Circuit Board".

76) Flexible Electric Circuit: is a printed circuit of electrically conductive traces on flexible plastic (such as Mylar) which provides connections to the (63) "Pressure Contact Circuit Board" as well as connections to the (53) "Initiate Switch" (located under the (6) "Initiate Button") and to the (34) "Lid Closed Sensor, Syringe Section". The "Flexible Electric Circuit" is shaped in such a fashion that it can lay flat against the inside surface of the upper compartment of the (69) "Syringe Section Housing" and then pass through a slot between the upper and lower compartments into the (72) "Battery/Vibrator Bottom Compartment", and then pass through the (49) "Folding Hinge" and terminate on the (19) "Integrated Circuit Board" located in the (33) "Electronics Bottom Compartment" of the (57) "Moving Carriage and Electronics Housing".

77) Spring Recess: a cylindrical cavity within the distal end of the (70) "Needle Guide" wherein the (66) "Needle Guide Spring" is compressed when the "Needle Guide" is pressed forward toward the distal end of the (67) "Needle Shield".

78) Alignment Notch: a cut-out in the (67) "Needle Shield" flange which allows the "Needle shield" to be inserted into the (72) "Luer-Like Thread" when it is aligned with the (73) "Alignment Tab" at the top of the (69) "Syringe Section Housing". Once the "Needle Shield" is aligned and inserted into the "luer-Like Thread", it is rotated clockwise (or "to the right" when facing the distal end of the injector) which engages the "Needle Shield" flange with the "Luer-Like Thread" and affixes the "Needle Shield" in place. By aligning the "Needle Shield" in a specific orientation (by alignment of the notch and tab) before it's rotation and engagement with the "Luer-Like Thread" and subsequent torque upon rotation, the landing spot of the (60) "Molded-In Conductors" can be controlled so that they come into contact with their mating conductive pads of the (63) "Pressure Contact Circuit Board" as the "Needle Shield" reaches a tightened position.

79) Stiffener: Part of (75) "Pressure Contact Circuit Board Support" which is part of the plastic housing which extends up from the bottom of the upper compartment of the (69) "Syringe Section Housing".

80) Vein Indentations: are grooves or recesses on the inside of the (70) "Needle Guide" which catch or accommodate the fins on the (68) "Luer Slip/Luer Lock Needle". This provides an engagement between the "Needle Guide" and the "Luer Slip/Luer Lock Needle" so that when the "Needle Guide" is rotated, it causes the needle to be rotated, thus, disengaging the Luer type needle from the syringe.

81) Needle Opening: is a hole through the distal end of the (70) "Needle Guide" which allows the Luer type needle to be inserted and pass through the "Needle Guide" into the interior of the (67) "Needle Shield".

82) Snap Dome Sensor: is a digital "button pressed" sensor which consists of two neighboring traces on the (76) "Flexible Electric Circuit" which extends up to the (6) "Initiate Button" on the (56) "Guide Tube/Syringe Guide Housing" and is effected by a (53) "Snap Dome" on the inside of the "Initiate Button" which, when pressed, causes the "Snap Dome" to collapse and complete an electric circuit between the two conductive traces on the "Flexible Electric Circuit". The state of the "Initiate Button" is detected by the microcontroller which detects the closure of the electric trace circuit by a digital input.

83) Conductive Spring: a small spring mounted in a recess of the (36) "Access Cover, Syringe Section" or of the (40) "Access Cover, Carriage Section". The spring protrudes a tiny bit so that when the "Access Cover" is closed, the spring bridges two conductive pads in the (48) or (76) "Flexible Electric Circuit" or a separate dedicated flexible circuit for the carriage section (not shown) and thus completing the circuit and signaling the (19) "Integrated Circuit Board" which monitors the state of the circuits with digital inputs that the access covers are closed.

84) Conductive Pressure Contacts: are conductive metal pads on the (63) "Pressure Contact Circuit Board" which come into contact with the (60) "Molded-In Conductors" when the (67) "Needle Shield" is attached. The "Conductive Pressure Contacts" are electrically connected to the (104) "Flexible Circuit Connector" by conductive traces of the "Pressure Contact Circuit Board".

85) Operator Display: a 128×32 dot matrix OLED (Organic Light Emitting Diode) display. The display is mounted within the (40) "Access cover" and its ribbon cable exits toward the hinge of the access cover and travels within a recess of the wall of the (57) "Moving Carriage and Electronics Housing" to make connection with the (19) "Integrated Circuit Board" by a connector made for such ribbon cables. The display will primarily be displaying two lines of text for menu choosing and displaying automated graphics while the device is in operation. During menu operations, the top line of text displays the name of the current menu. The second line of text displays the current choice in that menu. Pressing the (87) "Scroll Left" button on the (86) "Operator Key Pad" causes the second line of choices to shift to the left off screen while shifting in from the right, the next choice. Likewise, pressing the (88) "Scroll Right" causes the second line of choices to shift to the right and off screen while shifting in from the left, the next choice. Pressing the (90) "Enter" button accepts the current choice displayed in the bottom line of text. Pressing the (89) "Return" button causes the display to go up one level in the menu arrangement. When the autoinjector is unfolded and latched into place, pressing any button causes the device to wake up from sleep mode. The display is an OSD12832P0906-10 by OSD Displays or an OEL9M064-Y-E by Truly Semiconductors. Both are 128×32 pixel OLED displays with integrated SSD1305 driver by Solomon Systech featuring an SPI interface.

86) Operator Key Pad: an arrangement of four membrane switches for making menu selections. The "Operator Key Pad" works in conjunction with the (85) "Operator Display. The membrane keypad works by pressure from the user's fingers, primarily their thumbs, which cause two parts of an electric circuit to make electrical connection which then provides a voltage to a digital input on the (19) "Integrated Circuit Board". The "Operator Key Pad" is mounted in an indentation of the outside wall of the (57) "Moving Carriage and Electronics Housing" and faces the user when they are holding the autoinjector horizontal in front of them with the needle end to their left. The "Operator Key Pad" makes connection to the (19) "Integrated Circuit Board" by a ribbon cable which exits the "Operator Key Pad" and travels to the "Integrated Circuit Board" through a recess in the wall of the "Moving Carriage and Electronics Housing" where it makes connection to the "Integrated Circuit Board" by a connector made for such ribbon cables. During menu operations, the top line of text shown in the (85) "Operator Display" is the name of the current menu. The second line of text displays the current choice in that menu. Pressing the (87) "Scroll Left" button on the (86) "Operator Key Pad" causes the second line of choices to shift to the left off screen while shifting in from the right, the next choice. Likewise, pressing the (88) "Scroll Right" causes the second line of choices to shift to the right and off screen while shifting in from the left, the next choice. Pressing the (90) "Enter" button accepts the current choice displayed in the bottom line of text. Pressing the (89) "Return" button causes the display to go up one level in the menu arrangement. When the autoinjector is unfolded and latched into place, pressing any button causes the device to wake up from sleep mode.

87) Scroll Left Button: causes the second line of text in the (85) "Operator Display" to move off screen to the left and the next choice for the current menu, to move on screen from the right. The choices for any particular menu are arranged as a loop so that successive presses of the scroll buttons will eventually begin repeating the choices for the particular menu.

88) Scroll Right Button: causes the bottom line in the (85) "Operator Display" to move off screen to the right and the next choice for the current menu, to move on screen from the left. The choices for any particular menu are arranged as a loop so that successive presses of the scroll buttons will eventually begin repeating the choices for the particular menu.

89) Return Button: causes the (85) "Operator Display" to exit the present menu and return to the previous menu. If the user is already at the root or "home" menu, there is no action but to redisplay the current menu.

90) Enter Button: causes the display to move the current bottom line of the display up to the top line therefore becoming the new current menu, and causes the control algorithm of the injector to act on that choice. The second line of text then displays the choices of the new current menu displayed in the top line of text.

91) Syringe Barrel: the cylindrical portion of a syringe which contains the medicament.

92) Syringe Finger Flange: also known as the "finger flanges". The "Syringe Flange" are two flat protrusions arising from the "Syringe Barrel" and flat to the axis of the syringe. The "Syringe Flange" is normally (when a manual injection is given) used to apply an opposing force to the force of the (14) "Syringe Plunger Rod" by placing the tips of the index finger and second finger underneath the "Syringe Flange" so opposing the thumb which rests on the (11) "Plunger Thumb Pad". In this autoinjector design, the "Syringe Flange" is only used for pushing the needle into the patient's tissue by way of the (10) "Elastomeric Flange Grip" which holds the "Syringe Flange" as well as the "Syringe Barrel".

93) Elastomeric Barrel Grip: the portion of the (10) "Elastomeric Flange Grip" which actually grips the (91) "Syringe Barrel". The "Elastomeric Flange Grip" restricts the (92) "Syringe Flange" in only the axial dimension of the syringe, while the "Elastomeric Barrel Grip" actually grips the barrel from moving side-to-side and up-and-down. Thus, by way of the "Elastomeric Barrel Grip", the "Syringe Flange" is restricted in three dimensions. The "Elastomeric Barrel Grip" holds the barrel firmly in x and y dimensions, both perpendicular to the syringe axis, while the "Elastomeric Flange Grip" holds the flange in the axial direction of the syringe. The (10) "Elastomeric Flange Grip" and the "Elastomeric Barrel Grip" are both parts of the same piece of elastomer. The two separate terms further delineates the two functions of the elastomer which sum to provide restriction of the "Syringe Flange" in three dimensions.

94) Elastomeric Recess: the cavity portion of the (10) "Elastomeric Flange Grip" shape which provides space in which to press the (92) "Syringe Flange" when inserting a syringe into the autoinjector. The non-Recess" portion of the elastomer juts out to grip the (91) "Syringe Barrel". This same portion that "juts out", is the portion of the elastomer which prevents axial movement of the "Syringe Flange" which is resting in the "Elastomeric Recess" or cavity of the elastomer so shaped to accommodate the "Syringe Flange".

95) Writing Surface: a white board or pencil board writing surface. Can be used to mark the drug loaded, the patient number or other such useful information.

96) Not used

97) Not used

98) Not used

99) Not used

100) Flexible Circuit Serpentine: the section of the (76) "Flexible Circuit" which serpentines through the (49) "Folding Hinge".

101) Flexible Circuit Extension: the section of the (48) "Flexible Circuit" which travels through the (2) "Wire Way" and terminates as the (52) "Skin Sensor Printed Circuit".

102) Slit: is a thin opening between the upper and lower compartments of either the (56) "Guide Tube/Syringe Guide Housing" or the (69) "Syringe Section Housing" (depending upon the version or embodiment of the invention). The "Slit" allows passage of the (48) "Flexible Electric Circuit" or the (76) "Flexible Electric Circuit" (depending upon the version or embodiment of the invention) from the upper compartment into the lower compartment where it then passes through the (49) "Folding Hinge" and then terminates into the (103) "Flexible Circuit Connector" mounted on the (19) "Integrated Circuit Board".

103) Flexible Circuit Connector: is a connector made for terminating flexible circuits onto a printed circuit board. In this case, the "Flexible Circuit Connector" is mounted on the (19) "Integrated Circuit Board" and provides electrical connections from conductors on the (48) "Flexible Electric Circuit" or the (76) "Flexible Electric Circuit" (depending upon the version or embodiment of the invention) to conductors located on the "Integrated Circuit Board".

104) Flexible Circuit Connector: is a connector made for terminating flexible circuits onto a printed circuit board. In this case, the "Flexible Circuit Connector" is mounted to the (63) "Pressure Contact Circuit Board" and provides electrical connections from conductors on the (76) "Flexible Electric Circuit" to conductive traces on the "Pressure Contact Circuit Board" and ultimately to the (84) "Conductive Pressure Contacts".

105) Molded-In Conductor Bridge: is an electrical connection between two extra (60) "Molded-In Conductors" in the attachable/removable (67) "Needle Shield" (they are "extra" only in that these specific "Molded-In Conductors" do not terminate onto any of the four (65) Skin Sensor Contacts"). When the "Needle Shield" is attached, two extra (84) "Conductive Pressure Contacts" (which match up with the extra Molded-In conductors) detect the electrical connection provided by the "Molded-In Conductor Bridge" because the "bridge" completes the circuit. The (76) "Flexible Electric Circuit" also has two extra traces to convey this electrical connection information to the (19) "Integrated Circuit Board". The "Integrated Circuit Board" then interprets the conductivity between these two traces as indication that the "Needle Shield" is attached. This information is then used in algorithms which allow or prohibit operation of the injector.

106) Conductive Spring: a small spring mounted in a recess of the (57) "Moving Carriage and Electronics Housing". The spring protrudes a tiny bit so that when the autoinjector is unfolded and locked into position, the spring bridges two conductive pads in the (48) or (76) "Flexible Electric Circuit" or a separate dedicated flexible circuit for the carriage section (not shown) thus completing the circuit and signaling the (19) "Integrated Circuit Board" which monitors the state of the circuits with digital inputs that the injector is unfolded and latched.

107) Unfolded and Latched Sensor: is a digital "contact closed" sensor which consists of two neighboring traces on the (48) or (76) "Flexible Electric Circuit" which extends over to the opening of the (56) "Guide Tube/Syringe Guide Housing" or (69) "Syringe Section Housing" just above the (49) "Folding Hinge" and is effected by a (106) "Conductive Spring" which is supported on the inside of the (57)) "Moving Carriage and Electronics Housing" just above the "Folding Hinge". When the injector is unfolded and latched into place by the two (39) "Thumb Buttons" snapping into their detent positions, the "Conductive Spring" completes an electric circuit between the two conductive traces on the "Flexible Electric Circuit". The state of the contact is monitored by the microcontroller which detects the closure of the electric trace circuit by a digital input thus indicating that the injector is in the unfolded and operational position.

108) Luer Opening: is a hole through the proximal end of the (70) "Needle Guide" which allows the Luer type needle to be inserted and pass through the "Needle Guide" and for the Luer connector's "veins" to snug into the (80) "Vein Indentations of the "Needle Guide". That is, the interior of the "Needle Guide" contains (80) "Vein Indentations" which allow the veins present on the Luer needle connector to slide into said indentations and "snug". This engagement between the "Needle Guide's" "Vein Indentations" and the fins on the needle's Luer connector is what forces the Luer needle to be twisted off the syringe when the (67) "Needle Shield" and hence, the (70) "Needle Guard" are twisted to the left.

109) Not used:

110) Membrane Keypad Overlay: is an elastomeric overlay to the (86) "Operator Keypad". The "Membrane Keypad Overlay" contains graphic outlines where the conductive pressure keys are located plus raised embossing for the outline of the key as well as the symbols which indicate the button (key) function of scroll right and left, return, and enter.

111) Scroll Right Symbol: is a button shape with a right pointing arrow shape embossed into the (110) "Membrane Keypad Overlay". The symbol and the underlying electrical circuit constitutes the (88) "Scroll Right Button" of the (86) "Operator Key Pad".

112) Scroll Left Symbol: is a button shape with a left pointing arrow shape embossed into the (110) "Membrane Keypad Overlay". The symbol and the underlying electrical circuit constitutes the (87) "Scroll Left Button" of the (86) "Operator Key Pad".

13) Membrane Keypad Substrates: layers of plastic onto which are printed the electrical traces of the circuits and the dividing layer between the circuits.

114) Membrane Keypad Ribbon Cable: is an extension of the (113) "Membrane Keypad Substrates" which form a flexible circuit that extends down into the (33) "Electronics Bottom Compartment" of the (57) "Moving Carriage and Electronics Housing" to terminate onto the (19) "Integrated Circuit Board" by a (115) "Membrane Keypad Connector" mounted on the "Integrated Circuit Board". The circuits are monitored by digital inputs of the (125) "Microcontroller".

115) Ribbon Cable Connector: a flexible electric circuit connector mounted on the (19) "Integrated Circuit Board" which connects to the (114) "Membrane Keypad Ribbon Cable.

116) 3.3 volt traces: are electrically conductive traces on one of the (113) "Membrane Keypad Substrates" which supply voltage to the (117) "Key Traces" when the area of the buttons are pressed down. The "3.3 volt traces" normally have a space between them and the "Key Traces" and only when pressed down, does the "3.3 volt trace" circuit make electrical connection with the "Key Traces", thus signaling that a button of the (110) Membrane Keypad Overlay" has been pressed.

117) Key Traces: are electrical conductive traces on one of the (113) "Membrane Keypad Substrates", one circuit per button of the (1104) "Membrane Keypad Overlay". When one of the buttons are pressed, the "Key Trace" associated with that button makes electrical contact with the "3.3 volt traces" and thus, the "Key Trace" goes to 3.3 volts. This voltage is conveyed by the (114) "Membrane Keypad Ribbon Cable" to the (19) "Integrated Circuit Board" where it is detected by one of the (125) "Microcontroller" digital inputs.

118) Interim Substrate Cutout: is a hole in the substrate which separates the (116) "3.3 volt traces" from the (118) "Key Traces". The hole allows the two circuits to electrically contact each other when a button of the (110) "Membrane Keypad Overlay" is pressed.

119) Return Symbol: is a button shape with an upward pointing arrow shape embossed into the (110) "Membrane Keypad Overlay". The symbol and the underlying electrical circuit constitutes the (89) "Return Button" of the (86) "Operator Key Pad".

120) Enter Symbol: is a button shape with a check mark shape embossed into the (110) "Membrane Keypad Overlay". The symbol and the underlying electrical circuit constitutes the (90) "Enter Button" of the (86) "Operator Key Pad".

121) 3.3 Volt Regulator: is an ultra low drop out, low noise voltage regulator. This is an ST LDS3985xx33 or equivalent. It provides ultra low drop out BiCMOS 3.3 volts of regulation for use with very low ESR output capacitor. The regulator provides up to 300 mA. It is stable with ceramic and high quality tantalum capacitors. The ultra low drop voltage, low quiescent current and low noise makes it suitable for low power applications in battery powered systems.

122) 3.0 Volt Regulator: is an ultra low drop out, low noise voltage regulator. This is an ST LDS3985xx30 or equivalent. It provides ultra low drop out BiCMOS 3.0 volts of regulation for use with very low ESR output capacitor. The regulator provides up to 300 mA. It is stable with ceramic and high quality tantalum capacitors. The ultra low drop voltage, low quiescent current and low noise makes it suitable for low power applications in battery powered systems.

123) Battery Charger: This is a Microchip MCP73861-Advanced Single, Fully Integrated Li-Ion, Li-Polymer Charge Management Controller or equivalent. The MCP7386X family of devices features highly advanced linear charge management controllers for use in space-limited, cost-sensitive applications. The devices combine high-accuracy, constant voltage and current regulation, cell preconditioning, cell temperature monitoring, advanced safety timers, automatic charge termination, internal current sensing, reverse blocking protection, charge status and fault indication. The MCP7386X provides a complete, fully functional, stand-alone charge management solution with a minimum number of external components. The MCP73861 is intended for applications utilizing single-cell Lithium-Ion or Lithium-Polymer battery packs.

124) USB to SPI Protocol Converter: This is a Microchip MCP2210 USB to SPI protocol converter or equivalent part. The MCP2210 device is a USB-to-SPI Master converter which enables USB connectivity to the SPI serial port. USB termination resistors are provided within. The MCP2210 also has 256 bytes of integrated user EEPROM and has nine general purpose input/output pins. Seven pins have alternate functions to indicate USB and communication status. Two of these pins are utilized to interface with the (123) "Battery Charger" to enable the charger and to the set the charge current depending upon the source.

125) MCU (Micro Control Unit): A highly integrated microcontroller. This is a Microchip dsPIC33FJ128GP804 digital signal processor. The dsPIC33FJ model is a 16 bit microcontroller with a built in digital signal processor (for processing the audio features of the autoinjector) and operation up to 40 MIPS. The DSC CPU has a 16 bit data path and 24 bit instructions and two 40-bit accumulators. On-chip are 16 k of RAM and 128 k of flash program memory, eight DMA channels, real-time clock/calendar, output PWM generation, flexible digital IO (DI and DO), wake-up on pin change-of-state, Analog-to-Digital Converters (ADC), Digital-to-Analog Converters (DAC), two SPI serial ports and one I2C serial port, all of which are utilized in implementing the functions and algorithms of this autoinjector.

126) External Flash Memory with SPI port: Serial access memory for audio and real time calendar storage. This is an SST (Silicone Storage Technology) SST25VF080B-80-4I-QAE-8 Mbit Flash with SPI serial interface or equivalent. It writes (Program or Erase) with a single power supply of 2.7-3.6V. The memory array is organized in uniform 4 Kbyte erasable sectors with 32 Kbyte overlay blocks and 64 Kbyte overlay erasable blocks.

127) Photointerrupter: A double-layer molding Photointerrupter with integral photo emitter (infrared LED) and photo transistor. This is a Rohm RPI-0226 or equivalent, which uses a single chip molded technology in place of the conventional casing method. This allows for an ultra-small package. A slit in the package allows an outside "interrupter" (the (45) "Position Fin") to block light from reaching the phototransistor from the photo emitter.

128) Power MOSFET: This is a Fairchild 2N7002 N-Channel or equivalent enhancement mode field effect transistor designed to minimize on-state resistance while providing switching up to 400 mA. Gate threshold is at logic level, and the device is particularly suited as a power MOSFET for small motor control.

129) 3.3 Volt Reference: An LDO active reference for the analog to digital converter section of the MCU. This is a National Semiconductor (now TI) LM4132 Precision Low Dropout voltage reference or equivalent. This device performs comparable to the best laser-trimmed bipolar references due to the use of EEPROM registers for correction of curvature, tempco, and accuracy on a CMOS bandgap architecture that allows package level programming to overcome assembly shift. The LM4132 is a reference that is capable of delivering up to 20 mA of current, and therefore, is usable of supplying the current requirement of the AVdd pin specification, yet it is a precision reference as opposed to a "regulator".

130) Dual H-Bridge FET Driver: a dual DC motor H-Bridge motor driver (two separate motor drivers). This is a Toshiba TB6590FTG monolithic dual DC motor driver IC or equivalent. The TB6590TG utilizes LDMOS output transistors with low ON-resistance and operation down to 2.2 v. This may be desirable since the 3.0 volt motors (17) and (21) may need to be operated below design to affect a steeper torque/current ratio. The TB6590FTG provides four operation modes selectable via IN1 and IN2: Forward, Reverse, Short Brake, and Stop. These modes are affected by PWM inputs applied by the MCU. The IC also provides a Standby pin which will be asserted whenever the motors aren't required, thus saving significant power for a hand-held battery powered device.

131) Op Amp: an operational amplifier: This is a Linear Technology LT6004 or equivalent. The LT6004 is a dual op amp designed to operate at low voltage, and maximize battery life and performance for portable applications. It provides rail-to-rail operation. It draws only 1 µA maximum quiescent current. It has an input offset voltage of 500 µV maximum with a typical drift of only 2 µV/° C., input bias current of 90 pA maximum, open loop gain of 100 k and the ability to drive 500 pF capacitive loads.

132) Multiplexer: a Triple SPDT Analog Switch Multiplexer. This is an ON Semiconductor NLAS4053 analog switch multiplexer or equivalent. The NLAS4053 provides low ON-resistance SPDT (Single Pole Double Throw) "Brake-before-Make" switch. In this instance, the SPDT switches switch two of the PWM outputs of the MCU between two H-Bridge circuits of the (130) "Dual H-Bridge FET Driver. The third SPDT switch (138) is used to switch the CS signal from the MCU going to either the FLASH or display, which both use the same MCU SPI port.

133) Multiplexer: a Dual SPDT Analog Switch Multiplexer. This is an ON Semiconductor NLAS3158 analog switch multiplexer or equivalent. The NLAS3158 provides low ON-resistance SPDT (Single Pole Double Throw) "Brake-before-Make" switches. In this instance, the SPDT switches switch the 0.1 microamp current source and return between two sets of conductive pads on the Skin Contact Conductance Sensor. The skin, in contact with the conductive pads, forms a circuit for the current source with a measured "conductance" as determined by the ADC channel on the MCU.

In the case that the optional TENS generator signal is multiplexed onto the conductive pads, the 133) Multiplexer has to be changed to one with higher operating voltages. This can be provided by a Maxim MAX1457 Quad SPST+ 70V analog switches which provide a low on-resistance of 10 ohms max. This switch provides 2.5 nA (max) Off-Leakage currents and 500 uA (typ) supply current.

134) DC/DC Converter: a DC step-up (boost) converter. This is a Linear Technology LT3580 PWM DC/DC converter containing an internal switch. In this circuit, the LT3580 is configured as a boost, capable of generating 12.5 v from the 3.3 v regulator to supply 12.5 v to the Vcc pin of the (85) "Operator Display".

135) IC) Expander with I2C: a 16-bit I/O expander with an I2C serial interface. This is a Microchip MCP23017 or equivalent. Along with the (136) and (142) "Digital Potentiometers" it shares the MCU's I2C buss. The IO expander provides two ports of eight pins which can be configurable as active-high, active-low or open-drain. Each port has a separate interrupt to the MCU, however, they will be internally OR'ed in this application. The pins can, when configured as inputs, provide an interrupt on change from configured register defaults or on pin change of state. This is utilized for the inputs from contact switches such as the "Lid Closed" sensors.

136) Digital Potentiometer: a digital POT (Potentiometer) with non-volatile Memory and I2C serial port. This is a Microchip MCP4642 Dual Rheostat or equivalent with I2C port. It provides a digital potentiometer functionality by combining internal resistors to produce a total resistance between terminals. It is used in this application to vary the gain (volume) of the (137) "Audio Amplifier" without providing a traditional potentiometer and the associated costs and considerations of providing user access to its setting. In this case, the volume of the audio amplifier can be controlled by the user through the menu/display system.

137) Monaural Audio Amplifier: audio amplifier to power (55) "Speaker". This is an ST TS4962 filter-free mono class D audio power amplifier or equivalent. This power amplifier provides a standby mode so it is not using power except when needed. The unit will output 1.7 W into an 8 ohm speaker with 10% THD+N maximum. That is quite sufficient to hear human speech clearly when the autoinjector is behind you giving a buttock injection and you are partially hard-of-hearing. The volume (gain) is adjusted via the external (136) "Digital Potentiometer". Typical signal to noise ratio is 5 dB.

138) Multiplexer: a Triple SPDT Analog Switch Multiplexer ($\frac{1}{3}^{rd}$ of (132)). This is an ON Semiconductor NLAS4053 analog switch multiplexer or equivalent. The NLAS4053 provides low ON-resistance SPDT (Single Pole Double Throw) "Brake-before-Make" switches. In this instance, the SPDT switch is used to switch the CS signal from the MCU going to either the FLASH or display, which both use the same MCU SPI port. The other two SPDT switches are used for the two of the PWM outputs of the MCU between two H-Bridge circuits of the (130) "Dual H-Bridge FET Driver. The third SPDT switch (138)

139) Shunt Resistor: a precision shunt resistor for current measurement. This is a Vishay WSL0603R1000DEA or equivalent, metal resistor of 0.1 ohm and 0.5% tolerance. The resistor is in the current path of the (17) "Carriage Motor" and the (21) "Actuator Motor" (only one motor runs at a time). The voltage drop across this resistor is sensed by the ADC port of the MCU and converted into a representation of the current of the motor (that's running.)

140) Common mode filter with ESD protection for USB 2.0. This is an ST ECMF02-2AMX6 or equivalent. The part features large differential bandwidth>6 GHz and High common mode attenuation of −34 dB at 900 MHz. It is designed to suppress EMI/RFI common mode noise on high speed differential serial busses like USB 2.0

141) Multiplexer. In the case that the optional TENS generator signal is multiplexed onto the conductive pads, the high voltage from the TENS needs to be multiplexed onto the (133) Multiplexer. This can be provided by a Maxim MAX1457 Quad SPST+70V analog switches. These provide a low on-resistance of 10 ohms max. This switch provides 2.5 nA (max) Off-Leakage currents and 500 uA (typ) supply current. The (133) part also needs to be a high voltage multiplexer, and therefore, both the (141) and the (133) should be of the Maxim MAX1457 type device 142) Digital Potentiometer: a digital POT (Potentiometer) with non-volatile Memory and I2C serial port. This is a Microchip MCP4642 Dual Rheostat or equivalent with I2C port. It provides a digital potentiometer functionality by combining internal resistors to produce a total resistance between terminals. It is used in this application to vary the intensity of the . . . .

143) 32.768 kHz Quartz Watch Crystal This low frequency source provides slow MCU clock cycles during sleep mode. Sleep mode is used primarily to keep the real-time clock-calendar alive as it stores and operates to sound injection reminder alarms according to the patient's schedule.

144) Digital Potentiometer: a digital POT (Potentiometer) with non-volatile Memory and I2C serial port. This is a Microchip MCP4542 Single Rheostat or equivalent with I2C port. It provides a digital potentiometer functionality by combining internal resistors to produce a total resistance between terminals. It is used in this application to vary the intensity of the (145) "PWM TENS Generator" without providing a traditional potentiometer and the associated costs and considerations of providing user access to its setting. In this case, the intensity of the TENS current can be controlled by the user through the menu/display system from 5 to 20 mA.

145) PWM TENS Generator: a PWM LED driver adapted for TENS generation. This is a Linear Technology LTC3783 PWM LED Driver and boost controller or equivalent. The digital potentiometer (144) controls the current limited through the low side power MOSFET (see SECTION EE) and the PWM signal from pin OC4 of the MCU 125 controls the pulse width and frequency.

What is claimed is:

1. A hand-held medical-syringe manipulating device comprising mechanical, electromechanical electronic and software components arranged to provide a housing with an interior cavity which receives either standard or typical needle and syringe combinations that are filled with a medicament such that, when said needle and syringe are inserted into the interior cavity, the device automatically inserts the needle into a patient, dispensing the medicament into the patient, and removing the needle from the patient, wherein the interior cavity so arranged that the needle and syringe are loaded in a horizontal fashion and a lid which closes over the interior cavity hiding the needle and syringe from the patient's view;

electrical sensing and measuring electronics and software capable of analyzing an electrical interface to the patient's skin and translating these characteristics into qualities including contact force and angle;

electronics and conductors for inducing electric currents into the patient's skin to distract the patient from the sensation of needle stick and to reduce the pain of needle insertion;

electronics and software for the execution of programs to effect tactile, auditory, and visual biofeedback cues and instructions to the operator of the device to provide minimal discomfort or fear in the patient during the use of the device;

electronics and software for the execution of programs to control electromechanical components to insert the needle into the patient, inject the medicament contained within the syringe into the patient, and remove the needle from the patient without the patient having sight of the needle or syringe.

2. The medical device according to claim 1 containing electrically conductive pads located on the face of the device which contact the patient's skin when the device is so pressed against the patient; the pads so arranged as sets of two pads each and so arranged that each set is rotated with respect to the other sets as to resemble an X having two sets of pads at 90° to each other, wherein electronic circuits are connected to the sets of conductive pads and said electronic circuits measures electrical characteristics between any two sets of conductive pads, including conductance or capacitance, and further, the electrical characteristics between the sets of pads and the skin is selected as input variables to an algorithm which compares these characteristics from one set of pads to the other sets of pads and can compare these characteristics over the time domain, and said electrical characteristics between the pads and the skin are used to infer the pressure at which the surface containing the pads is being held against the skin and the steadiness with which the surface is being held against the skin, and via algorithm analyzing these characteristics, to infer the angle at which the surface is being held against the skin.

3. The medical device according to claim 2 wherein the electrical conductive pads are multiplexed to separate electronic circuits so that the pads can be used to accomplish both the sensing functions and deliver Transcutaneous Electrical Nerve Stimulation prior to and during the use of the device to produce a reduction in the perceived pain that can result from the action of the device, and wherein the electrical stimulation is controlled as to pulse rate, pulse width, and intensity of pulse in order to produce stimulation of sensory nerve fibers.

4. The medical device according to claim 1 wherein the lid conveys lid closure information to the electronic control system.

5. The medical device according to claim 4 wherein the interior of the housing contains mechanical and electromechanical components comprising a moving carriage assembly which: grips the proximal end of the syringe and its finger flange by an elastomeric insert so shaped to accommodate the syringe dimensions being used or a range of syringe dimensions: the elastomeric insert spreading forces on the syringe thus reducing stresses on the syringe thereby inducing movement of the syringe for the purpose of moving the syringe forwards and rearwards to insert a needle attached to the distal end of the syringe into a patient; and wherein the needle attached to the syringe is completely retained within the housing when the carriage is at its far proximal position which is the position when the device is ready to receive the needle and syringe into its cavity prior to injection; the moving carriage further containing an integral actuator which depresses a syringe plunger to expel the medicament from the syringe through the needle into the patient, and as the carriage moves, the syringe and attached needle and the syringe plunger actuator move as one, while the carriage and the plunger actuator are each movably powered independently so that the needle can be inserted into the patient by moving the carriage, with the medicament dispelled from the syringe into the patient by movement of the plunger actuator, and the needle removed from the patient and retracted into the housing by reversing the moving carriage to its rearward proximal initial position.

6. The medical device according to claim 5 wherein the carriage and the actuator are moved by electric motors attached to lead screws.

7. The medical device according to claim 6 wherein the velocity and acceleration of the motors and their connected loads are calculated from the current flowing through the motor which is measured by the electronics and further, the current is also used to derive the torque being generated by the motors, which is used in the algorithm to regulate speed and to detect when the plunger has reached its end-of-travel and therefore has dispensed all of the medicament.

8. The medical device according to claim 7 wherein the needle and distal end of the syringe is supported and guided within a guide tube forming part of the distal end of the device's housing by a removable fixture shaped to accommodate the dimensions of the needle and syringe being used; and further, the syringe guide is removably attached to the moving carriage by the insert of a flange on the guide's proximal end into a slot in the moving carriage, and wherein the guide moves with the moving carriage and the distal end of the syringe guide holds the distal end of the syringe and attached needle in the guide tube so that the needle emerges from a hole in the center of the distal face of the tube, the tube face being at the distal end of the housing, and wherein the needle exits the housing and enters into the patient's tissue when the carriage is moved forward, and removed from the patient when the carriage is moved rearward, the needle being completely retained within the housing when not being extended and wherein the guide is a separate removable fixture, is molded to accommodate a Luer fitting.

9. The medical device according to claim 7 wherein the distal end of a Luer type syringe and more specifically, a Luer connector molded to the base of the needle which is attached to the Luer syringe by a Luer connector, is supported and guided by a needle guide which has an interior cavity specifically designed to grip by press fitting a ribbed connector end of a Luer needle into the needle guide, so that, as the syringe is moved axially, the needle guide slides within a disposable needle shield forward and back when the moving carriage which holds the proximal end of the syringe moves forwards and back such that the force exerted by the moving carriage onto the syringe's proximal end and finger flange is transmitted directly through the syringe body to the attached needle's Luer connector, thus causing the needle which is fitted into the needle guide to move the needle guide forward and backward within the disposable needle shield as the carriage moves; the syringe body and Luer needle combination forming a solid linkage between the moving carriage and the needle guide, and as such movement occurs, the needle emerges from the center of the distal face of a needle shield, the shield being located at the far distal end of the housing and of such length as sufficient to enclose the longest needle provided for in the design of the device, and wherein the needle exits the housing through a hole and enters into the patient's tissue when the carriage is so moved forward, and removed from the patient when the carriage is moved rearward, the needle being completely retained within the needle shield when not being extended so as to prevent accidental needle stick.

10. The medical device according to claim 9 wherein the needle guide is longitudinally keyed to the inside of the needle shield such that it can slide forwards and back within the needle shield, wherein a longitudinal key causes the needle guide to rotate if the needle shield is rotated; the needle shield being attached to the housing by a Luer twist cam which can be rotated to effect detachment of the needle shield from the housing, and wherein the needle guide is captive within the needle shield is thus removed with the needle shield as it is detached, and wherein the Luer connector, being ribbed and pressed into the form fitting interior of the needle guide when the syringe-needle combination is initially inserted into the interior cavity of the device, is thus rotated as the needle shield is rotated as it is removed from the housing, and wherein the needle shield thus removes the Luer needle from the syringe when the needle shield is removed; and further, the needle guide is biased by a spring to the proximal end of the needle shield so that as the needle is removed from the syringe, the needle guide and thus the needle's connector retains the needle within the needle shield, the shield being of such a length that when the needle guide is biased at the proximal end of the needle shield, the needle is completely retained within the interior of the needle shield.

11. The medical device according to claim 2 wherein biofeedback is provided to the patient indicating the firmness and steadiness with which the distal surface of the device is being held against the patient's skin, and further, biofeedback is provided as to the perpendicularity of the contained needle and syringe to the patient's skin since their perpendicularity is in direct proportion to the flatness of the distal surface is to the patient's skin; the biofeedback being provided by a varying vibrational frequency such as provided by a haptic motor or by a varying tone produced by an audio speaker, or both.

12. The medical device according to claim 11 wherein audio cues consisting of sound bites are provided to inform the user when the combination of: the distal surface of the medical device is being held firmly, held steadily, and held flat against the skin occurs; and further comprising an initiate injection button so as to be available to either hand and pressed by the little finger or the index finger or the thumb, is enabled for its purpose only when the combination of these requirements have been determined by the internal software which then provides the sound bite biofeedback and enables the injection button for initiation of injection having discerned that the patient or administrator of the injection has oriented the device appropriate to initiate the injection of the medicament into the patient, wherein the user can then initiate an injection by pressing the initiate button during which the haptic feedback can be continued and the audio can be changed to either a musical theme in sound bite or human spoken language instructing the patient.

13. The medical device according to claim 1 wherein instructions or directions for using the device or steps as the device is being used, and instructions that it is time for a scheduled injection and instructions to the user in how to handle exceptions or errors in usage, and instructions for the proper disposal of bio-hazardous materials can be provided to the user in any prerecorded human spoken language in addition or in absence of visual indication such as provided by a text or graphic display.

14. The medical device according to claim 13 wherein injection reminder alarms consisting of ringtones or human spoken language are played to the user according to a patient or care-giver established schedule which is stored in an internal real-time lock calendar function within the injector.

15. The medical device according to claim 1 wherein an electronic display such as an organic LED display is provide to display a menu system of mode and parameter selections plus device state and animation graphics for quality of visual communication to the patient or caregiver, and further, a membrane keypad located for the user to interface with the device, and further, a speaker to annunciate any audio cues facilitating interaction with the keypad or the display.

16. The medical device according to claim 1 wherein distractions and comforts are provided to the patient to reduce patient apprehension and anxiety and needle phobia; these distractions and comforts being provided by: a concealment of the needle and syringe both before during and after the injection, haptic vibrations into the skin indicating correct placement of the device onto the patient's skin, audio tonal vibrations indicating correct placement of the device onto the patient's skin, electrical sensory stimulation at the site of injection which suppresses pain, audio cues and musical themes indicating the start, duration, an end of injection, and human spoken language which instructs and re-assures the patient during every step of the injection process.

17. The medical device according to claim 7 wherein the plunger actuator is capable of drawing back on the syringe plunger to create a vacuum within the syringe in order to aspirate the tissue the needle has penetrated; further, an optical photometric system capable of measuring the reduction of wavelengths absorbed by heme in blood provides indication that the needle has punctured a vein and blood has been aspirated into the syringe cylinder, providing information which is used to instruct the user by way of human spoken language or the display or both, that a vein has been punctured wherein, the injector instructs the user in the proper steps to begin the injection over in a new location.

* * * * *